US009220681B2

(12) United States Patent
Coulter et al.

(10) Patent No.: US 9,220,681 B2
(45) Date of Patent: Dec. 29, 2015

(54) FORMULATIONS

(71) Applicant: Sigmoid Pharma Limited, Dublin (IE)

(72) Inventors: Ivan Coulter, County Dublin (IE); Bernard Francis McDonald, County Monaghan (IE); Vincenzo Aversa, County Dublin (IE); Mónica Rosa, Dublin (IE)

(73) Assignee: Sigmoid Pharma Limited, Dublin (IE)

( * ) Notice: Subject to any disclaimer, the term of this patent is extended or adjusted under 35 U.S.C. 154(b) by 0 days.

(21) Appl. No.: 13/935,859

(22) Filed: Jul. 5, 2013

(65) Prior Publication Data

US 2014/0017313 A1   Jan. 16, 2014

Related U.S. Application Data

(60) Provisional application No. 61/782,066, filed on Mar. 14, 2013.

(30) Foreign Application Priority Data

Jul. 5, 2012   (GB) .................................. 1212010.1

(51) Int. Cl.
| | | |
|---|---|---|
| A61K 39/02 | (2006.01) | |
| A61K 39/39 | (2006.01) | |
| A61K 9/14 | (2006.01) | |
| A61K 9/06 | (2006.01) | |
| A61K 39/108 | (2006.01) | |
| A61K 39/12 | (2006.01) | |
| A61K 47/36 | (2006.01) | |
| A61K 9/50 | (2006.01) | |
| A61K 9/51 | (2006.01) | |
| A61K 39/00 | (2006.01) | |

(52) U.S. Cl.
CPC . *A61K 9/06* (2013.01); *A61K 9/146* (2013.01); *A61K 9/5073* (2013.01); *A61K 9/5161* (2013.01); *A61K 39/0002* (2013.01); *A61K 39/0208* (2013.01); *A61K 39/0258* (2013.01); *A61K 39/107* (2013.01); *A61K 39/12* (2013.01); *A61K 39/39* (2013.01); *A61K 47/36* (2013.01); *A61K 2039/52* (2013.01); *A61K 2039/54* (2013.01); *A61K 2039/542* (2013.01); *A61K 2039/55511* (2013.01)

(58) Field of Classification Search
CPC ... A61K 31/155; A61K 31/37; A61K 31/395; A61K 31/4174; A61K 31/7036; A61K 33/30; A61K 33/38; A61K 36/534; A61K 36/537; A61K 36/886; A61K 45/06; A61K 47/06; A61K 47/20; A61K 47/34; A61K 9/1075; A61K 9/01
See application file for complete search history.

(56) References Cited

U.S. PATENT DOCUMENTS

| | | |
|---|---|---|
| 4,279,632 A | 7/1981 | Frosch et al. |
| 4,379,454 A | 4/1983 | Campbell et al. |
| 4,422,985 A | 12/1983 | Morishita et al. |
| 4,460,563 A | 7/1984 | Calanchi |
| 4,481,157 A | 11/1984 | Morishita et al. |
| 4,597,959 A | 7/1986 | Barr |
| 4,601,894 A | 7/1986 | Hanna et al. |
| 4,652,441 A | 3/1987 | Okada et al. |
| 4,656,161 A | 4/1987 | Herr |
| 4,695,466 A | 9/1987 | Morishita et al. |
| 4,748,023 A | 5/1988 | Tamás et al. |
| 4,749,574 A | 6/1988 | Ueda et al. |
| 4,751,241 A | 6/1988 | Motoyama et al. |
| 4,857,335 A | 8/1989 | Bohm |
| 5,102,668 A | 4/1992 | Eichel et al. |
| 5,145,684 A | 9/1992 | Liversidge et al. |
| 5,330,835 A | 7/1994 | Kikuchi et al. |
| 5,342,625 A | 8/1994 | Hauer et al. |
| 5,362,564 A | 11/1994 | Suzuki et al. |
| 5,385,737 A | 1/1995 | Shigeno et al. |
| 5,411,952 A | 5/1995 | Kaswan |
| 5,418,010 A | 5/1995 | Janda et al. |
| 5,478,508 A | 12/1995 | Suzuki et al. |
| 5,480,655 A | 1/1996 | Jizomoto et al. |
| 5,492,701 A | 2/1996 | Cervos et al. |
| 5,500,224 A | 3/1996 | Vranckx et al. |
| 5,510,118 A | 4/1996 | Bosch et al. |

(Continued)

FOREIGN PATENT DOCUMENTS

| | | |
|---|---|---|
| AU | 1977031116 | 12/1976 |
| AU | 627220 B2 | 8/1992 |

(Continued)

OTHER PUBLICATIONS

Xu et al. "Structure Evolution of Gelatin Particles Induced by pH and Ionic Strength," *Microscopy Research and Technique*, 76:272-281, 2013.
Xu et al. "Effects of anionic surfactants on grafting density of gelatin modified with PDMS-E," *Colloids and Surfaces B: Biointerfaces*, 114:310-315, 2014.
Bowersock et al. "Oral vaccination with alginate microsphere systems," *Journal of Controlled Release*, 39: 209-230, 1996.

(Continued)

*Primary Examiner* — Padma V Baskar
(74) *Attorney, Agent, or Firm* — Klarquist Sparkman, LLP

(57) ABSTRACT

This invention relates to compositions for delivering one or more active ingredients, and more particularly to compositions, e.g. beads, comprising a matrix material which matrix material comprises a microorganism. In particular, the invention relates to compositions comprising a microorganism selected from live, killed, attenuated and inactivated microorganisms. The matrix material may also comprise a surfactant and may further comprise an adjuvant. The invention further relates to the manufacture and use of such compositions, and to other subject matter.

48 Claims, 12 Drawing Sheets

(56) References Cited

U.S. PATENT DOCUMENTS

| | | | |
|---|---|---|---|
| 5,529,777 | A | 6/1996 | Andrianov et al. |
| 5,529,783 | A | 6/1996 | Burke et al. |
| 5,571,533 | A | 11/1996 | Santus et al. |
| 5,645,856 | A | 7/1997 | Lacy et al. |
| 5,650,232 | A | 7/1997 | Glenn et al. |
| 5,665,386 | A | 9/1997 | Benet et al. |
| 5,674,495 | A | 10/1997 | Bowersock et al. |
| 5,795,590 | A | 8/1998 | Kiefer et al. |
| 5,827,531 | A | 10/1998 | Morrison et al. |
| 5,843,347 | A | 12/1998 | Nguyen et al. |
| 5,871,774 | A | 2/1999 | Lemelson |
| 5,882,680 | A | 3/1999 | Suzuki et al. |
| 5,961,970 | A | 10/1999 | Lowell et al. |
| 6,022,562 | A | 2/2000 | Autant et al. |
| 6,113,936 | A | 9/2000 | Takebayashi et al. |
| 6,146,663 | A | 11/2000 | Bissery et al. |
| 6,174,466 | B1 | 1/2001 | Kiefer et al. |
| 6,190,692 | B1 | 2/2001 | Busetti et al. |
| 6,251,661 | B1 | 6/2001 | Urabe et al. |
| 6,267,985 | B1 | 7/2001 | Chen et al. |
| 6,284,271 | B1 | 9/2001 | Lundberg et al. |
| 6,309,663 | B1 | 10/2001 | Patel et al. |
| 6,361,298 | B1 | 3/2002 | Kiefer et al. |
| 6,429,089 | B1 | 8/2002 | Matsuki |
| 6,457,339 | B2 | 10/2002 | Komura |
| 6,531,150 | B1 | 3/2003 | Sunohara et al. |
| 6,569,463 | B2 | 5/2003 | Patel et al. |
| 6,585,997 | B2 | 7/2003 | Moro et al. |
| 6,761,903 | B2 | 7/2004 | Chen et al. |
| 6,923,988 | B2 | 8/2005 | Patel et al. |
| 6,972,132 | B1 | 12/2005 | Kudo et al. |
| 7,097,857 | B2 | 8/2006 | Tracy et al. |
| 7,267,813 | B2 | 9/2007 | Watanabe et al. |
| 7,374,779 | B2 | 5/2008 | Chen et al. |
| 7,727,551 | B2 | 6/2010 | Massironi |
| 2001/0003589 | A1 | 6/2001 | Neuer et al. |
| 2001/0024658 | A1 | 9/2001 | Chen et al. |
| 2002/0009457 | A1 | 1/2002 | Bowersock et al. |
| 2002/0098242 | A1 | 7/2002 | Darder |
| 2003/0045516 | A1 | 3/2003 | Luly et al. |
| 2003/0078194 | A1 | 4/2003 | Cho et al. |
| 2003/0104048 | A1 | 6/2003 | Patel et al. |
| 2003/0124061 | A1 | 7/2003 | Roberts |
| 2003/0180352 | A1 | 9/2003 | Patel et al. |
| 2003/0193102 | A1 | 10/2003 | Yan |
| 2003/0232076 | A1 | 12/2003 | Makino et al. |
| 2003/0235595 | A1 | 12/2003 | Chen et al. |
| 2004/0028619 | A1 | 2/2004 | Watanabe et al. |
| 2004/0029855 | A1 | 2/2004 | Klaveness et al. |
| 2004/0062802 | A1 | 4/2004 | Hermelin |
| 2004/0126428 | A1 | 7/2004 | Hughes et al. |
| 2004/0230183 | A1 | 11/2004 | Breegi et al. |
| 2004/0258701 | A1 | 12/2004 | Dominowski et al. |
| 2004/0258702 | A1 | 12/2004 | Blonder et al. |
| 2005/0095288 | A1 | 5/2005 | Honea |
| 2005/0249807 | A1 | 11/2005 | Brown et al. |
| 2006/0018965 | A1 | 1/2006 | Moodley et al. |
| 2006/0034937 | A1 | 2/2006 | Patel |
| 2006/0068019 | A1 | 3/2006 | Dalziel et al. |
| 2006/0135441 | A1 | 6/2006 | Khodadoust et al. |
| 2006/0222701 | A1 | 10/2006 | Kulkarni et al. |
| 2007/0154554 | A1 | 7/2007 | Burgermeister et al. |
| 2007/0292523 | A1 | 12/2007 | Moodley et al. |
| 2008/0020018 | A1 | 1/2008 | Moodley et al. |
| 2008/0107694 | A1 | 5/2008 | Trogden et al. |
| 2008/0113031 | A1 | 5/2008 | Moodley et al. |
| 2008/0124279 | A1 | 5/2008 | Andremont et al. |
| 2008/0311201 | A1 | 12/2008 | Der-Yang et al. |
| 2008/0317769 | A1 | 12/2008 | Kang et al. |
| 2008/0318912 | A1 | 12/2008 | Fox et al. |
| 2010/0136105 | A1 | 6/2010 | Chen et al. |
| 2010/0215737 | A1 | 8/2010 | Coulter |
| 2010/0239665 | A1 | 9/2010 | Coulter |
| 2010/0255087 | A1 | 10/2010 | Coulter |
| 2010/0297221 | A1 | 11/2010 | Coulter |
| 2011/0052645 | A1 | 3/2011 | Coulter |
| 2012/0141531 | A1 | 6/2012 | Coulter et al. |
| 2012/0141585 | A1 | 6/2012 | Coulter et al. |
| 2013/0243873 | A1 | 9/2013 | Aversa et al. |

FOREIGN PATENT DOCUMENTS

| | | |
|---|---|---|
| CA | 2170748 | 3/1995 |
| CA | 2376261 | 6/2000 |
| CN | 1557283 | 12/2004 |
| DE | 198 48 849 | 10/1998 |
| EP | 0 348 910 | 6/1989 |
| EP | 0 396 425 | 11/1990 |
| EP | 0 525 731 | 2/1993 |
| EP | 0 550 067 | 7/1993 |
| EP | 0 621 775 | 11/1994 |
| EP | 0 650 721 | 5/1995 |
| EP | 0 760 237 | 3/1997 |
| EP | 0 778 083 | 6/1997 |
| EP | 0 922 451 | 6/1999 |
| EP | 0 813 876 | 3/2002 |
| EP | 0 789 561 | 4/2004 |
| EP | 2 105 129 | 9/2009 |
| JP | A-58 013508 | 1/1983 |
| JP | A-58 077810 | 5/1983 |
| JP | 59-088420 | 5/1984 |
| JP | S61126016 A | 6/1986 |
| JP | A-61 151119 | 7/1986 |
| JP | H0549899 A | 3/1993 |
| JP | H06254382 A | 9/1994 |
| JP | 7247215 A | 9/1995 |
| JP | 2000-247911 | 9/2000 |
| JP | 2000-302654 | 10/2000 |
| JP | 2004-43332 A | 2/2004 |
| JP | 2005-500336 | 1/2005 |
| JP | 2008-512371 | 4/2008 |
| JP | 64-000015 | 8/2010 |
| WO | WO 91/06282 | 5/1991 |
| WO | WO 93/00063 | 1/1993 |
| WO | WO 94/15636 | 7/1994 |
| WO | WO 96/36322 | 11/1996 |
| WO | WO 97/02017 | 1/1997 |
| WO | WO 98/18610 | 5/1998 |
| WO | WO 98/50018 | 11/1998 |
| WO | WO 98/50033 | 11/1998 |
| WO | WO 99/06024 | 2/1999 |
| WO | WO 99/13914 | 3/1999 |
| WO | WO 00/00179 | 1/2000 |
| WO | WO 00/33862 | 6/2000 |
| WO | WO 00/69420 | 11/2000 |
| WO | WO 01/08666 | 2/2001 |
| WO | WO 01/37808 | 5/2001 |
| WO | WO 01/051008 | 7/2001 |
| WO | WO 01/80831 | 11/2001 |
| WO | WO 02/064162 | 8/2002 |
| WO | WO 03/009812 A2 | 2/2003 |
| WO | WO 03/018134 | 3/2003 |
| WO | WO 03/020243 | 3/2003 |
| WO | WO 03/030878 | 4/2003 |
| WO | WO 03/056938 | 7/2003 |
| WO | WO 03/092741 | 11/2003 |
| WO | WO 2004/022220 | 3/2004 |
| WO | WO 2004/042024 | 5/2004 |
| WO | WO 2004/064997 | 8/2004 |
| WO | WO 2004/084870 | 10/2004 |
| WO | WO 2004/087204 A2 | 10/2004 |
| WO | WO 2004/108121 | 12/2004 |
| WO | WO 2005/020993 | 3/2005 |
| WO | WO 2005/020994 | 3/2005 |
| WO | WO 2005/030205 | 4/2005 |
| WO | WO 2005/048998 | 6/2005 |
| WO | WO 2005/072088 | 8/2005 |
| WO | WO 2005/074913 | 8/2005 |
| WO | WO 2005/100454 | 10/2005 |
| WO | WO 2005/107721 | 11/2005 |
| WO | WO 2006/026592 | 3/2006 |
| WO | WO 2006/027685 A2 | 3/2006 |
| WO | WO 2006/035416 | 4/2006 |
| WO | WO 2006/110802 | 10/2006 |

(56) References Cited

FOREIGN PATENT DOCUMENTS

| WO | WO 2007/007946 | | 1/2007 |
|---|---|---|---|
| WO | WO 2007/012478 | | 2/2007 |
| WO | WO 2007/014445 | | 2/2007 |
| WO | WO 2007/018943 | | 2/2007 |
| WO | WO 2007/095092 | | 8/2007 |
| WO | WO 2008/122965 | | 10/2008 |
| WO | WO 2009/002533 | | 12/2008 |
| WO | WO 2009/014774 | | 1/2009 |
| WO | WO 2009-060305 | A2 | 5/2009 |
| WO | WO 2010/005980 | | 1/2010 |
| WO | WO 2011/018504 | A2 * | 2/2011 |

OTHER PUBLICATIONS

Florindo et al. "The enhancement of the immune response against *S. equi* antigens through the intranasal administration of poly-ε-caprolactone-based nanoparticles," *Biomaterials*, 30: 879-891, 2009.

Shioji, Yusaku "Manufacturing technology of solid formulation", CMC Publishing Co. Ltd., pp. 46-48 and 174-177, Jan. 27, 2003.

Office action issued for Japanese Patent Application No. 2006-507572.

Dhara et al., "Stability of Sodium Dodecyl Sulfate Micelles in the Presence of a Range of Water-Soluble Polymers: A Pressure-Jump Study," *J. Phys. Chem. B.*, 105: 7133-7138; 2001.

Greener et al., "Interaction of Anionic Surfactants with Gelatin: Viscosity Effects," *Macromolecules*, 20: 2490-2498; 1987.

Holmberg et al., *Surfactants and Polymers in Aqueous Solution*. John Wiley & Sons, Ltd. 2002.

Muller et al. "Competitive Adssorption of Gelatin and Sodium Dodecylbenzenesulfonate at Hydrophobic Surfaces," *Langmuir*, 14: 3107-3114; 1998.

Wesley et al., "Structure of Polymer/Surfactant Complexes Formed by Poly(2-(dimethylamino)ethyl metharylate) and Sodium Dodecyl Sulfate," *Langmuir* 18: 5704-5707; 2002.

"Nimotop® (nimiodipine) Capsules for Oral Use," FDA approved label text, Bayer Health Care: 2005.

Al-Meshal et al., "Oral administration of liposomes containing cyclosporine: a pharmacokinetic study," *International Journal of Pharmaceutics* 168:163-168, 1998.

Anderberg et al., "Sodium Caprate Elicits Dilatations in Human Intestinal Tight Junctions and Enhances Drug Absorption by the Paracellular Route," *Pharmaceutical Research* 10(6):857-864, 1993.

Barnes et al., "Theophylline: New Perspectives for an Old Drug," *AM J Respir Crit Care Med* 167:813-818, 2003.

Borel et al., "Carotenoids in biological emulsions: solubility, surface-to-core distribution, and release from lipid droplets," *Journal of Lipid Research* 37:250-261, 1996.

Cannon, "Oral Solid Dosage Forms of Lipid-based Drug Delivery Systems," *AM Pharm Rev* 8(1):108-115, 2005.

Chourasia et al., "Pharmaceutical approaches to colon targeted drug delivery systems," *J. Pharm. Pharmaceut. Sci.* 6(1):33/66/2003.

Chowdary et al., "Controlled Nifedipine Release from Microcapsules of its Dispersions in PVP-MCC and HPC-MCC," *Drug Development and Industrial Pharmacy* 21(10):1183-1192, 1995.

Drewe et al., "The absorption site of cyclosporine in the human gastro-intestinal tract," *Br. J. din. Pharmac.* 33:39-43, 1992.

Gao et al., "Physiochemical characterization and evaluation of a microemulsion system for oral delivery of yclosporine A," *International Journal of Pharmaceutics* 161:75-86, 1998.

Gursoy et al., "Self-emulsifying drug delivery systems (SEDDS) for improved oral delivery of lipophilic drugs," *Biomedicine & Pharmacotherapy* 58:173-182, 2004.

Ikegawa et al., Inhibition of P-glycoprotein by flavonoid derivatives in Adriamycin-resistant human myelogenous leukemia (K562/ADM)cells, *Cancer Letters* 177:89-93, 2002.

Kim et al., "Once-a-Day Oral Dosing Regimen of Cyclosporin A: Combined Therapy of Cyclosporin A Premicroemulsion Concentrates and Enteric Coated Solid-State Premicroemulsion Concentrates," *Pharmaceutical Research* 18(4):454-459, 2001.

Klausner et al. "Expandable gastroetentive dosage forms," *Journal of Controlled Release* 90:143-162, 2003.

Lawrance "Novel topical therapies for distal colitis," *World Journal of Gastrointestinal Pharmacology and Therapeutics* 1(5):87-93, 2010.

Liu et al., "Gelatin-Stabilised Microemulsion-Based Organogels Facilitates Percutaneous Penetration of Cyclosporin A in Vitro and Dermal Pharmacokinetics In Vivo," *Journal of Pharmaceutical Sciences* 96(11):3000-3009, Nov. 2007.

Loufrani, et al. "Vasodilator treatment with hydralazine increases blood flow in mdx mice resistance arteries without vascular wall remodeling or endothelium function improvement," *Journal of Hypertension* 23(10):1855-1860, 2005.

Madene et al., "Flavour encapsulation and controlled release—a review," *International Journal of Food Science and Technology* 41:1-21, 2006.

Manakova et al., "Failure of FK506 (tacrolimus) to alleviate apomorphine-induced circling in rat Parkinson model in spite of some cytoprotective effects in SH-SY5Y dopaminergic cells," *Brain Research* 1038:83-91, 2005.

McGinity et al., "Aqueous Polymeric Coatings for Pharmaceuticals Dosage Forms," *Marcel Dekker, Inc.*, 1997.

McGinity et al., "Enteric Film Coating of Soft Gelatin Capsules," *Drug Delivery & Development*, 3(6).

Miller et al., "Controlled Trial of Nimodipine in Amyotrophic Lateral Sclerosis," *Neuromusc. Disord.*, 6(2):101-104, 1996.

Milojevic et al., "Amylose as a coating for drug delivery to the colon: Preparation and in vitro evaluation using 5-aminosalicylic acid pellets," *Journal of Controlled Release* 38:75-84, 1996.

Mohan et al., "Focused Examination of the Intestinal lamina Propria Yields Greater Molecular Insight into Mechanisms Underlying SIV Induced Immune Dysfunction," *PLoS ONE* 7(4):e34S61, Apr. 12, 2012.

Murthy et al., "Treatment of Dextran Sulfate Sodium-Induced Murine Colitis by Intracolonic Cyclosporin," *Digestive Diseases and Sciences* 38(9):1722-1734, Sep. 1993.

Newman, et al. "Use of Nonionic Block Copolymers in Vaccines and Therapeutics," *Critical Reviews™ in Therapeutic Drug Carrier Systems* 15(2):89-142, 1998.

Ribeiro et al., "Microencapsulation of lipophilic drugs in chitosan-coated alginate microspheres," *International Journal of Pharmaceutics* 187:115-123, 1999.

Riviere, et al. "Effects of Vasoactive Drugs on Transdermal Lidocaine Iontophoresis," *Journal of Pharmaceutical Sciences* 80(7):615-620, 1991.

Rodriguez et al., "Colonic budesonide delivery from ph-dependent microcapsules containing lipidic cores," *Acta Technologiae et Legis Medicamenti* 11(1):45-52, 2000.

Strowig et al., Comparison of Insulin Monotherapy and Combination Therapy with Insulin and Metformin or Insulin and Troglitazone in Type 2 Diabetes, *Diabetes Care* 25(10):1691-1698, 2002.

Sweetman and Martindale, "Nimodipine," *Cardiovascular Drugs* p. 946, 2002.

Westerink et al. "ProJuvant™ (Pluronic F127®/chitosan) enhances the immune response to intranasally administered tetanus toxoid," *Vaccine* 20:711-723, 2002.

Yang et al., "Transport and uptake characteristics of a new derivative of berberine (CPU-86017) by human intestinal epithelial cell line: Caco-2," *Acta Pharmacol Sin* 24(12):1185-1191, 2003.

Yeh et al., "Effect of Medium-Chain Glycerides on Physiological Properties of Rabbit Intestinal Epithelium in Vitro," *Pharmaceutical Research* 11(8):1148-1154, 1994.

Zhang et al., "P-glycoprotein restricted transport of nimodipine across blood-brain barrier," *Acta Pharmacol Sin* 24(9) 903-906, 2003.

Zuber et al., "Reversible cerebral angiopathy," *J. Neurol* 253:1585-1588, 2006.

Holmgren et al., "Mucosal immunity and vaccines," *Nature Medicine*, 11(4): 545-553, Apr. 2005.

Wakerly et al., "Pectin/Ethylcellulose Film Coating Formulations for Colonic Drug Delivery," Pharmaceutical Research, 13(8): 1210-1212, 1996.

\* cited by examiner

Figure 1. Immunization with ETEC and alpha-GalCer in LEDDS™ induces significantly stronger mucosal antibody titres than delivery of antigen in solution or in non-adjuvanted LEDDS™.

Figure 2. Oral administration of ETEC with alpha-GalCer in LEDDS™ induces potent antigen-specific IgA responses in faecal pellets.

Figure 3. Oral immunisation with ETEC and alpha-GalCer in LEDDS™ induces strong antigen-specific systemic antibody responses.

Figure 4. Oral administration of ETEC with alpha-GalCer in LEDDS™ induces potent antigen-specific IgA responses systemically.

Figure 5. Oral immunisation of mice with ETEC and alpha-GalCer in LEDDS™ induces a predominant IgG1 antibody response systemically.

Figure 6. Oral immunization of mice with LEDDS™ containing ETEC and alpha-GalCer as adjuvant induces IgG antibody responses locally in the intestines.

Figure 7. Oral immunization of mice with LEDDS™ containing ETEC and alpha-GalCer as adjuvant induces significant IgA antibody responses locally in the intestines.

Figure 8. Oral immunization of mice with LEDDS™ containing ETEC and alpha-GalCer as adjuvant induces significant IgG antibody responses locally in the intestines.

Reference Study 1: Systemic Antibody Response

CTB solution versus LEDDS with CTB, alphaGalCer and Solutol

FORMULATIONS

CROSS REFERENCE TO RELATED APPLICATION

This application claims the benefit of U.S. Provisional Application No. 61/782,066, filed Mar. 14, 2013, which is incorporated herein by reference in its entirety.

This invention relates to compositions for delivering one or more active ingredients, and more particularly to compositions, e.g. beads, comprising a matrix material which matrix material comprises a microorganism. In particular, the invention relates to compositions comprising a microorganism selected from live, killed, attenuated and inactivated microorganisms. The matrix material may also comprise a surfactant and may further comprise an adjuvant. The invention further relates to the manufacture and use of such compositions, and to other subject matter.

BACKGROUND

The prior art discloses a modified release dosage product comprising a plurality of minicapsules (also termed "beads") containing an active ingredient. The beads may be produced by mixing two different liquids which are not or are hardly soluble with each other and one of which is an aqueous liquid comprising gelatin or another gelling agent. The liquids are mixed and the resulting mixture is ejected through a nozzle which may have a single orifice. The nozzle may be vibrated as the mixture is ejected through it. The ejected mixture forms into drops which are more or less spherical and fall into a cooling gas (e.g. air) or into a cooling or hardening solution whereby the gelling agent gels and the drops become minicapsules. There are disclosed beads made by ejecting an oil-in-water emulsion whose aqueous phase comprises gelatin or another water-soluble polymer matrix material through a single orifice nozzle; the beads include an active agent and, after drying, can be described as a dried oil-in-water emulsion in which the dried aqueous phase comprises polymer matrix material. See for example WO 2004/084870, WO 2008/132712 and WO 2010/133609, all of which are incorporated herein in their entirety by reference. The size of the oil droplets of such prior art dried oil-in-water emulsions is not disclosed in the prior art but has been measured and found to be around 100 nm, or occasionally down to about 50 nm.

An X-ray tomography image of the bead of the above application WO 2010/133609 is shown in FIG. 9. The image illustrates the highly homogeneous nature of the bead i.e. the near universal dispersion of the oil phase throughout the aqueous phase.

Within the body dendritic cells play a vital role in the immune system. The main purpose of dendritic cells is to process antigen material and present the antigen to other cells of the immune system. Intestinal dendritic cells are found in the gut-associated lymphoid tissue, including the lamina propria of the small and large intestine, the isolated lymphoid follicles, the Peyer patches, and the mesenteric lymph nodes. Dendritic cells exist in two functionally distinct states: immature and mature cells. Immature dendritic cells are present in peripheral tissues and are mainly phagocytic cells; mature dendritic cells are found in lymphoid organs and are specialized in antigen presentation. Mature dendritic cells derive from immature cells after a maturation process that is initiated by inflammatory stimuli and that leads to a massive migration of dendritic cells to draining lymph nodes (Banchereau, *Nature*. 392:245-252; Steinman, *Eur. J. Immunol.* 37 S53-S60).

Several observations in humans and in mouse models of Inflammatory Bowel Disease suggest that dendritic cells may play a pathogenic role. Dysfunctional dendritic cells may: act by priming abnormal responses of T cells to the enteric flora in organized lymphoid tissues; sustain T cell reactivity within the inflamed mucosa through the interaction with T cells; and function as effector cells via the release of proinflammatory cytokines (Rescigno, *J. Clin. Invest.* 119:2441-2450).

Dendritic cells are potent immunostimulatory cells (Steinman1991) and intestinal dendritic cells actively participate in antigen capture across the intestinal epithelium by extending protrusions directly into the lumen for antigen sampling (Rescigno, *Nat. Immunol.* 2:361-367). These cells can take up and present both orally and intestinally administered antigens to naive T cells (Liu and MacPherson, 1991). Efficient capture and presentation of antigens by dendritic cells is thought to be central to the induction of an immune response (Colaco, 1999).

In the case of a known antigen as seen in celiac disease, a potential dendritic cell-based, antigen-specific strategy may take advantage of the ability of dendritic cells to expand and induce Tregs—the principal effectors of tolerance, which in turn suppress other dendritic cells that present disease-producing antigens (Steinman, *Immunity*. 29:319-324)

BRIEF SUMMARY OF THE DISCLOSURE

The full ambit of the invention is disclosed in the following specification and claims. To assist the reader, however, a brief and non-limiting overview is contained in this paragraph. The invention provides (amongst other things) beads obtainable by mixing an aqueous solution of gelatin or another hydrogel-forming polymer, a surfactant which may be a polyethoxylated fatty acid (e.g. a polyethoxylated hydroxy fatty acid) or polyethoxylated fatty alcohol, a microorganism selected from live, killed, attenuated and inactivated microorganisms, and optionally an adjuvant. At least a portion of the adjuvant may be associated with at least a portion of the surfactant. The mix is converted to beads which are considered to comprise a dispersion of surfactant self-assembly structures (e.g. micelles) in a hydrogel. The beads are then dried to result in surfactant self-assembly structures (e.g. micelles), or precursors to release such structures upon contact with water, dispersed in a polymer matrix. In any event, the invention includes dried surfactant-containing beads which deliver self-assembly structures (e.g. micelles) upon contact with water, e.g. in an aqueous medium of the GI tract (the aqueous medium may for example be extracted from a GI tract or synthetically produced). The products and methods disclosed in this paragraph are part of the invention and therefore may be claimed, even though the invention is not at all limited to the subject matter of this paragraph.

The invention provides in one aspect a composition which comprises: (i) a surfactant; and (ii) an active ingredient. The active ingredient comprises a microorganism selected from live, killed, attenuated and inactivated microorganisms. The composition may also comprise an adjuvant. The composition may additionally comprise one or more excipients selected from hydrogel-forming polymers, particularly thermotropic hydrogel forming polymers. The composition may consist essentially of the surfactant and one or more active ingredients. The composition may consist essentially of the surfactant, one or more active ingredients and water. The surfactant may be non-ionic. The surfactant may comprise a hydrophilic chain and a hydrophobic chain. Also to be mentioned are ionic, e.g. anionic surfactants.

The invention includes composition comprising: a matrix comprising a hydrogel-forming polymer; and comprised in the matrix, a microorganism selected from live, killed, attenuated and inactivated microorganisms, a surfactant and an adjuvant.

The invention provides in a particular embodiment a composition which comprises: (i) a surfactant; (ii) a microorganism selected from live, killed, attenuated and inactivated microorganisms; (iii) an adjuvant; and (iv) a hydrogel-forming polymer in which the surfactant, the microorganism and the adjuvant are included; wherein the composition when combined with water is capable of releasing self-assembly structures (e.g. micelles) comprising surfactant and adjuvant. Said water may for example be in the form of gastric, intestinal or colonic fluid or a simulated form of one of them. It will be recalled that the surfactant may comprise a hydrophilic chain and a hydrophobic chain.

For all the compositions disclosed herein, at least a portion of the adjuvant may be associated with at least a portion of the surfactant.

For all the compositions disclosed herein, at least a portion of the microorganism content may be associated with at least a portion of the surfactant.

The invention includes within its scope a composition which comprises: a hydrogel-forming polymer; self-assembly structures (e.g. micelles) dispersed in the polymer; and a microorganism. The hydrogel-forming polymer may be combined with water in a gel state or in a sol state, or the hydrogel-forming polymer may be dry. As described further herein, the composition may be coated.

The microorganism is selected from a live, killed, attenuated and inactivated microorganism. The microorganism may be included in the composition, with an adjuvant. In the invention, the microorganism is immunogenic, for example it contains (internally or externally) or expresses or releases an antigenic substance which alone or in combination with an adjuvant may trigger an immune response when administered to a subject. The composition, e.g. as mentioned in this paragraph, is for immunogenic use. In particular, the invention provides a composition comprising: a matrix comprising a hydrogel forming polymer; and comprised in the matrix, a microorganism selected from live, killed, attenuated and inactivated microorganisms, a surfactant and an adjuvant.

The surfactant which may be in the form of self-assembly structures (e.g. micelles) or which is capable of forming self-assembly structures (e.g. micelles) when combined with water is sometimes referred to herein as the "self-assembly-forming surfactant" or "micelle-forming surfactant". (The surfactant may of course comprise a mixture of surfactant compounds).

An embodiment of the invention can be described as a dry hydrogel-forming polymer matrix comprising in the matrix a microorganism selected from live, killed, attenuated and inactivated microorganisms, a surfactant and an adjuvant. The dry hydrogel-forming polymer matrix may have therein a dispersion of self-assembly structures (e.g. micelles) comprising surfactant and, optionally, adjuvant. An embodiment of the invention can be described as a dry self-assembly structure-in-hydrogel dispersion (e.g. a micelle-in-hydrogel dispersion) wherein the self-assembly structure-former is, or comprises, surfactant and particularly a compound which comprises a hydrophilic chain and a hydrophobic chain. An embodiment of the invention can be described as a dried self-assembly structure-in-hydrogel dispersion wherein, in some embodiments, the self-assembly structure-former is, or comprises, a compound which comprises a hydrophilic chain and a hydrophobic chain. In one embodiment the composition is not a powder. In other embodiments the composition is moulded and/or shaped e.g. in the form of beads e.g. spherical beads, or other shaped units. In embodiments the composition of the invention comprises multiple self-assembly structures within a moulded or shaped form e.g. a bead. It will be understood that the term "spherical" refers to beads which seem substantially or generally of spherical shape to the human eye and does not require a sphere to a mathematical standard. In other words, "spherical" beads as described herein are generally spheroidal in the sense of resembling or approximating to a sphere. A population of beads of the disclosure, though, may contain occasional non-spheroidal beads resulting from the manufacturing process, and reference herein to e.g. a multiplicity of beads or a population of beads encompasses such collections of beads which include not only spherical (spheroidal) beads as described herein but also non-spherical (i.e. non-spheroidal) beads.

The self-assembly structure forming surfactant (e.g. micelle-forming surfactant) when in a dry composition of the invention may be described as in the form of pro-self-assembly structures (e.g. pro-micelles).

The invention includes not only dry compositions but also "wet" compositions in which the hydrogel-forming polymer is in the form of a hydrogel. The invention includes liquids in which the hydrogel-forming polymer is in combination with water in a liquid state.

A benefit of the present invention which is unpredictable from the prior art is the provision of an effective vaccine formulation which may be advantageously administered orally. In particular, the invention provides an improved formulation for the delivery of a "whole cell" vaccine wherein an antigenic substance is delivered in the form of a microorganism selected from live, killed, attenuated and inactivated microorganisms. The inventors have devised a "whole cell" formulation that, when administered orally, has been found to induce a potent and antigen-specific antibody response (as demonstrate by in vivo data herein). The observed improvement in antibody response following administration of a "whole cell" formulation according to the invention was significant when compared to administration of a simple "whole cell" solution. In addition, and unexpectedly, the observed improvement in terms of systemic and local intestinal response, was more significant for "whole cell" formulations than for "sub-unit" formulations that have been tested, for example a cholera toxin B subunit formulation.

Another benefit of the invention is considered to be derived from the size of the self-assembly structures formed by the surfactant. In particular, micelles formed by the micelle-forming surfactant in an aqueous medium have been observed to be smaller than oil droplets obtained following the teaching of WO 2010/133609. Typically micelles formed according to the disclosure herein being 10-30 nm. This smaller size gives rise to a higher surface area than the larger oil droplets of the prior art, resulting in turn with better contact with the epithelium and better absorption. It is also to be mentioned that the surfactant micelles featured in embodiments of the invention (at least in terms of micelles released by the compositions in use) provide a more uniform population in terms of size, i.e. have a lower polydispersity as regards size. Such small micelle sizes of 10-30 nm (or so) are believed to be inherent to the compositions described in this specification but it is not mandatory, though it is an option, that the micelles should, or should predominantly (e.g. at least 75% of them and optionally at least 80% or at least 90%), have sizes within this range.

Certain compositions of the invention comprise: a microorganism selected from live, killed, attenuated and inactivated microorganisms; and an adjuvant; such compositions advantageously release both components together. For example, compositions have been tested comprising enterotoxigenic *Escherichia coli* (ETEC), which is a whole cell antigenic substance of which a portion of the cells may be fragmented, and α-GalCer, an adjuvant which is an amphiphilic glycolipid having both hydrophilic and hydrophobic groups by virtue of possessing a sugar head and a ceramide part which consists of a fatty acid and sphingoid chain. The actives ETEC and α-GalCer have been administered in a composition considered to be capable of releasing self-assembly structures, e.g. micelles, when combined with water, in the form of a composition comprising Kolliphor® as a self-assembly structure-forming agent, e.g. micelle-forming agent. It is believed that that during manufacture these compositions comprise self-assembly structures (e.g. comprising Kolliphor® as a or the self-assembly structure-forming surfactant) dispersed in a hydrogel (e.g. comprising gelatin). These compositions are then dried and optionally coated prior to storage and subsequent administration. The compositions have been found to be effectively immunogenic and immuno-protective. The prior art vaccine formulations as exemplified in WO 2010/133609, are protein-based and are dried oil-in-hydrogel emulsions. Without being confined by theory, it is speculated that the compositions of the invention release both agents together, enabling the adjuvant to prime the appropriate immune cells prior to, or at the same time as, contact with the antigen. Still without being confined by theory, it is considered that at least a portion of the α-GalCer associates with at least a portion of the self-assembly structure-forming surfactant (for example, Kolliphor®), e.g. includes itself in the surfactant envelope of micelles. Also in the context of vaccines, micelles are believed to be of favourable size for antigen-presenting cell, such as macrophage, B lymphocyte and dendritic cell uptake.

Therefore, an aspect of the invention provides a composition comprising a matrix comprising a hydrogel-forming polymer; and comprised in the matrix, a microorganism selected from live, killed, attenuated and inactivated microorganisms (for example, ETEC), a surfactant and an adjuvant. Also provided is a composition comprising a surfactant (for example a macrogol-15-hydroxystearate, particularly Kolliphor HS 15),
    a microorganism selected from live, killed, attenuated and inactivated microorganisms (for example ETEC)
    an adjuvant comprising α-GalCer, and
    a hydrogel-forming polymer in which the surfactant, the microorganism and the adjuvant, α-GalCer, are included
and wherein:
the composition when combined with water is capable of releasing self-assembly structures (e.g. micelles). In particular, the surfactant which is dispersed in the polymer and which may form self-assembly structures, for example micelles, when combined with water, is a macrogol-hydroxy fatty acid and particularly a macrogol-15-hydroxystearate, e.g. is Kolliphor, particularly Kolliphor HS 15, More particularly, the microorganism is ETEC.

The extent of absorption of substances by different parts of the gastrointestinal tract depends inter alia on the physicochemical properties of the substance concerned. Thus, hydrophobic active agents are better absorbed by the small intestine than by the colon. Certain microorganisms, such as particular ETEC strains, over-express, amongst other things, antigenic substances like CAF/I. Such strains thus have a hydrophobic surface (see PNAS, Jun. 30, 2009, vol. 106, no. 26, 10793-10798; and Infect. Immun, February 2006, p. 1062-1071; for further information). In particular, the invention contemplates a composition according to any one of the embodiments described herein which comprises a microorganism strain which express a colonisation factor, for example CAF/I. Such a strain may be selected from Recombinant *E. coli*, *Shigella*, *Salmonella* or *V. cholerae* strains overexpressing major colonization factors CAF/I, CAF/II, CAF/IV and others including DH5αλpir, SY327αλpir, SM10λpir, WS-4437A, WS-1858B, A18-34, A18-34Ap, A18-34ApTp, ACAM2010(pSTREP), E1392/75, E1392/75-2A, PTL003.

It is also desirable that formulations containing active agents, for example the microorganisms described herein, are protected from degradation in general, including protection from gastric acid and gastric or intestinal enzymes.

It is advantageous if the formulation is designed to permit the coincident release of adjuvant(s) and antigen(s) in a form that is readily ingested by or interacts in an appropriate manner with suitable immune cells that are at the surface of or lie beneath the gastrointestinal epithelial barrier.

The hydrogel-forming polymer matrix (which may be referred to as the aqueous phase of a dry dispersion) comprises, in one embodiment, a cross-linked hydrogel-forming polymer e.g. resulting from chemical or physico-chemical (e.g. drying) solidification of a fluid aqueous continuous phase such that, in the matrix or dry micelle dispersion, water is substantially absent and the micelles are immobilized. In this embodiment, the dry aqueous phase can therefore be referred to as an immobilization matrix.

The surfactant phase may optionally comprise, or be, a surfactant comprising a hydrophobic chain and a hydrophilic chain. Optionally, the surfactant phase may comprise an active ingredient (e.g. a hydrophobic active ingredient, an amphiphilic active ingredient, or both). The surfactant phase may comprise a hydrophobic excipient, optionally as well as an active ingredient. In some embodiments, the surfactant phase comprises an amphiphilic excipient, optionally as well as one or both of a hydrophobic excipient and an active agent.

The term "released" in relation to the self-assembly structures (e.g. micelles) means free to move, egress, coalesce, dissolve, (re)emulsify etc. although actual movement, egression, coalescence, association or (re)emulsification is not a requirement i.e. may not occur and indeed may intentionally be constrained e.g. by presence of a coat or coating and/or by incorporation of certain constraining or retarding substances into the hydrogel-forming polymer matrix.

The term "self-assembly structure" refers to any type of micelle, vesicle, microemulsion, lyotropic phase, laminar or other self-organised structure that forms spontaneously in the presence of an aqueous environment, or combination thereof. As is known, such self-assembly structures form when a self-assembly structure-forming substance, e.g. comprising or consisting of a surfactant, is present above a certain critical concentration. The term includes, for example, micelles, inverted micelles and liposomes, and combinations thereof. The self-assembly structures referred to in this specification may comprise, or be, micelles. More information on self-assembly structures can be found in "Dynamics of Surfactant Self-assemblies Micelles, Microemulsions, Vesicles and Lyotropic Phases" by Raoul Zana, particularly Chapter 1, all of which is incorporated herein by reference. The release of self-assembly structures from a bead or other composition may be determined by contacting the composition with water and observing for such structures by dynamic light scattering.

Certain embodiments comprise a microorganism selected from live, killed, attenuated and inactivated microorganisms and an adjuvant. Preferably the adjuvant is a direct- or indirect immunostimulant e.g. is an immune cell activator, for example an antigen-presenting cell activator or a T-cell activator. A representative antigen is enterotoxigenic *Escherichia*

*coli* (ETEC). A representative and preferred example of an adjuvant is α-galactosylceramide (α-GalCer) (e.g. KRN 7000) or another glycolipid adjuvant, for example another glycosylceramide other than α-GalCer or a glycosylceramide analogue. Glycosylceramide analogues are taught in WO 2004/028475, which is in its entirety incorporated herein by reference. α-Galactosylceramide is particularly preferred.

Considering now the self-assembly structure-forming surfactant, it may in particular be a non-ionic surfactant and in many embodiments comprises a PEG moiety, PEG also being known as poly(oxyethylene). The surfactant may comprise a hydrophobic chain selected from alkyl and alkenyl chains; the hydrophobic chain may be substituted, for example mono-substituted by e.g. hydroxy, provided that its hydrophobic character is maintained. In certain embodiments the self-assembly structure-forming surfactant is selected from the group consisting of: macrogol esters; macrogol ethers; diblock copolymers; triblock copolymers; and amphiphilic polymers, and combinations thereof. Preferably the surfactant is chosen from macrogol esters.

In certain embodiments, the surfactant may have a wax-like character. The surfactant may comprise polyglycol esters of fatty acids, for example polyglycol mono- and di-esters of fatty acids (for example stearic acid and/or 12-hydroxy stearic acid). In particular, the surfactant may comprise polyoxyethylene esters of fatty acid (for example stearic acid and/or 12-hydroxystearic acid). In such embodiments, a small part of the 12-hydroxy group can be etherified with polyethylene glycol. The surfactant may also comprise free polyethylene glycol.

In certain embodiments the surfactant is the macrogol ester macrogol-15-hydroxystearate. A representative macrogol-15-hydroxystearate is marketed as Kolliphor® HS 15 by BASF, which conforms to the requirements of the European Pharmacopoeia monograph number 2052 Macrogol-15-hydroxystearat, published in the 6$^{th}$ Edition, July 2006. A particular class of surfactants useful in the invention are therefore those which conform to the requirements of the European Pharmacopoeia monograph number 2052 Macrogol-15-hydroxystearat, published in the 6$^{th}$ Edition, July 2006. Reference herein to "Kolliphor" includes reference to Kolliphor HS 15. Kolliphor HS 15 may be replaced by another surfactant meeting the requirements of said monograph number 2052.

The hydrogel-forming polymer may be a thermotropic hydrogel-forming polymer, or a combination of such polymers. The hydrogel-forming polymer may be gelatin.

Further provided is a self-assembly structure dispersion (and in particular a micelle dispersion) for use in manufacturing the composition of the invention, the self-assembly structure dispersion comprising a surfactant dispersed in an aqueous phase which comprises a liquid comprising water and a hydrogel-forming polymer. The dispersion may comprise an antigen comprising a microorganism selected from live, killed, attenuated and inactivated microorganisms. The dispersion may also comprise hydrophobic and/or amphiphilic active ingredients, for example, an adjuvant and particularly the adjuvant α-GalCer. The dispersion may comprise a hydrophilic active ingredient. It will be appreciated that the self-assembly structure dispersion may have the same constituents as the composition of the invention except that the self-assembly structure dispersion additionally contains a significant amount of water.

In another aspect, the invention provides a process for manufacturing a surfactant/active (e.g. microorganism) premix. A process of the invention comprises mixing a surfactant, an antigen comprising a microorganism selected from live, killed, attenuated and inactivated microorganisms, and optionally an adjuvant and particularly the adjuvant α-GalCer. The surfactant and the antigen may be as further described elsewhere herein.

The invention includes the following process and compositions obtainable by (having the characteristics of a composition obtained by) the process, whether directly or indirectly. The process comprises mixing:
  i) a surfactant premix comprising a surfactant, an adjuvant and a microorganism selected from live, killed, attenuated and inactivated microorganisms; and
  ii) a liquid aqueous premix comprising water and a hydrogel-forming polymer.

The process of the preceding paragraph may further comprises ejecting the mixture of i) and ii) through a single orifice nozzle to form droplets, the hydrogel-forming polymer then being caused or allowed to solidify whereby the droplets form beads. The hydrogel-forming polymer is a thermotropic polymer or a mixture of thermotropic polymers, and the aqueous premix is at an elevated temperature and the surfactant premix is at a temperature not exceeding ambient temperature, the two premixes flowing through respective feed lines to a mixing apparatus where the two premixes are mixed, and wherein at least one of the two premixes travels a greater distance through its feedline than the mixture does in travelling from the mixing apparatus to the nozzle. The two premixes may be mixed in-line at a location juxtaposed to the nozzle, e.g. by in-line mixing apparatus juxtaposed to the nozzle.

The invention further provides a process which comprises:
  (i) mixing materials comprising water, a hydrogel-forming polymer, a surfactant, and an active ingredient (for example a microorganism selected from live, killed, attenuated and inactivated microorganisms; and optionally an adjuvant) to form a self-assembly structure dispersion (possibly a micelle dispersion) within an aqueous phase comprising the hydrogel-forming polymer, the process optionally further comprising
  (ii) formulating the dispersion of (i) into a suitable form, e.g. a bead, by ejecting it through a single orifice nozzle to form droplets which are caused or allowed to pass into a cooling medium, e.g. a water-immiscible cooling liquid, in which the droplets cool to form shaped units e.g. beads.

The invention includes shaped units (e.g. beads) obtainable by the process, whether directly or indirectly, i.e. includes shaped units (e.g. beads) having the characteristics of shaped units obtained by the process, whether directly or indirectly In embodiments, the invention includes a process for manufacturing a composition or dispersion of the invention which comprises: forming an aqueous premix which comprises water and water soluble/dispersible materials and a surfactant premix (optionally containing an oil) which comprises surfactant and surfactant soluble/dispersible materials, and combining the two premixes to form a self-assembly structure dispersion (possibly a micelle dispersion) within an aqueous phase comprising the hydrogel-forming polymer. The dispersion may then be formed into a bead as described in the preceding paragraph. More particularly the manufacture of the composition may optionally comprise:

(i) forming an aqueous phase premix comprising, or usually consisting of, a solution in water of water-soluble constituents (e.g. hydrogel-forming polymer, any water-soluble excipient(s), any hydrophilic active(s) (for example, a microorganism could be included in the aqueous phase premix as, for example an aqueous suspension);

(ii) forming a surfactant phase premix comprising, or usually consisting of, a solution in a surfactant of hydrophobic and amphiphilic constituents (e.g. active ingredient(s) selected from a microorganism could be included directly in the surfactant premix or included as an aqueous suspension in the surfactant premix for example in the form of a water-in-surfactant emulsion);

(iii) mixing the two phases to form a dispersion; and optionally (iv) formulating the dispersion into a bead or other shaped unit, e.g. ejecting it through a single orifice nozzle to form droplets which are caused or allowed to fall into a water immiscible cooling liquid in which the droplets cool to form beads, and then separating the beads from the cooling liquid.

Further provided by the invention is a process which comprises mixing (i) a surfactant, and (ii) an active ingredient selected from a microorganism; the mixing may further comprise mixing a hydrophobic excipient, for example a medium chain triglyceride, and the surfactant and the microorganism. The resultant surfactant mix may be mixed with an aqueous composition comprising water and a hydrogel-forming polymer, the surfactant being in an amount sufficient to form self-assembly structures (e.g. micelles), the mixing thereby forming a self-assembly structure dispersion.

Another process of the invention is a process which comprises mixing materials comprising (i) water, (ii) a hydrogel-forming polymer, (iii) a surfactant, and (iv) an active ingredient, to form a self-assembly structure (e.g. micelle) dispersion within an aqueous phase comprising the hydrogel-forming polymer.

As an intermediate product obtained during manufacture of the final compositions of the disclosure, the invention includes a composition comprising a hydrogel having dispersed therein self-assembly structures (e.g. micelles) comprising a self-assembly structure-forming compound, the compound optionally being selected from compounds having a hydrophilic chain and a hydrophobic chain, the composition further comprising an active agent as described herein. The invention further provides a product having the characteristics of a composition obtained by drying a composition comprising a hydrogel having dispersed therein self-assembly structure (e.g. micelles) comprising a self-assembly structure (e.g. micelle)-forming compound, the compound optionally being selected from compounds having a hydrophilic chain and a hydrophobic chain, the composition further comprising an active agent.

It may also be advantageous, e.g. from a manufacturing perspective, to include an oil with the surfactant in the processes described herein. The surfactant phase may therefore additionally include an oil in the process and the surfactant in the product may be associated with an oil.

Any pharmaceutically suitable oil or oil acceptable for food use (or other chosen application) may be used as the oil. In terms of dry weight of the composition of the invention, the oil may comprise a proportion from 1% to 85%, e.g. 1% to 50%, optionally 1% to 30%, 1% to 20%, 1% to 10% or 1% to 5%, The oil may comprise 5% to 30%, 5% to 20% or 5% to 10%; it may comprise from 20% to 30% or from 35% to 45%. The term "oil" means any substance that is wholly or partially liquid at ambient temperature or close-to-ambient temperature e.g. between 10° C. and 40° C. or between 15° C. and 35° C., for example liquid at a temperature of up to 25° C. and whether or not liquid within the entirety of the aforesaid ranges, and which is hydrophobic but soluble in at least one organic solvent. Oils include vegetable oils (e.g. neem oil), petrochemical oils, and volatile essential oils.

As oils which may be included may be mentioned polyunsaturated fatty acids such as, for example, omega-3 oils for example eicosapentanoic acid (EPA), docosohexaenoic acid (DHA), alpha-linoleic acid (ALA), conjugated linoleic acid (CLA). Preferably ultrapure EPA, DHA or ALA or CLA are used e.g. purity up to or above 98%. Omega oils may be sourced e.g. from any appropriate plant e.g. sacha inchi. Such oils may be used singly e.g. EPA or DHA or ALA or CLA or in any combination. Combinations of such components including binary, tertiary etc combinations in any ratio are also contemplated e.g. a binary mixture of EPA and DHA in a ratio of 1:5 available commercially under the trade name Epax 6000.

Oils which may be included comprise, or are, particularly natural triglyceride-based oils which include olive oil, sesame oil, coconut oil, palm kernel oil. Oils which are particularly preferred include saturated coconut and palm kernel oil-derived caprylic and capric fatty acids and glycerin e.g. as supplied under the trade name Miglyol™ a range of which are available and from which one or more components of the oil phase of the invention may be selected including Miglyol™ 810, 812 (caprylic/capric triglyceride); Miglyol™ 818: (caprylic/capric/linoleic triglyceride); Miglyol™ 829: (caprylic/capric/succinic triglyceride; Miglyol™ 840: (propylene glycol dicaprylate/dicaprate). Note that Miglyol™ 810/812 differ only in $C_8/C_{10}$-ratio and, because of its low $C_{10}$-content, the viscosity and cloud point of Miglyol™ 810 are lower. The Miglyol™ range is available commercially from Sasol Industries. As noted above, oils which may be included in the oil phase need not necessarily be liquid or fully liquid at room temperature. Alternative or additional oils which may be included in the oil phase according to the invention are medium chain triglycerides such as for example Labrafac™ Lipophile manufactured by Gattefosse in particular product number WL1349.

Other possible (alternative or additional) oils include linoleoyl macrogolglycerides (polyoxylglycerides) such as, for example, Labrafil (e.g. product number M2125CS by Gattefosse) and caprylocaproyl macrogolglycerides such as, for example, Labrasol by Gattefosse.

The beads which have been separated from the cooling liquid may be centrifuged to remove excess oil and then air-dried, e.g. at ambient temperature (say 15-30° C., e.g. 20-25° C.). The centrifuging normally takes place before the air drying.

As described in more detail later in this specification, a bead made as described herein may after its preparation be coated with one or more layers.

In a further aspect, the present invention provides for a dosage form comprising a population of optionally coated beads of the invention. The beads of the dosage form comprise an active ingredient as described herein. The dosage form is suitable for pharmaceutical use. In certain embodiments the dosage form may comprise at least two populations of beads.

In certain embodiments the dosage form comprises the composition (e.g. a bead or shaped unit and particularly multiple beads or shaped units) of the invention in a unit dosage form suitable for administration, for example to a human or animal. The unit dosage form chosen from a capsule, a tablet, a sprinkle, a sachet, a suppository, a pessary or other suitable unit dosage form.

In a representative embodiment a dosage form of the invention is formed by mixing together at least the following materials to form a self-assembly structure (e.g. micelle) dispersion: water; a hydrogel-forming polymer; a surfactant; and an active ingredient, and formulating the dispersion into a dosage form (suitable for pharmaceutical use) comprising a bead which comprises the dispersion in a dry state.

In some embodiments the dosage form has been appropriately formulated in such a way as to release the one or more active ingredients at one or more specified locations in the gastrointestinal tract (GIT). In particular the dosage form is formulated to release the microorganism and optional adjuvant in at least the upper small intestine and the dosage form may therefore be enteric coated. The dosage form may comprise enteric coated beads, for example the dosage form may be a capsule or other format comprising a plurality of enteric coated beads. The dosage form may target release elsewhere e.g. the ileum, the colon or both.

The dosage forms of the invention are in particular for oral administration.

The invention includes a method for administering a microorganism selected from live, killed, attenuated and inactivated microorganisms to a subject, comprising orally administering to the subject a composition or dosage form as disclosed herein, which composition or dosage form comprises such an active agent (e.g. a combination of (i) a microorganism selected from live, killed, attenuated and inactivated microorganisms and (ii) an adjuvant).

The invention also includes a method for administering an active pharmaceutical ingredient comprising a microorganism selected from live, killed, attenuated and inactivated microorganisms to a subject, the method comprising administering a dosage form comprising a population of beads. The beads comprise a matrix comprising a hydrogel-forming polymer, and comprised in the matrix, a surfactant, an optional adjuvant and a microorganism selected from live, killed, attenuated and inactivated microorganisms. The dosage form is for oral administration. The dosage form may be adapted to release the active ingredient in the gastrointestinal tract.

Provided by the invention also is a product having the characteristics of a composition obtained by drying a composition comprising a hydrogel having dispersed therein self-assembly structures (e.g. micelles), the composition further comprising a microorganism selected from live, killed, attenuated and inactivated microorganisms, and the use of the product in the manufacture of an oral dosage form, for example a gelatin capsule.

Further included in the invention is a process for administering a microorganism selected from live, killed, attenuated and inactivated microorganisms to a subject, comprising orally administering to the subject a product comprising an active agent (as described herein), wherein the product is a composition as described herein Also provided by the invention is a method for performing a treatment selected from:
 i. vaccinating a subject
 ii. induction of an immunotherapeutic response e.g. to treat diseases selected from cancers and autoimmune diseases (e.g. to control autoimmune diseases), the autoimmune diseases being selected from systemic and gastrointestinal autoimmune diseases
 iii. administration of active entities to induce or regulate immunity or to locally target metastatic or micrometastatic cells in the lymphatic system,
the method comprising administering a composition or dosage form as disclosed herein, which composition or dosage form comprises an active agent (as disclosed herein) (e.g. combination of active agents as disclosed herein) having an activity appropriate to achieve the recited treatment.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

BRIEF DESCRIPTION OF THE DRAWINGS

The trade mark "LEDDS" herein refers to a composition of the invention and more particularly a composition of the invention as described in the examples.

DETAILED DESCRIPTION

Figure 1:
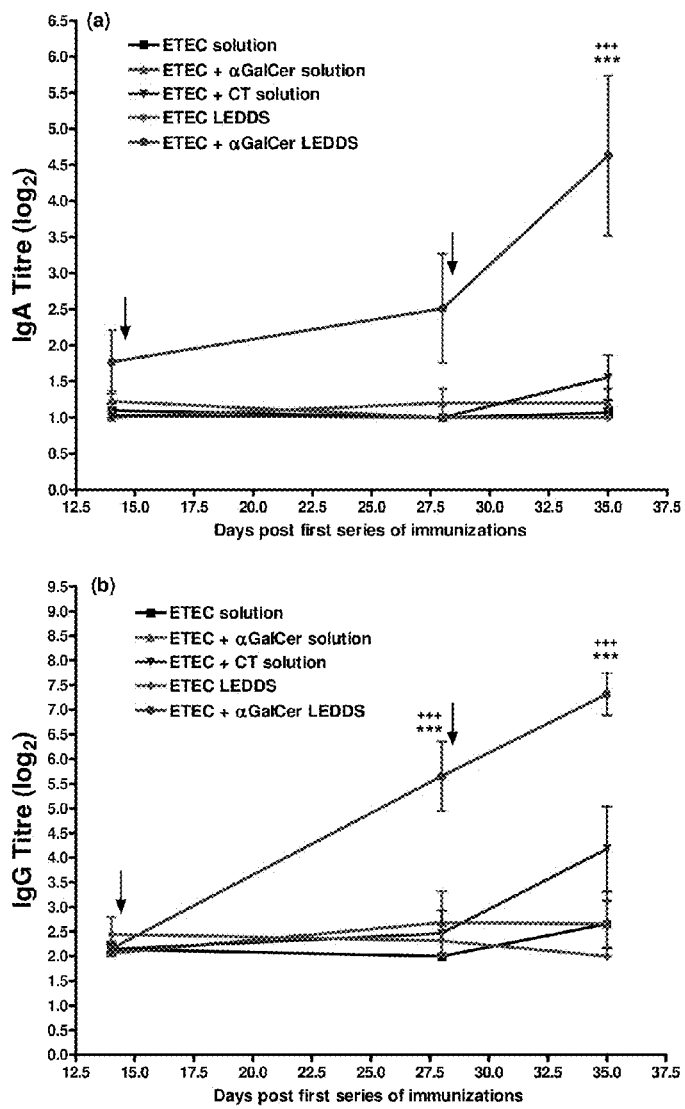
FIG. 1. Immunization with ETEC and alpha-GalCer in LEDDS™ induces significantly stronger mucosal antibody titres than delivery of antigen in solution or in non-adjuvanted LEDDS™. Mice were immunised on 2 consecutive days on week 0 with ETEC alone or with alpha-GalCer or CT in solution or with ETEC either alone or with alpha-GalCer in LEDDS™, followed by an identical series of booster immunisations at week 2 and 4. Faecal pellets were collected 1 day prior to booster immunizations and 12 days post the final immunization and antigen-specific IgA (a) and IgG (b) antibody titres were determined by ELISA. Arrows represent booster immunizations. ***, $P<0.001$ ETEC+alpha-GalCer LEDDS™ vs ETEC+alpha-GalCer solution, +++, $P<0.001$ ETEC+alpha-GalCer LEDDS™ vs ETEC LEDDS™.
Figure 2:
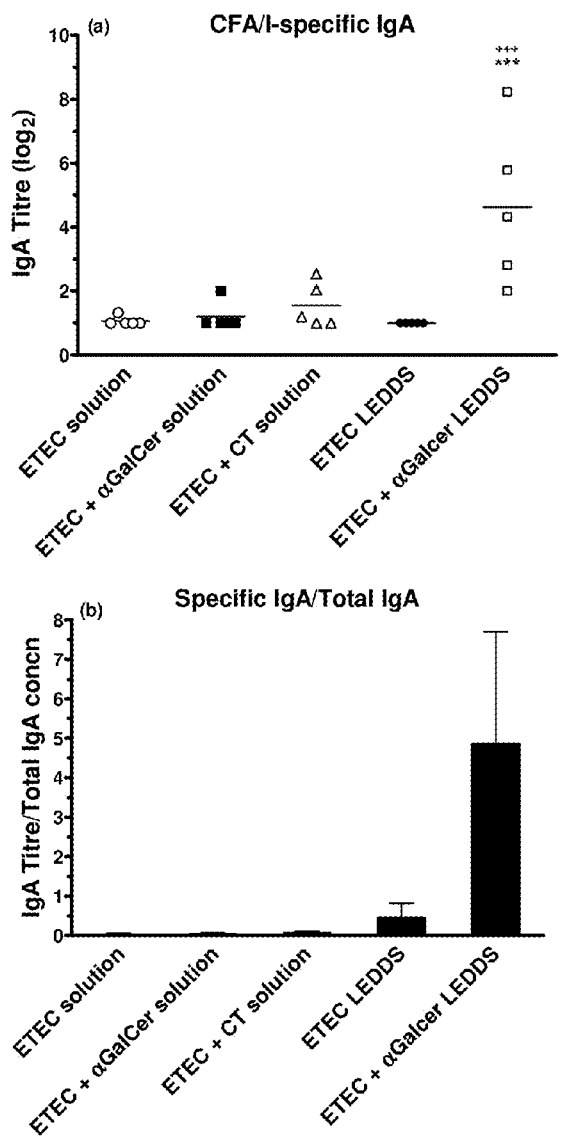
FIG. 2. Oral administration of ETEC with alpha-GalCer in LEDDS™ induces potent antigen-specific IgA responses in faecal pellets. Mice were immunised as described in the legend to FIG. 1. Faecal pellets were collected 12 days post the final immunization and antigen-specific IgA titres and total IgA antibody concentrations were assessed by ELISA. Results are expressed as CFA/1-specific IgA endpoint titres (a) or antigen-specific IgA titres/total IgA concentrations (b). +++$P<0.001$ ETEC+alpha-GalCer LEDDS™ vs ETEC solution, *** $P<0.001$ ETEC+alpha-GalCer LEDDS™ vs ETEC LEDDS™.

The term "amphiphilic" means the same as "amphipathic" and means containing both a hydrophilic group and a hydrophobic (lipophilic) group.

The term "associated with" includes reference to two substances being mixed or having an interface with each other. For example, where an adjuvant is associated with a surfactant in a bead or other dried composition, the association may be determined by identifying co-location of the adjuvant and the active using a suitable analytical technique. (Co-location means the existence of at least one location in which both substances are located). Analytical techniques to determine co-location may include TOFF, mapping Raman spectroscopy and infrared spectroscopy.

The phrase "pharmaceutically acceptable" refers to molecular entities and compositions that are generally regarded as safe. In particular, pharmaceutically acceptable carriers used in the practice of this invention are physiologically tolerable and do not typically produce an allergic or similar untoward reaction (for example, gastric upset, dizziness and the like) when administered to a patient. Preferably, as used herein, the term "pharmaceutically acceptable" means approved by a regulatory agency of the appropriate governmental agency or listed in the U.S. Pharmacopoeia or other generally recognized pharmacopoeia for use in animals, and more particularly in humans.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

The term "release", particularly in relation to self-assembly structure (e.g. micelles), includes reference both to releasing pre-existing self-assembly structures in a polymer matrix and to release self-assembly structures comprising surfactant not in self-assembly structure form in the polymer matrix but formed after ingestion of a composition of the invention as water and the self-assembly structure come into mutual contact. In other words a self-assembly structure released from a composition of the invention may be preformed in the composition or formed (in whole or in part) as part of the release process.

The term "treating" includes: (1) preventing or delaying the appearance of clinical symptoms of the state, disorder or condition developing in an animal that may be afflicted with or predisposed to the state, disorder or condition but does not yet experience or display clinical or subclinical symptoms of the state, disorder or condition; (2) inhibiting the state, disorder or condition (e.g., arresting, reducing or delaying the development of the disease, or a relapse thereof in case of maintenance treatment, of at least one clinical or subclinical symptom thereof); and/or (3) relieving the condition (i.e., causing regression of the state, disorder or condition or at least one of its clinical or subclinical symptoms). The benefit to a patient to be treated may be either statistically significant or at least perceptible to the patient or to the physician. The term "therapeutic or prophylactic" encompasses the same subject matter.

"Vaccine" is herein defined as a composition comprising an antigenic substance, in particular comprising modified-live (live attenuated) or inactivated infectious agent or microorganism, that is administered, most often with an adjuvant, into an animal to produce an immunologically mediated effect such as active immunity, induction of tolerance, breaking of tolerance, altering the course of an auto-immune disease etc. The composition of the invention may be a vaccine composition. Unless the context so demands, the term "vaccine composition" includes immunomodulation which is not necessarily vaccination e.g. toleration or other immunotherapy.

The term "subject" includes birds, humans and other mammals as well as fish, for example domestic animals (e.g., dogs and cats). The term "subject" in particular denotes a human.

"Effective amount" means an amount sufficient to result in the desired therapeutic or prophylactic response. The therapeutic or prophylactic response can be any response that a user (e.g., a clinician) will recognize as an effective response to the therapy. It is further within the skill of one of ordinary skill in the art to determine appropriate treatment duration, appropriate doses, and any potential combination treatments, based upon an evaluation of therapeutic or prophylactic response.

The terms "dry" and "dried" as applied to compositions of the disclosure may each include reference to compositions containing less than 5% free water by weight, e.g. less than 1% free water by weight. Primarily, however, "dry" and "dried" as applied to compositions of the disclosure mean that the hydrogel present in the initial solidified composition has dried sufficiently to form a rigid composition.

As previously described the invention provides amongst other things a composition comprising: (i) a hydrogel-forming polymer; (ii) a surfactant; and (iii) a microorganism selected from live, killed, attenuated and inactivated microorganisms, the composition further comprising a feature selected from: (i) at least a portion of the surfactant is in the form of self-assembly structures (e.g. micelles) dispersed in the polymer; and (ii) the composition is capable of releasing self-assembly structures (e.g. micelles) when combined with water. The composition may also comprise an adjuvant. Said water may for example be in the form of gastric, intestinal or colonic fluid or a simulated form of one of them. The invention also provides a composition comprising a (i) hydrogel having dispersed therein self-assembly structure (e.g. micelles) comprising a self-assembly structure-former (e.g. micelle-former), e.g. a compound selected from surfactants comprising a hydrophilic chain and a hydrophobic chain, and (ii) a microorganism selected from live, killed, attenuated and inactivated microorganisms, the drying of such compositions and the dried compositions. The composition may also comprise an adjuvant.

The invention will now be described in detail by reference to the various components which the composition of the invention may comprise. The term "excipient" may be used occasionally to describe all or some of the components other than the active ingredient(s) bearing in mind that some excipients can be active and that some active principles can have excipient character.

If not otherwise stated, ingredients, components, excipients etc of the composition of the invention are suitable for one or more of the intended purposes discussed elsewhere herein e.g. are cosmetically acceptable, environmentally acceptable, pharmaceutically acceptable, acceptable as food additives etc.

For the avoidance of doubt, it is hereby stated that the information disclosed earlier in this specification under the heading "Background" is relevant to the invention and is to be read as part of the disclosure of the invention.

Active Ingredient

The compositions of the invention comprise a microorganism as an active ingredient. In the invention, the microorganism is selected from live, killed, attenuated and inactivated microorganisms. The composition may also comprise an adjuvant as an active ingredient. It is preferred that the invention comprise a bead which comprises, as active ingredients, a microorganism selected from live, killed, attenuated and inactivated microorganisms and an adjuvant.

The microorganism may be a unicellular microorganism, for example it may be selected from bacteria, unicellular fungi and protozoa. The microorganism may be an intestinal pathogen. The microorganism may be a pathogen, e.g. an intestinal pathogen, of a bird or mammal, e.g. human. The microorganism may be a human intestinal pathogen. The microorganism may be a bacterium expressing colonization factor antigen I (CAF/I), and may be a human pathogen expressing CAF/I. The microorganism may comprise a combination of microorganisms, e.g. the microorganisms being as described earlier in this paragraph, for example a combination of microorganisms expressing CAF/I.

The microorganisms may be killed, attenuated or inactivated by any means known to the skilled person including, for example, radioactivity, e.g. non-ionising radiation, ionising radiation, gamma radiation or infrared radiation; ultrasonic vibrations; heat inactivation e.g. moist heating or dry heating; chemical inactivation, e.g. the use of formalin, an alcohol, a phenol, ethylene oxide, propiolactone, ethyleneimine or carbon dioxide; the use of an antibiotic; a physio-chemical method, e.g. steam-formaldehyde; attenuation through a foreign host, e.g. tissue culture, embryonated eggs or live animals, or a combination thereof. It is to be understood that, during the process of killing, attenuating or inactivating, or indeed during the formulation process, the live, killed, attenuated or inactivated microorganisms may be partially fragmented. The skilled person will therefore understand that the use of the term live, killed, attenuated and inactivated microorganisms may refer to a mixture of unfragmented (intact) and fragmented microorganism units; the microorganisms may be intact, although it will be understood that for practical a population of intact microorganisms may include a small proportion of fragmented microorganisms and the term "intact microorganism" is to be construed accordingly.

The microorganism may be formalin-killed. It is expected that formalin-killed microorganisms may be wholly, partly or predominantly fragmented, and the term "killed microorganism" therefore includes within its scope intact dead microorganisms and fragmented dead microorganisms and combinations thereof.

It will be understood that the term "fragmented microorganism" refers to a product obtainable by (having the characteristics of a product obtained by) fragmentation of an intact microorganism, and is therefore to be distinguished from, and does not include, purified or isolated subunits or fragments of microorganisms, as these do not include the residue of (substantially) an entire microorganism.

A hydrophobic active ingredient is determined by the compound being partially or fully soluble in non-aqueous medium and insoluble in aqueous medium. The hydrophobic active ingredient is partially or fully soluble in a non-aqueous environment.

An amphiphilic active ingredient is determined by the presence of both hydrophilic and hydrophobic regions in the compound. The active ingredient is therefore partially or fully soluble in both an aqueous medium and a non-aqueous medium.

In certain embodiments the composition may comprise a hydrophilic active ingredient. In embodiments the composition may comprise a further active ingredient, the further active ingredient being a hydrophilic active ingredient. A hydrophilic active ingredient is partially or fully soluble in an aqueous medium and insoluble in non-aqueous medium.

Compositions of the invention therefore comprise one or more antigens comprising a microorganism selected from live, killed, attenuated and inactivated microorganisms. Additionally, such compositions may comprise an adjuvant, whether a single adjuvant or a combination thereof; for example there may be used as an adjuvant a glycolipid adjuvant such as, for example, α-GalCer or an analogue thereof. "Antigen" is herein defined to include reference to a substance or compound which, when introduced into a non-human animal or a human, will result in the formation of antibodies against the antigen and/or cell-mediated immunity; the antigen content of the compositions of the disclosure comprises or consists of a microorganism, e.g. a single microorganism or a combination of microorganisms, selected from live, killed, attenuated and inactivated microorganisms. As described elsewhere herein, the microorganism is selected from intact and fragmented microorganisms and combinations thereof.

Antigens are commercially available or one of skill in the art is capable of producing them. The one or more antigenic moieties comprised in the vaccine comprise, for example, either a modified-live or killed microorganism (e.g. chemically or heat-killed)

Representative antigens that can be used according to the present invention include, but are not limited to, natural, recombinant or synthetic products selected from viruses, bacteria, fungi, parasites and other infectious agents e.g. prions. Antigens may for example be an infectious agent selected from the following infectious agents: *Entamoeba histolytica*, *Bacillus* including *Bacillus cereus* and *Bacillus subtilis* group, *Blastocystis hominis*, Bovine Spongiform Encephalopathy (BSE) and Creutzfeldt-Jakob Disease (CJD) typical and atypical strains, *Campylobacter* including *Campylobacter jejuni*, *Vibrios* including *Vibrio cholerae*, *Clostridium botulinum*, *Clostridium difficile*, *Clostridium perfringens*, *Cryptosporidium*, *Cyclospora cayetanensis*, *Escherichia coli*, EnteroHemorrhagic *Escherichia Coli* (EHEC), Enterotoxigenic *Escherichia Coli* (ETEC), *Helicobacter pylori*, *Listeria monocytogenes*, *Trichinella spiralis*, *Cryptosporidium* including *Cryptosporidium parvum*, *Cyclospora cayetanensis*, Enteroviruses, *Escherichia coli*—including vero cytotoxin-producing (VTEC) strains and others, *Giardia* including *Giardia duodenalis*, *Giardia lamblia*, *Giardia intestinalis*, Hepatitis A virus, *Listeria monocytogenes*, Marine biotoxins, Noroviruses (Norwalk-like viruses (NLV), small round structured viruses (SRSV)), Rotavirus, Adenoviruses, Sapoviruses, Astroviruses, Polio virus, *Salmonella* including *Salmonella enterica* serovar Enteritidis, *Salmonella typhimurium*, *Salmonella typhi* and *Salmonella paratyphi*, *Shigella* including *Shigella sonnei*, *Shigella boydii*, *Shigella dysenteriae* and *Shigella flexneri*, *Staphylococcus aureus*, Worms, helminthes, *Yersinia* for example *Yersinia enterocolitica* and *Yersinia pseudotuberculosis*, or a combination thereof.

Fungal antigens may for example be *Candida albicans*, *Aspergillus niger*, *Aspergillus fumigatus*, *Cryptococcus neoformans*, *Pneumocystis carinii*, *Coccidioides posadasii*, *Pythium insidiosum*, or a combination thereof.

The compositions may comprise in combination a fungus and a bacterium, and/or two or more strains of the same bacterial species.

In preferred embodiments the composition comprises ETEC as active ingredient. It will be recalled that such compositions may comprise an adjuvant, for example a glycolipid adjuvant such as, for example, α-GalCer or an analogue thereof.

Also to be mentioned are compositions of the invention which comprise *Helicobacter pylori* as active ingredient. It will be recalled that such compositions may comprise an adjuvant, for example a glycolipid adjuvant such as, for example, α-GalCer or an analogue thereof.

The invention therefore includes within its scope a composition comprising:
a matrix comprising a hydrogel-forming polymer; and
comprised in the matrix, (i) a live, killed, attenuated or inactivated bacterium that is selected from enterotoxigenic *Escherichia Coli* (ETEC) and *Helicobacter pylori*, (ii) a surfactant and (iii) an adjuvant.

The invention therefore additionally includes within its scope a composition comprising
a surfactant,
a live, killed, attenuated or inactivated bacterium that is selected from enterotoxigenic *Escherichia Coli* (ETEC) and *Helicobacter pylori*,
an adjuvant, and
a hydrogel-forming polymer in which the surfactant, the microorganism and the adjuvant are included;
and wherein the composition when combined with water is capable of releasing self-assembly structures comprising surfactant and adjuvant.

It will be understood by the reader that the entirety of the disclosure of this specification is applicable to the compositions of the preceding two paragraphs. A composition of either of the two preceding paragraphs in which the bacterium is ETEC may therefore include any one or more features described elsewhere herein as optional (or preferred) features of the invention. A composition of either of the two preceding paragraphs in which the bacterium is *H. pylori* may therefore include any one or more features described elsewhere herein as optional (or preferred) features of the invention.

The invention includes embodiments in which the composition comprises an active ingredient which is an adjuvant selected from the group consisting of: immunostimulant; T-cell activator; macrophage activator; saponins, fractions of saponins, synthesized components of saponins, ISCOMS, muramyl dipeptide and analogues, pluronic polyols, trehalose dimycolate, amine containing compounds, cytokines, lipopolysaccharide derivatives and cationic transfection reagents (e.g. DOTAP). Adjuvants may be chosen for example from the ceramides (e.g. α-galactosylceramide also known as α-GalCer), chitosan, cholera toxin e.g. rCTB (recombinant B subunit of cholera toxin), *E. coli* heat labile enterotoxin e.g. mLT, oligo-nucleotides e.g. oligodeoxynucleotides such as CpG (cytosine phosphate guanine) and ODN1a (deoxy-inosine/deoxy-cytosine) whether or not derivatised, monophospholipid (MPL) e.g. MPLA, BCG, saponins including those derived from the soap bark tree (*Quillaja saponaria*) such as QS21 and QuilA, Poly I:C (polyinosinic:polycytidylic acid or polyinosinic-polycytidylic acid sodium salt), etc, various oils such as, for example, cholesterol-related or cholesterol-derived oils such as, for example, squalene (IUPAC name: (6E,10E,14E,18E)-2,6,10,15,19,23-hexamethyltetracosa-2,6,10,14,18,22-hexaeneoils. Derivatives of all the preceding substances are also included whether or not derivatives are mentioned in a specific context. Substances identified here as adjuvants may have or play other roles in the invention or may play more than one role simultaneously. For example, rCTB may also, in certain embodiments, play the role of an antigen.

As adjuvants may also be mentioned marine derivatives, sponges etc and their derivatives. In general, toll-like receptor ligands may be included as adjuvants and include LPS, lipoproteins, lipopeptides, flagelin, double-stranded RNA, unmethylated CpG islands and various other forms of DNA and RNA classically released by bacteria and viruses. TLR3 and TLR9 ligands are preferred in one embodiment. Substances which bind to the CD1d protein on antigen-presenting cells are particularly contemplated as are mistletoe extracts, particularly detoxified mistletoe extracts. Other adjuvants contemplated include the Nod-like receptor (NLR) ligands described by Wagner et al in PLoS ONE, April 2009, Vol 4, Issue 4, the entirety of which is incorporated herein by reference. Muramyl dipeptide is also envisaged as is KLKL5KLK described by Li et al in DNA and Cell Biology, Vol 27, No. 8, 2008 the entirety of which is incorporated herein by reference. Also contemplated is KLKL5KLK in combination with ODN1a as described by Schellack et al in Vaccine 24 (2006) 5461-5472, the entirety of which is incorporate herein by reference.

Other adjuvants which may be included in the invention include: amorphous aluminium hydroxyphosphate sulfate, aluminium hydroxide, aluminium phosphate, aluminium potassium sulfate and other aluminium compounds, Al hydrogel, cationic liposome-DNA complex JVRS-100IS-COM(s)™, calcium phosphate, Freund's Complete Adjuvant, Freund's Incomplete Adjuvant, CpG DNA, cholera toxin B subunit, liposomes, dimethyldioctadecylammonium bromide, *Escherichia coli* non-toxic B subunit, IL-12, IL-15, interleukin-1β, interleukin-2, interleukin-7, *Escherichia coli* heat-labile toxin LTK63, LTK72, TiterMax Gold, Ribi Adjuvant System (RAS), Montanide ISA 720, Montanide Incomplete Seppic, *Corynebacterium*-derived P40, MPL™, alum and lipopolysaccharide (LPS) derivative Monophosphoryl Lipid A (MPL) combination (AS04), MF59 oil-in-water emulsion with MPL and saponin fraction QS21 (AS02), AS03, Bacterial lipopolysaccharide (LPS), muramyl dipeptide (MDP), CRL1005 copolymer, killed *Corynebacterium parvum*, Montanide ISA 51, *Bordetella pertussis*, cationic liposomes, adamantylamide dipeptide (AdDP), Arlacel A, VSA-3, POLYGEN™, Adjumer™, Algal Glucan, N-(2-deoxy-2-L-leucylamino-β-D-glucopyranosyl)-N-octadecyl-dodecanoylamide hydroacetate, N-acetylglucosaminyl-N-acetylinuramyl-L-Ala-D-isoGlu-L-Ala-dipalmitoxy propylamide (DTP-DPP), stearyl tyrosine, Specol, linear (unbranched) β-D-(2-1) polyfructofuranosyl-α-D-glucose and Al hydrogel (Algammulin), N,N-dioctadecyl-N',N'-bis(2-hydroxyethyl)propanediamine, Calcium Phosphate Gel, CTA1-DD gene fusion protein, DOC/Al(OH)$_3$/mineral carrier complex, γ-Inulin, Gerbu Adjuvant, granulocyte-macrophage colony stimulating factor, N-acetylglucosaminyl-(b1-4)-N-acetylmuramyl-L-alanyl-D-isoglutamine, recombinant hIFN-gamma/Interferon-g, Sclavo peptide, Rehydragel LV, Rehydragel HPA, Loxoribine, MF59, MTP-PE liposomes, murametide, murapalmitine, D-murapalmitine, neuraminidase-galactose oxidase, non-ionic surfactant vesicles (NISV), polymethyl methacrylate, protein cochleates, Stimulon™ QS-21, SPT (Antigen Formulation), Quil-A, 2-[(R)-3-tetradecanoyloxytetradecanoylamino]ethyl 2-deoxy-4-O-phosphono-3-O-[(R)-3-tetradecanoyoxytetradecanoyl]-2-[(R)-3-tetradecanoyoxytetradecanoylamino]-β-D-glucopyranos idetriethylammonium salt (RC529), LTR192G, *E. coli* heat-labile toxin, 1-(2-methypropyl)-1H-imidazo[4,5-c]quinolin-4-amine (Imiquimod), Resiquimod, AF03, Flagellin protein, ISCOMATRIX®, Abisco-100, albumin-heparin microparticles, B7-2 (CD86), dehydroepiandrosterone, immunoliposomes containing antibodies to costimulatory molecules, SAF-1, Sendai proteoliposomes, threonyl muramyl dipeptide (TMDP), Ty-VLPs, Bupivacaine, polyester poly (DL-lactide-co-glycolide), monophosphoryl lipid A (MPL)+squalene, non-toxic mutant E112K of cholera toxin mCT-E112K, Matrix-S.

Preferred adjuvants include the ceramides and other lipid molecules (especially non-ionic lipid molecules) which specifically stimulate natural killer T (NKT) cells. A ceramide is composed of sphingosine and a fatty acid and are found in high concentrations within the cell membrane of cells being one of the component lipids that make up sphingomyelin, one of the major lipids in the lipid bilayer. Ceramide can act as a signaling molecule e.g. regulating the differentiation, proliferation, programmed cell death (PCD), and apoptosis (Type I PCD) of cells. Preferred ceramides include alpha-galactosyl-ceramides including agelasphins and derivatives. A particularly preferred alpha-galactosylceramide is the product known as KRN7000 commercially available from Funakoshi, Japan, and originally synthesised by Kirin Pharmaceuticals, Japan. Derivatives of KRN7000 are also contemplated as components of the composition of the invention and are described in detail by WO 2004/028475 and Dere et al (2008) in Organic Letters, Vol 10, no 20, pp 4641-4644, the entirety of both of which are incorporated herein by reference. The thiolated derivative of alpha-galactosylceramide (in which the glycosidic oxygen atom has been replaced by a sulphur atom) described by Dere et al is particularly preferred as are racemates, enantiomers or diastereoisomers thereof and of closely related derivatives.

In one embodiment, the inclusion in the composition of the invention of more than one adjuvant may aid in the stimulation of a mucosal immune response.

In preferred embodiments the active ingredient is a microorganism and a second active ingredient is an adjuvant. Preferably the adjuvant is an immunostimulant e.g. is a T-cell activator or an antigen-presenting cell activator. A representative example of an adjuvant is α-GalCer.

In certain embodiments the weight ratio of adjuvant:microorganism is from 1:1 to 1:10 and optionally from 1:3 to 1:5, e.g. from 1:1.35 to 1:1.45. The microorganism may consist of one or more unicellular microorganisms. In this embodiment, the ratio of adjuvant to the aggregate amount of unicellular microorganisms (mg dry weight of adjuvant to $10^{10}$ cells) may be from 0.1-100 mg:$10^{10}$ cells, for example 0.1-10 mg:$10^{10}$ cells, e.g. 0.25-5 mg:$10^{10}$ cells, particularly 0.4-5 mg:$10^{10}$ cells.

In certain embodiments, wherein the microorganism consists of one or more unicellular microorganisms, the ratio of surfactant to the aggregate amount of unicellular microorganisms (mg dry weight of surfactant to $10^{10}$ cells) may be from 10-200 mg:$10^{10}$ cells and optionally from 25-125 mg:$10^{10}$ cells, e.g. from 25-150 mg:$10^{10}$ cells, 25-100 mg:$10^{10}$ cells, 50-200 mg:$10^{10}$ cells, 50-100 mg:$10^{10}$ cells or 60-90 mg:$10^{10}$ cells.

In embodiments where any component of the composition are temperature sensitive (e.g. a microorganism, an adjuvant etc.) it is appreciated that methods of manufacture that accommodate temperature labile components (as described below) may be used.

The composition of the invention may be utilized in order to bring antigen into contact with the gut-associated lymphoid tissue (GALT) either directly or after absorption. The composition of the invention is intended, in one embodiment, to allow antigens and/or adjuvants to interact with or facilitate their interaction with T cells in the GALT. In one embodiment, the section of the GI tract where this interaction occurs is the rectum and/or colon. In another embodiment, the section is the jejunum or other site having almost no immune inductive sites. The composition of the invention may be adapted to release the microorganism and adjuvant after the composition has passed through the stomach and particularly in the upper small intestine; the composition may therefore be enteric coated.

The present invention provides compositions and/or formulations comprising the necessary antigenic peptides (including any covalently or non-covalently modified peptides) to be formulated, with or without adjuvants and optionally other ingredients as described elsewhere herein. Such other ingredients e.g. permeability enhancers, along with the composition of the invention being optionally encapsulated (e.g. coated) with a single or multiple layer(s) of (for example) a polymer, with the layers or polymer coatings being modified permit release of the active components at the most appropriate location along the intestine or colon/rectum.

Accordingly, the invention includes a method of inducing an immune response in a mammal, e.g. a human, comprising:
  administering to the mammal a composition of the disclosure which is adapted to release a microorganism selected from live, killed, attenuated and inactivated microorganisms in the GI tract; and/or
  administering to the mammal a composition of the disclosure which further comprises an adjuvant.

As adaptations for release in the colon or rectum may be mentioned by way of example:
  formulating the composition as a suppository
  formulating the composition for oral administration and including release-controlling agents.

As examples of release-controlling agents, the composition may comprise a polymer which is degraded by bacterial enzymes in the colon or which otherwise acts as a barrier until the composition reaches the colon (e.g. which is dissolved or degraded in the conditions of the colon). Retardant polymers which are degraded or eroded during passage down the GI tract may be used and/or pH-independent polymers comprising pore-formers which are dissolved or degraded in the conditions of the colon. The composition may include an enteric polymer to prevent degradation in the stomach such that the composition is exposed to further dissolution, erosion or degradation only when it has entered the intestine. Polymers mentioned in this paragraph may be included in the matrix and/or may form or be comprised in one or more coatings.

As discussed elsewhere herein, pH-independent coating polymers may be used, for example ethylcellulose. The addition, therefore, to an ethylcellulose (e.g. Surelease™) or other pH-independent coating of a second polymer (e.g. a polysaccharide, especially a heteropolysaccharide) which is susceptible to degradation by bacterial enzymes but not by digestive enzymes, e.g. human digestive enzymes, helps ensure that the barrier function of the coating is destroyed by the action of such enzymes in the terminal ileum and/or colon, thereby ensuring release of the actives in the ileum and/or colon. The inclusion of such a bacterial enzyme-degradable polymer in a pH-independent coating, e.g. ethylcellulose, provides flexibility in modulating the amount of polymer added to the beads of the invention in order to achieve optimal dissolution profiles. In general terms, therefore, the disclosure includes formulations as described herein which comprise a coating comprising a combination of a delayed release material, for example an erodible polymer e.g. ethylcellulose, and a polymer susceptible of degradation by bacterial enzymes in the colon, e.g. a polysaccharide and particularly a water-soluble polysaccharide, particularly a pectin. However, even in the case of targeted colonic release, it is not mandatory to combine ethylcellulose or other pH-independent coating polymer with a polymer susceptible to degradation by bacterial enzymes.

Nutrients

The compositions of the invention may further comprise an immune-enhancing nutrient, for example one or more nutrients selected from vitamins A, B (e.g. one or a combination of vitamin B6, vitamin B12, niacin (vitamin B3), pantothenic acid, riboflavin (vitamin B2), thiamin (vitamin B1) and folic acid), vitamin C, vitamin E; carotenoids, e.g. beta-carotene, iron, manganese, selenium and zinc. The composition may comprise a nutrient, e.g. a combination of nutrients, in the matrix (included in the hydrogel-forming polymer); the composition may comprise a nutrient, e.g. a combination of nutrients, in association with the surfactant; the composition may comprise a nutrient, e.g. a combination of nutrients in a coating; the composition may comprise a nutrient (e.g. a combination of nutrients) in each of two or three of the aforesaid locations. Water soluble nutrients may be suitable for inclusion in the matrix (dried aqueous phase) and surfactant-soluble nutrients may be suitable for association with, e.g. inclusion in, the surfactant, but the invention is not limited to these possibilities.

Polymer Matrix

The disclosure includes formulations comprising a surfactant phase and a continuous phase or matrix phase to provide mechanical strength. The continuous phase or matrix phase comprises a hydrogel-forming polymer. Such formulations therefore comprise a polymer matrix.

A hydrogel-forming polymer is a polymer capable of forming a hydrogel. A hydrogel may be described as a solid or semi-solid material, which exhibits no flow when at rest, comprising a network (matrix) of hydrophilic polymer chains that span the volume of an aqueous liquid medium.

The composition may comprise a hydrogel-forming polymer selected from the group consisting of: gelatin; agar; agarose; pectin; carrageenan; chitosan; alginate; starch; xanthan gum; gum Arabic; guar gum; locust bean gum; polyurethane; polyether polyurethane; cellulose; cellulose ester, cellulose acetate, cellulose triacetate; cross-bonded polyvinyl alcohol; polymers and copolymers of acrylic acid, hydroxyalkyl acrylates, hydroxyethyl acrylate, diethylene glycol monoacrylate, 2-hydroxypropylacrylate, 3-hydroxypropyl acrylate; polymers and copolymers of methacrylic acid, hydroxyethyl methacrylate, diethyleneglycol monomethacrylate, 2-hydroxypropyl methacrylate, 3-hydroxypropyl methacrylate, dipropylene glycol monomethylacrylate; vinylpyrrolidone; acrylamide polymers and copolymers, N-methylacrylamide, N-propylacrylamide; methacrylamide polymers and copolymers, N-isopropylmethacrylamide, N-2-hydroxyethylmethacrylamide; and vinyl pyrrolidone; and combinations thereof. In specific embodiments binary or tertiary etc combinations of any of the above substances are foreseen.

The hydrogel-forming polymer may also be referred to as a hydrocolloid i.e. a colloid system wherein the colloid particles are dispersed in water and the quantity of water available allows for the formation of a gel. In embodiments it is preferred to use reversible hydrocolloids preferably thermoreversible hydrocolloids (e.g. agar, agarose, gelatin etc) as opposed to irreversible (single-state) hydrocolloids. Thermoreversible hydrocolloids can exist in a gel and sol state, and alternate between states with the addition or elimination of heat. Gelatin, agar and agarose are thermo-reversible, rehydratable colloids and are particularly preferred. Gelatin derivatives such as, for example, succinated or phthalated gelatins are also contemplated. Thermoreversible hydrocolloids which may be used according to the invention include those derived from natural sources such as, for example, carrageenan (extracted from seaweed), gelatin (extracted from bovine, porcine, fish or vegetal sources), agar (from seaweed), agarose (a polysaccharide obtained from agar) and pectin (extracted from citrus peel, apple and other fruits). A non-animal based hydrocolloid may be preferred for certain applications e.g. administration to vegetarians or to individuals not wishing to ingest animal products for religious or health reasons. In relation to the use of carrageenan, reference is made to US patent application 2006/0029660 A1 (Fonkwe et al), the entirety of which is incorporated herein by reference. The hydrogel-forming polymer may comprise or be a combination of gelatin with one or more other thermoreversible hydrocolloids, e.g. with one or more other of the thermoreversible hydrocolloids just listed. The hydrogel-forming polymer may comprise or be a combination of gelatin with agar; optionally, at least one further thermoreversible hydrocolloid may be included in the combination, for example one just listed.

Thermo-reversible colloids present a benefit over other hydrogel-forming polymers. Gelation or hardening of thermo-reversible colloids occurs by cooling the colloid, e.g. in a liquid cooling bath or by air flow. Gelation of other hydrogel-forming polymers, which is chemically driven, can lead to leakage of the composition contents into the gelation medium as the hardening process can take time to occur. Leakage of the content of the composition may lead to an inaccurate quantity of the active ingredient within the composition. Thermo-reversible colloids are also known as thermo-reversible gels, and it is therefore preferred that the hydrogel former be a thermo-reversible gelling agent.

Another term which may be applied to hydrogel formers which are advantageous is "thermotropic": a thermotropic gelling agent (which the reader will infer is preferred as a hydrogel former used in the invention) is one caused to gel by a change in temperature and such gelling agents are able to gel more rapidly than those whose gelling is chemically induced, e.g. ionotropic gelling agents whose gelling is induced by ions, for example chitosan. In embodiments of the invention, therefore, the hydrogel former is a thermotropic gel-forming polymer or a combination of such polymers.

The manufacture of the composition may require that the hydrogel-forming polymer be present as a solution, which is preferably an aqueous solution. The hydrogel-forming polymer represents between 5% and 50%, preferably between 10% and 30%, still more preferably between 15% and 20% by weight of the aqueous phase during manufacture.

In embodiments the hydrogel-forming polymer is a pharmaceutically acceptable polymer.

In certain embodiments the hydrogel-forming polymer is gelatin. In certain embodiments the hydrogel-forming polymer comprises gelatin.

The hydrogel-forming polymer may optionally comprise sorbitol or glycerine, or a combination thereof, as a plasticiser. In particular one or more plasticisers may be combined with gelatin.

In embodiments in which gelatin is the polymer matrix of the invention, reference is hereby made to "Bloom strength", a measure of the strength of a gel or gelatin developed in 1925 by O. T. Bloom. The test determines the weight (in grams) needed by a probe (normally with a diameter of 0.5 inch) to deflect the surface of the gel 4 mm without breaking it. The result is expressed in Bloom (grades) and usually ranges between 30 and 300 Bloom. To perform the Bloom test on gelatin, a 6.67% gelatin solution is kept for 17-18 hours at 10° C. prior to being tested.

When the hydrogel-forming polymer comprises or is gelatin the bloom strength of the gelatin may be in the range of 125 Bloom to 300 Bloom, 200 Bloom to 300 Bloom and preferably 250 Bloom to 300 Bloom. It should be appreciated that higher bloom strength gelatin can be replaced by lower bloom strength gelatin at higher concentrations.

According to the invention, in embodiments in which the water-soluble polymer matrix material comprises or is gelatin, the gelatin may be sourced by a variety of means. For example, it can be obtained by the partial hydrolysis of collagenous material, such as the skin, white connective tissues, or bones of animals. Type A gelatin is derived mainly from porcine skins by acid processing, and exhibits an isoelectric point between pH 7 and pH 9, while Type B gelatin is derived from alkaline processing of bones and animal (bovine) skins and exhibits an isoelectric point between pH 4.7 and pH 5.2. Type A gelatin is somewhat preferred. Gelatin for use in the invention may also be derived from the skin of cold water fish. Blends of Type A and Type B gelatins can be used in the invention to obtain a gelatin with the requisite viscosity and bloom strength characteristics for bead manufacture.

Lower temperature gelatin (or gelatin derivatives or mixtures of gelatins with melting point reducers) or other polymer matrices able to be solidified at lower temperatures (e.g. sodium alginate) are preferred for example when the active principle to be incorporated in the composition of the invention is temperature-labile or whose activity may be affected by exposure to higher temperatures. It is therefore believed that polymer which comprises or is low temperature gelatin is a preferred matrix polymer in this invention.

According to the invention, in embodiments in which the polymer comprises or is gelatin, the starting gelatin material is preferably modified before manufacture to produce "soft gelatin" by the addition of a plasticizer or softener to the gelatin to adjust the hardness of the composition of the invention. The addition of plasticizer achieves enhanced softness and flexibility as may be desirable to optimise dissolution and/or further processing such as, for example, coating. Useful plasticizers of the present invention for combination with gelatin or another hydrogel-forming polymer include glycerine (1,2,3-propanetriol), D-sorbitol (D-glucitol), sorbitol BP (a non-crystallizing sorbitol solution) or an aqueous solution of D-sorbitol, sorbitans (e.g. Andidriborb 85/70), mannitol, maltitol, gum arabic, triethyl citrate, tri-n-butyl citrate, dibutylsebacate. Other or similar low molecular weight polyols are also contemplated for example ethylene glycol and propylene glycol. Polyethylene glycol and polypropylene glycol may also be used although these are less preferred. Glycerine and D-sorbitol may be obtained from the Sigma Chemical Company, St. Louis, Mo. USA or Roquette, France. Some active agents and excipients included for other functions may act as plasticisers.

Softeners or plasticisers, if utilized, can be ideally incorporated in a proportion rising to 30%, preferably up to 20% and more preferably up to 10% by dry weight of the composition of the invention, even more preferably between 3 and 8%, and most preferably between 4% and 6%.

It is possible within the scope of the invention that the hydrogel-forming polymer comprises a further surfactant, in addition to said surfactant with which any adjuvant is associated, which it will be recalled may be a mixture of surfactant compounds.

Although not essential, the hydrogel-forming polymer may also optionally contain a disintegrant where it is particularly desired to enhance the rate of disintegration of the composition of the invention. Examples of disintegrants which may be included are alginic acid, croscarmellose sodium, crospovidone, low-substituted hydroxypropyl cellulose and sodium starch glycolate.

A crystallisation inhibitor (e.g. approximately 1% by dry weight of the composition) may also be included in the composition of the invention. An example is hydroxy propyl/methyl cellulose (HMC or HPMC, hypromellose etc) which may play other roles such as, for example, emulsifier.

In an alternative preferred embodiment, the polymer matrix is chitosan which can exist in the form of biogels with or without additives as described e.g. in U.S. Pat. No. 4,659,700 (Johnson & Johnson); by Kumar Majeti N. V. Ravi in Reactive and Functional Polymers, 46, 1, 2000; and by Paul et al. in ST. P. Pharma Science, 10, 5, 2000 the entirety of all 3 of which is incorporated herein by reference. Chitosan derivatives e.g. thiolated entities are also contemplated.

The hydrogel-forming polymer may have a low water content, therefore the composition may have a low water content.

In certain embodiments the composition does not comprise compounds containing a disulphide bond. In embodiments the hydrogel-forming polymer does not comprise compounds containing a disulphide bond.

Surfactant

The surfactant may be present as self-assembly structures (e.g. micelles) dispersed within the hydrogel-forming polymer in a "wet" (not yet dried) composition made as an intermediate in the manufacturing process described herein. It is believed also to be present as self-assembly structures (e.g. micelles) in the dried composition but observability of self-assembly structures like micelles or micelle-like structures in the dried composition is not a requirement of the invention. It is mentioned at this point that the presence of a surfactant in a self-assembly structure (e.g. micelle) form does not require that the entire surfactant content of a composition is in this form as it is considered more probable that a portion of the surfactant will be outside the self-assembly structures (e.g. micelles). Thus in the "wet" composition, whether the hydrogel-forming polymer is in the gel state or the sol (liquid) state may comprise the surfactant at a concentration above the critical concentration for formation of self-assembly structures (e.g. micelles) (i.e. above the critical micelle concentration).

With regard to micelles, the diameter of the dispersed micelles is between 0.5 nm and 200 nm, 1 nm and 50 nm, or 5 nm and 25 nm. The size of the micelles may be determined by dynamic light scattering or diffusion NMR techniques known within the art. Although the size of the micelles is given as a diameter this does not imply that the micelles must be purely spherical species only that they may possess some approximately circular dimension.

The surfactant may be a non-ionic surfactant. The surfactant may be a polyoxyethylated surfactant. The surfactant has a hydrophilic head which may be a hydrophilic chain, for example a polyoxyethylene chain or a polyhydroxylated chain.

The surfactant of course has a hydrophobic part and in particular a hydrophobic chain. The hydrophobic chain may be a hydrocarbon chain, for example having at least 6 carbon atoms and optionally at least 10 carbon atoms, and particularly of at least 12 carbon atoms; some hydrocarbon chains have no more than 22 carbon atoms, for example $C_{10}$-$C_{20}$, $C_{12}$-$C_{20}$ or $C_{15}$-$C_{20}$ hydrocarbon chains. It may be an alkyl chain, e.g. having a number of carbon atoms just mentioned. It may be an alkenyl chain comprising one or more carbon-carbon double bonds, e.g. having a number of carbon atoms just mentioned. The surfactant may comprise a hydrocarbon chain, e.g. alkyl chain or alkenyl chain, that is substituted provided that it maintains a hydrophobic characteristic. There may for example be one or two substituents, for example a single substituent, e.g. selected from halogen (e.g. F or Cl), hydroxy, thiol, oxo, nitro, cyano; hydroxy or thiol substituents may be esterified by for example a fatty acid. One class of surfactants comprise a hydrocarbyl moiety monosubstituted by hydroxy; optionally, at least a portion of the hydroxy groups of an aliquot of surfactant, e.g. of the surfactant in a bead, may be esterified by a fatty acid or mono-hydroxy fatty acid as disclosed herein or etherified by a fatty alcohol for example having at least 6 carbon atoms and optionally at least 10 carbon atoms, and particularly of at least 12 carbon atoms; some hydrocarbon chains have no more than 22 carbon atoms, for example $C_{10}$-$C_{20}$, $C_{12}$-$C_{20}$ or $C_{15}$-$C_{20}$ fatty alcohols.

The hydrophobic chain may be part of an esterified fatty acid $R^1$—COOH or of an etherified or esterified fatty alcohol $R^1$—COH where $R^1$ is the hydrophobic chain, e.g. as mentioned in the preceding paragraph. The ester-forming or, as the case may be, ether-forming group will typically comprise a hydrophilic chain. A portion of the fatty acid molecules $R^1$—COOH or fatty alcohol molecules $R^1$—COH may be as the free acid or alcohol and a portion may be esterified or, in the case of fatty alcohols, etherified.

As mentioned, the surfactant may have a hydrophilic chain and may be a non-ionic surfactant, and may satisfy both requirements. The hydrophilic chain may be a poly(ethyleneglycol), also known as poly(oxyethylene) or macrogol. The hydrophilic chain may be of the formula —(O—$CH_2$—$CH_2$)$_n$—OR where n is 5 or 6 to 50 and R is H or alkyl, e.g. ethyl or methyl. The invention includes implementations in which n is from 6 to 40, e.g. from 6 to 35. In some embodiments, n is from 6 to 25 and optionally is from 8 to 25 or from 8 to 15. In other embodiments, n is from 8 to 50 or from 8 to 40, e.g. is from 10 to 50, 10 to 40 or 10 to 35. In a particular embodiment, n is 15. For all hydrophilic chains of the formula —(O—$CH_2$—$CH_2$)$_n$—OR, in one class of embodiments R is H.

The hydrophilic chain may be a polyhydroxylated chain (for example a $C_5$-$C_{20}$ e.g. $C_5$-$C_{10}$ chain), e.g. having a hydroxy group on the carbon atoms of the chain, for example a glucamide.

The surfactant may comprise a combination of a hydrophobic chain as described above and a hydrophilic chain as described above. It may therefore be, or comprise, a macrogol ester of a fatty acid as described herein or a macrogol ether of a fatty alcohol as described herein.

Micelle-forming surfactants comprising a hydrophobic chain and a hydrophilic chain can be selected from the group consisting of: macrogol esters; macrogol ethers; diblock copolymers; triblock copolymers; and amphiphilic polymers.

In certain embodiments of the invention any combinations of the group are included within the invention.

Examples of macrogol esters which are suitable for use in the present invention are macrogol esters of fatty acids having at least 6 carbon atoms and optionally at least 10 carbon atoms, and particularly of at least 12 carbon atoms; some fatty acids have no more than 22 carbon atoms, for example $C_{10}$-$C_{20}$, $C_{12}$-$C_{20}$ or $C_{15}$-$C_{20}$ fatty acids. The fatty acids may be saturated or unsaturated but are in particular saturated. To be mentioned are macrogol 25 cetostearyl ether (Cremophor® A25); macrogol 6 cetostearyl ether (Cremophor® A6); macrogol glycerol ricinoleate 35 (Cremophor® EL); macrogolglycerol hydroxystearate 40 (Cremophor® RH 40); macrogol-15-hydroxystearate (polyoxy)-15-hydroxystearate US Pharmacopoeia and National Formulary, European Pharmacopoeia, e.g. Kolliphor HS 15, previously known as Solutol® HS 15). Examples of macrogol ethers which are suitable for use in the present invention are macrogol ethers of fatty alcohols having at least 6 carbon atoms and optionally at least 10 carbon atoms, and particularly of at least 12 carbon atoms; some fatty alcohols have no more than 22 carbon atoms, for example $C_{10}$-$C_{20}$, $C_{12}$-$C_{20}$ or $C_{15}$-$C_{20}$ fatty alcohols. The fatty alcohols may be saturate or unsaturated but are in one embodiment saturated. Kolliphor® HS 15 is obtained by reacting 15 moles of ethylene oxide with 1 mole of 12-hydroxy stearic acid; the surfactant may therefore be or comprise a surfactant obtainable by (having the characteristics of a surfactant obtained by) reacting 10-25 moles of ethylene oxide with 1 mole of 12-hydroxy stearic acid; the number of moles of ethylene oxide may, from 12-25 and optionally from 15-20, e.g. 15 or 20.

Kolliphor® HS 15 consists of polyglycol mono- and di-esters of 12-hydroxystearic acid and about 30% of free polyethylene glycol. The main components of the ester part have the following chemical structures:

hol poly(ethoxyl)ates also known as polyethoxylated alkyl ethers; poly(ethoxyl)ated fatty acid esters (Myrj or Kolliphor); fatty amide polyethoxylate; fatty amine ethoxylate; alkylphenol ethoxylate; polyethoxylated sorbitan esters (polysorbates); polyethoxylated glycerides; or poly-glycerol esters.

Examples of copolymers, which are suitable for use in the present invention are: pluronics (poloxamers); polyvinylpyrrolidone-polyvinylacetate (Plasdone S630); aminoalkyl methacrylate copolymer (Eudragit EPO); methacrylic acid-methyl methacrylate copolymer (Eudragit S100, L100); polycaprolactone-PEG; polycaprolactone-methoxy-PEG; poly(aspartic acid)-PEG; poly(benzyl-L-glutamate)-PEG; poly(D,L-lactide)methoxy-PEG; poly(benzyl-L-aspartate-PEG; or poly(L-lysine)-PEG In a preferred embodiment the surfactant is a macrogol ester, more preferably a macrogol ester that conforms to the European Pharmacopoeia monograph number 2052 macrogol-15-hydroxystearate, such as Kolliphor® HS 15 marketed by BASF.

Suitable surfactants comprise those which during manufacture combine with the aqueous phase (including hydrogel-forming polymer) in an amount above their CMC to form a clear liquid. Kolliphor® HS 15 is such a surfactant.

In certain embodiments the weight ratio of the surfactant to the microorganism antigen is from 10:1 to 100:1, optionally from 50:1 to 100:1. In some embodiments, the ratio is from 80:1 to 90:1. In particular embodiments, the ratio is from 50:1 to 60:1.

Combinations of Self-Assembly Structure-Forming Compounds

In particular embodiments, the compositions of the invention comprise a combination of self-assembly structure-forming compounds. Such a combination of self-assembly structure-forming compounds may consist of two or more

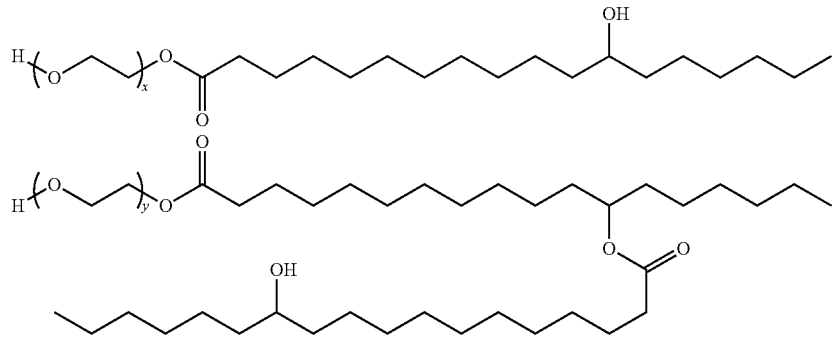

where x and y are integers and a small part of the 12-hydroxy group can be etherified with polyethylene glycol.

Therefore, the surfactant may comprise a mixture of molecules. For example, the surfactant composition used in the manufacturing process may comprise a polyethoxylated (PEGylated) molecule and comprise additionally free polyethoxy (free PEG) compound, or the surfactant composition used in the manufacturing process may comprise a molecule having a polyhydroxylated moiety and comprise additionally free polyhydroxy compound. Amongst the implementations of the invention are those in which the surfactant is, or comprises, a PEGylated fatty acid, e.g. a PEGylated hydroxy fatty acid, in combination with free PEG.

Examples of amphiphilic polymers which are suitable for use in the present invention are: alkyl glucamides; fatty alcohol poly(ethoxyl)ates also known as polyethoxylated alkyl surfactants as mentioned in the preceding section of this specification. Alternatively, a surfactant may be combined with one or more other compounds at least potentially able to form micelles with the surfactant, optionally selected from cationic lipids and glycolipids, amongst others. As an additional option, a composition may comprise a plurality of surfactants as mentioned in the preceding section of this specification and one or more other compounds at least potentially able to form self-assembly structures (e.g. micelles) with the surfactant, optionally selected from cationic lipids and glycolipids, amongst others.

In relation to "mixed self-assembly structures" or "mixed micelles" comprising a combination of self-assembly structure-forming (e.g. micelle-forming) compounds, it is believed, but without being bound by theory, that at least a portion of adjuvant α-GalCer will, together with said self-assembly structure-forming surfactant, act as a self-assembly structure-forming compound in these mixed structures. Other glycolipids and ceramides will behave similarly, it is believed, whether used singly or in combination with another glycolipid or ceramide.

The invention therefore includes compositions as described herein which comprise:

two or more self-assembly structure-forming (e.g. micelle-forming) surfactants, e.g. two or more surfactants having a hydrophobic chain and a hydrophilic chain a compound, e.g. a single compound or two or more compounds, selected from cationic lipids and glycolipids two or more self-assembly structure-forming (e.g. micelle-forming) surfactants and a compound, e.g. a single compound or two or more compounds, selected from cationic lipids and glycolipids.

Further Excipients

The invention foresees incorporation into the composition of one or more of the following substances or categories of substances in addition to the at least one active ingredient, the surfactant and the hydrogel-forming polymer. For example, the composition may contain a protectant such as, for example, a proteolytic enzyme inhibitor or a protector against acid degradation or both (e.g. an alkali for example sodium hydroxide); an adhesive entity such as, for example, a muco- or bio-adhesive; excipients to maximize solubility of active pharmaceutical compound(s); excipients to maximize permeability of the active pharmaceutical compound(s) in the GIT; an oil, for example a medium chain triglyceride composition; a cationic lipid, for example a liposomal transfection reagent; and/or a further surfactant.

The typical excipients for enhancing the permeability of the epithelial barrier include but are not limited to sodium caprate, sodium dodecanoate, sodium palmitate, SNAG, chitosan and derivatives thereof, fatty acids, fatty acid esters, polyethers, bile salts, phospholipids, alkyl polyglucosides, hydroxylase inhibitors, antioxidants (e.g. ascorbic acid) and/or nitric oxide donors, including nitric oxide or carbon dioxide donor groups covalently attached to various active pharmaceutical ingredients. The preceding list is of particular interest to enhance permeability in the ileum.

To enhance permeability in the colon, typical excipients include, but not limited to sodium caprate, sodium dodecanoate, sodium palmitate, SNAG, chitosan and derivatives thereof, fatty acids, fatty acid esters, polyethers, bile salts, phospholipids, alkyl polyglucosides, hydroxylase inhibitors, antioxidants and/or nitric oxide donors, including nitric oxide donor groups covalently attached to various active pharmaceutical ingredients.

The composition may further comprise excipients to enhance the therapeutic potential of active ingredients in the ileum and colon including, but not limited to absorption limiters, essential oils such as, for example, omega 3 oils, natural plant extracts such as, for example, neem, ion-exchange resins, bacteria degradable conjugation linkers such as, for example, azo bonds, polysaccharides such as, for example, amylose, guar gum, pectin, chitosan, inulin, cyclodextrins, chondroitin sulphate, dextrans, guar gum and locust bean gum, nuclear factor kappa B inhibitors, acids such as, for example, fumeric acid, citric acid and others, as well as modifications thereof.

The composition may further comprise an oil, e.g. may contain a single oil or a combination of oils, which may be any pharmaceutically acceptable oil. Oils may include vegetable oils (e.g. neem oil), petrochemical oils, and volatile essential oils. The composition may comprise an oil selected from the group consisting of: poly-unsaturated fatty acids such as, for example, omega-3 oils; medium chain triglycerides; natural triglyceride-based oils which include olive oil, sesame oil, coconut oil, palm kernel oil, preferred include saturated coconut and palm kernel oil-derived caprylic and capric fatty acids and glycerine; other possible oils include linoleoyl macrogolglycerides (polyoxylglycerides) such as, for example, Labrafil (e.g. product number M2125CS by Gattefosse) and caprylocaproyl macrogolglycerides such as, for example, Labrasol by Gattefosse.

As oils may be mentioned liquid lipids, for example selected from medium chain triglyceride (MCT) compositions, the medium chain triglyceride(s) being one or more triglycerides of at least one fatty acid selected from $C_6$-$C_{12}$ fatty acids. It will be understood that commercially available MCT compositions useful in the invention are mixtures derived from natural products and usually or always contain minor amounts of compounds which are not MCTs; the term "medium chain triglyceride composition" is therefore to be interpreted to include such compositions.

The composition of the invention may further comprise a cationic lipid, for example a cationic liposomal transfection reagent. Cationic lipids comprise a hydrophobic moiety, for example an alkyl chain or alkenyl chain having one or more carbon-carbon double bonds, and a cationic group. The hydrophobic group can be, for example, a saturated alkyl chain or an unsaturated alkyl chain. The cationic lipid may be selected from the group consisting of DOTAP (N-[1-(2,3-dioleoyloxy)]-N,N,N-trimethylammonium propane methylsulfate), DOSPER (1,3-dioleoyloxy-2-(6-carboxyspermyl)-propyl amide), DC-Cholesterol HCl (3β-(N-(N',N'-dimethylaminoethane)-carbamoyl)cholesterol hydrochloride), DODAP (1,2-dioleoyl-3-dimethylammonium-propane), DDAB (Dimethyldioctadecylammonium), 12:0 EPC (1,2-dilauroyl-sn-glycero-3-ethylphosphocholine), DOTMA (1,2-di-O-octadecenyl-3-trimethylammonium propane), DOEPC (1,2-dioleoyl-sn-glycero-3-ethylphosphocholine chloride salt), DOG (1,2-dioleoyl-sn-glycerol), DODAP (1,2-dioleoyl-3-dimethylammonium-propane), DOPE (1,2-dioleoyl-sn-glycero-3-phosphoethanolamine), DOPC (1,2-dioleoyl-sn-glycero-3-phosphocholine), DOPG (1,2-dioleoylsn-glycero-3-[phospho-rac-(1-glycerol)] sodium salt), DOSPA (2,3-dioleyloxy-N-[2-(sperminecarboxamido)ethyl]-N-N-dimethyl-1-propanaminium trifluoroacetate), DOTMA (N-[1-(2,3-dioleyloxy)propyl]-N,N,N-trimethylammonium chloride;), DMRIE (1,2-dimyritsyloxypropyl-3-dimethylhydroxyethyl ammonium bromide), DMKE (O,O'-dimyristyl-N-lysyl aspartate), DMKD (O,O'-dimyristyl-N-lysyl glutamate), and DOPS (1,2-dioleoyl-sn-glycero-3-[phospho-l-serine] sodium salt) and combinations thereof.

The composition may further comprise a surfactant which is envisaged to have a primary role other than micelle-formation and selected from the group consisting of: cationic; amphoteric (zwitterionic); anionic surfactants, including perfluoro-octanoate (PFOA or PFO), perfluoro-octanesulfonate (PFOS), sodium dodecyl sulfate (SDS), ammonium lauryl sulfate, and other alkyl sulfate salts, sodium laureth sulfate, also known as sodium lauryl ether sulfate (SLES) and alkyl benzene sulphonate; and non-ionic surfactants including perfluorocarbons, polyoxyethyleneglycol dodecyl ether (e.g. Brij such as, for example, Brij 35), Myrj (e.g. Myrj 49, 52 or 59), Tween 20 or 80 (also known as Polysorbate) (Brij, Myrj and Tween products are available commercially from Croda), poloxamers which are nonionic triblock copolymers composed of a central hydrophobic chain of polyoxypropylene (poly(propylene oxide)) flanked by two hydrophilic chains of polyoxyethylene (poly(ethylene oxide)). A preferred anionic surfactant in the aqueous phase is SDS. Mixtures of further surfactants are also contemplated, e.g. mixtures comprising perfluorocarbons.

In embodiments of the invention, the composition comprises a hydrophilic surfactant which, without being bound by theory, is believed at least partially to partition the aqueous phase (polymer matrix).

Such surfactants intended for such inclusion in the aqueous phase of the inventive composition are preferably readily diffusing or diffusible surfactants to facilitate manufacturing and processing of the composition of the invention. The surfactant may have an HLB of at least 10 and optionally of at least 15, e.g. at least 30 and optionally of 38-42, e.g. 40. Such surfactants can be of any particular type (ionic, non-ionic, zwitterionic) and may comprise as a proportion of dry weight of the composition from 0.1% to 6%, e.g. 0.1% to 5%. 0.1% to 4% or 0.1% to 3%, more preferably in a proportion of at least 1% and in particular between 1.0 and 4.5 or 5%, ideally within or just outside the 2-4% range, for example from 2 to 3% or approximately 2% or approximately 4%.

Unless otherwise stated or required, all percentages and ratios are by weight.

Particular anionic surfactants for inclusion in the aqueous phase include perfluoro-octanoate (PFOA or PFO), perfluoro-octanesulfonate (PFOS), sodium dodecyl sulfate (SDS), ammonium lauryl sulfate, and other alkyl sulfate salts, sodium laureth sulfate, also known as sodium lauryl ether sulfate (SLES) and alkyl benzene sulphonate. A particular class of surfactant comprises sulfate salts. A preferred anionic surfactant in the aqueous phase is SDS. Mixtures of anionic surfactants are also contemplated.

The physical form of the surfactant at the point of introduction into the aqueous phase during preparation plays a role in the ease of manufacture of the composition according to the invention. As such, although liquid surfactants can be employed, it is preferred to utilize a surfactant which is in solid form (e.g. crystalline, granules or powder) at room temperature, particularly when the aqueous phase comprises gelatin.

In general, mixtures of surfactants can be utilised e.g. to achieve optimum long term stability of the composition of the invention with shorter chain surfactants in general facilitating shorter term stability (an aid to processing) and longer chain surfactants facilitating longer term stability (an aid to shelf life). In some embodiments, shorter chain surfactants have up to $C_{10}$ alkyl (e.g. $C_6$-$C_{10}$ alkyl) as the hydrophobic portion of the surfactant whilst longer chain surfactants have $C_{10}$ or higher alkyl (e.g. $C_{10}$-$C_{22}$ alkyl) as the hydrophobic portion of the surfactant. It is envisaged that $C_{10}$ alkyl surfactants may facilitate processing or facilitate prolongation of shelf life, or both, depending on the identity of the other excipients and of the active principle(s). Higher alkyl may in particular implementations of the invention be $C_{11}$-$C_{22}$ or $C_{12}$-$C_{22}$ alkyl, and in some embodiments has a length of no greater than $C_{18}$.

Instead of (or as complement to) the surfactant in the aqueous phase, the invention also contemplates use of surfactant-like emulsifiers (also known as crystallisation inhibitors) such as, for example, HPMC (also known as hypromellose) although their use is generally contemplated in relatively smaller amounts to avoid high viscosity which may constrain processing options.

The composition may further comprise excipients or other active pharmaceutical or other ingredients to enhance systemic bioavailability following absorption in the GIT, such as the small intestine, including efflux pump inhibitors, including, but not limited to PgP pump inhibitors, and metabolism inhibitors, including, but not limited to, cytochrome P450 3A inhibitors.

The composition may further comprise excipients to reduce systemic side effects associated with absorption in the GIT, such as the small intestine, including, but not limited to, antioxidants, such as, for example, curcuminoids, flavanoids or more specifically including curcumin, beta-carotene, α-tocopherol, ascorbate or lazaroid.

The composition may further or separately comprise anti-oxidants (such as, for example, ascorbic acid or BHT—butyl hydroxy toluene) taste-masking or photosensitive components or photoprotective components. Antioxidants may be incorporated in the aqueous phase (e.g. hydrophilic antioxidants) or in the surfactant phase (e.g. hydrophobic antioxidants such as, for example, vitamin E) for example up to 1% by weight, preferably between 0.01 and 0.50% by weight, more preferably between 0.10 to 0.20% by weight.

The composition may further comprise immune-enhancing nutrients such as Vitamins A/B/C/E; Carotenoids/beta-carotene and Iron, Manganese, Selenium, Zinc. Such nutrients may be present in composition, or if the composition has a coating, for example if it is the form of a bead, the nutrients may be included in the coating.

The composition may further or separately include an adhesive to ensure that if desired the bead of the dosage form remain, or remain for longer, in the gastric environment. Beads according to the invention may also comprise materials facilitating or enabling floating or density reduction e.g. as a means of localising beads in desired GI sites. The bead of the dosage form may also have the means to swell and/or aggregate in the stomach or other GI site.

The dosage form of the invention may comprise the excipients disclosed above. In certain embodiments any excipients present in the dosage form may not be contained within the population of the composition of the dosage form.

Shape, Size and Geometry

The composition of the invention can be formed into a limitless number of shapes and sizes. In the section below describing the process for making the composition, various methods are given including pouring or introducing a fluid micelle dispersion into a mould where it hardens or can be caused to harden. Thus the composition can be created in whichever form is desired by creating an appropriate mould (e.g. in the shape of a disc, pill or tablet). However, it is not essential to use a mould. For example, the composition may be formed into a sheet e.g. resulting from pouring a fluid micelle dispersion onto a flat surface where it hardens or can be caused to harden.

Preferably, the composition may be in the form of spheres or spherical-like shapes made as described below. Preferably, the composition of the invention is in the form of substantially spherical, seamless beads. The absence of seams on the bead surface is an advantage e.g. in further processing, for example coating, since it allows more consistent coating, flowability etc. The absence of seams on the beads also enhances consistency of dissolution of the beads.

The preferred size or diameter range of beads according to the invention can be chosen to avoid retention in the stomach upon oral administration of the beads. Larger dosage forms are retained for variable periods in the stomach and pass the pyloric sphincter only with food whereas smaller particles pass the pylorus independently of food. Selection of the appropriate size range (see below) thus makes the prediction of therapeutic effect post-dosing more accurate. Compared to a single large monolithic oral format such as, for example, a traditional compressed pill, a population of beads released into the GI tract (as foreseen by the dosage form of the present invention) permits greater intestinal lumen dispersion so enhancing absorption via exposure to greater epithelial area, prevents irritation (e.g. as otherwise seen with NSAIDs) and achieves greater topical coating (e.g. as may be desired for local drug effect in certain parts of the GI tract for example the colon). Reduction of residence time in the ileo-caecal junction is another potential advantage.

The composition of the invention is preferably monolithic meaning internally (i.e. cross-sectionally) homogeneous, excluding a possible thin skin of matrix material and excluding any coating layers.

The beads provided for by the composition of the present invention generally range in diameter from 0.5 mm to 10 mm with the upper limit preferably 5 mm, e.g. 2.5 mm A particularly convenient upper limit is 2 mm or 1.7 mm. The lower limit can preferably be 1 mm, e.g. 1.2 mm, more preferably from 1.3 mm, most preferably from 1.4 mm. In one embodiment the diameter is from 0.5 to 2.5 mm, for example from 1 mm to 3 mm, 1 mm to 2 mm, 1.2 mm to 3 mm or 1.2 mm to 2 mm. The beads may have a diameter of no more than 2.5 mm, irrespective of their minimum size. The beads may have a diameter of no more than 2 mm, irrespective of their minimum size.

A bead as described herein may have an aspect ratio of no more than 1.5, e.g. of no more than 1.3, for example of no more than 1.2 and, in particular, of from 1.1 to 1.5, 1.1 to 1.3 or, 1.1 to 1.2. A population of beads as described herein, e.g. at least 10 beads, may have an average aspect ratio of no more than 1.5, e.g. of no more than 1.3, for example of no more than 1.2 and, in particular, of from 1 to 1.5, 1 to 1.3 or 1 to 1.2. The aspect ratios mentioned in this paragraph optionally apply to coated beads and optionally apply to uncoated beads. Average aspect ratio is suitably determined for a population of beads, e.g. at least 10 beads, using a particle size analyser, for example an Eyecon™ particle characteriser of Innopharma Labs, Dublin 18, Ireland.

The beads of the disclosure may, therefore, have a size as disclosed above and an aspect ratio of from 1 to 1.5. The beads of the disclosure may have a size as disclosed above and an aspect ratio of no more than 1.3, for example of no more than 1.2 and, in particular, of from 1.1 to 1.5, 1.1 to 1.3 or, 1.1 to 1.2.

Bead size (diameter) may be measured by any suitable technique, for example microscopy, sieving, sedimentation, optical sensing zone method, electrical sensing zone method or laser light scattering. For the purposes of this specification, bead size is measured by analytical sieving in accordance with USP General Test <786> Method I (USP 24-NF 18, (U.S. Pharmacopeial Convention, Rockville, Md., 2000), pp. 1965-1967).

In embodiments, beads of the invention are monodisperse. In other embodiments, beads of the invention are not monodisperse. By "monodisperse" is meant that for a population of beads (e.g. at least 100, more preferably at least 1000) the beads have a coefficient of variation (CV) of their diameters of 35% or less, optionally 25% or less, for example 15% or less, such as e.g. of 10% or less and optionally of 8% or less, e.g. 5% or less. A particular class of polymer beads has a CV of 25% or less. CV when referred to in this specification is defined as 100 times (standard deviation) divided by average where "average" is mean particle diameter and standard deviation is standard deviation in particle size. Such a determination of CV is performable using a sieve.

The invention includes beads having a CV of 35% and a mean diameter of 1 mm to 2 mm, e.g. 1.5 mm. The invention also includes beads having a CV of 20% and a mean diameter of 1 mm to 2 mm, e.g. 1.5 mm, as well as beads having a CV of 10% and a mean diameter of 1 mm to 2 mm, e.g. 1.5 mm. In one class of embodiments, 90% of beads have a diameter of from 0.5 mm to 2.5 mm, e.g. of from 1 mm to 2 mm.

Another possible form of the composition of the invention is as hemispherical beads two of which may optionally be joined at the flat face to create a single bead with two distinct halves, each having a distinct composition, if that is desired, e.g. each containing different active principles or the same active principles but different excipients e.g. to achieve differing permeability, solubilisation or release profiles as between the two hemispheres.

The bead provided for by the composition of the invention, may also be used as a starting point for creation of further e.g. pharmaceutical or nutraceutical forms for example by using the bead as a nonpareil seed on which additional layers of material can be applied as is well known to a person skilled in the art e.g. of pharmaceutical science. The material of the additional layers may comprise the same or different active principle and/or the same or different excipients as are described in this document. Such variants allow differential release of the same or different active principles and facilitate inclusion of multiple fixed-dose combination products as for example discussed in connection with the popularly termed "polypill" which denotes a single pill comprising more than one active principle in a fixed dose combination, an idea of particular relevance to cardiovascular medicine.

The composition of the invention may have a coat of additional material on its outer surface. This coat may be applied in a number of ways, including drug layering, as described more particularly in the section below entitled "coating". In one such embodiment, the composition of the invention comprises an acid e.g. included within the hydrogel-forming polymer matrix or as a liquid core in mini-capsular format and bicarbonate applied as a coat e.g. by drug layering. If the composition has a polymeric coat, e.g. to control release into the colon, the bicarbonate may optionally or additionally be included in or be absent from the coating polymer. This composition is intended to release carbon dioxide in the GI tract e.g. to reduce pain or to reduce inflammation. In a related embodiment, the core or the composition comprises an acid to enhance the solubility of active principles of various pKa (acid dissociation constant) in the small intestine or colon. Alternatively, the core or the composition comprises a base to enhance the solubility of active principles of various pKa in the stomach.

Other Characteristics

The composition of the invention, in certain embodiments, comprises one or more elements, components, excipients, structural features, functional features or other aspects of the prior art described above.

To summarise a limited number of embodiments of the invention, the composition as described above and elsewhere herein may additionally be one or more of the following: substantially water-free, in a gel state, in a solid state, undissolved, non-powdered, formed, shaped, and not in solution.

It is preferable that the composition of the invention is essentially or substantially dry, e.g. contains less than 5%, preferably less than 1% of free water by weight. The beads of the composition are preferably homogeneous although processing conditions may be varied (see below) to achieve for example heterogeneity such as, for example, a harder skin and softer core with less than complete immobilization of the micelles towards the core as opposed to the surface of the bead. Larger forms or shapes of the bead according to the invention may particularly be engineered to embody such heterogeneity.

The low free-water content is a distinguishing feature of certain embodiments of the compositions of the present invention. The free-water content can be measured using thermogravimetic analysis (TGA), for example with commercially available instrumentation, e.g. using a TGA Q 500 of TA Q series instrument. TGA measures changes in weight in relation to a change in temperature. For example, a TGA method can comprise a temperature scan, e.g. from 20 to 400° C. at 20° C. per minute, where the moisture content is obtained from the sample weight loss at about 100 degrees Celsius.

In one embodiment, the micelle dispersion is homogeneously dispersed in the solidified hydrogel-forming polymer with substantial absence of coalescence between adjacent micelles. Thus the micelle dispersion is preferably maintained during solidification.

The composition of the invention generally comprises multiple micelles within a moulded or shaped form which might typically contain many hundreds or thousands of micelles as distinct from a powder which generally derives from micron-sized particles incorporating a single or a small number of micelles often following agglomeration of the micelles during spray-drying. While powder embodiments are not excluded, the composition of the invention, if particulate, preferably comprises particles larger than powder particles such that the composition is in a non-powdered form.

The "solid" composition of the invention (i.e. after solidification and drying of the hydrogel in the processes described below) is suitably such that the constituents readily form micelles in at least one of, e.g. in both of, the surfactant-containing small intestine and the surfactant-limited colon.

In one embodiment, the invention allows for beads or other shaped units having immediate release (IR) characteristics e.g. bearing no coat, enteric-only coat or coat designed to prevent release and/or dissolution of the bead only for a limited time or lacking a retardant in the aqueous phase. In another embodiment, the invention allows for beads having delayed or sustained release (SR) characteristics e.g. bearing a coat (or more than one coat) as described in more detail below, particularly in the section entitled "coating". The invention also provides for an embodiment in which immediate release beads are produced in combination with a Sustained Release or Controlled Release (CR) beads in varying ratios of IR:SR/CR. The immediate release beads can be combined with a Sustained or Controlled release bead component in the following ratios (w/w by potency) e.g. 10% Immediate Release (IR)+90% Sustained (SR)/Controlled Release (CR) minicapsules; 20% IR+80% SR/CR; 30% IR+70% SR/CR; 40% IR+60% SR/CR and 50% IR+50% SR/CR.

In embodiments, the beads or shaped units have an immediate release coat and, between the core made of the micelle-containing composition and the IR coat, a sub-coat to do at least one of the following, amongst others: provide mechanical strength; prevent moisture absorption; modulate release of active agent from the core; stabilise release of active agent from the core (e.g. modulate and stabilise release of active agent from the core).

Manufacturing Processes

The manufacturing processes described herein comprise mixing of liquids. Such mixing processes must be performed at temperatures at which the substances to be mixed in the liquid state are in liquid form. For example, thermoreversible gelling agents must be mixed at a temperature where they are in the liquid state, for example at a temperature of 55-75° C., e.g. 60-70° C. and in particular 65° C. in the case of mixing compositions comprising aqueous gelatin. Kolliphor HS 15 is also to be mixed in the liquid state and is maintained at a temperature of at least 30° C. for that purpose, e.g. of 35-50° C. and in particular 40° C.; where both Kolliphor HS 15 and aqueous gelatin are to be mixed, then a higher temperature, e.g. of 55-75° C., is used at which Kolliphor HS 15 is liquid as well as aqueous gelatin.

Compositions as disclosed herein may be made by mixing materials comprising water, a hydrogel-forming polymer, a surfactant, and an active ingredient(s) to form a self-assembly structure dispersion within an aqueous phase comprising the hydrogel-forming polymer. The hydrogel-forming polymer is then caused or allowed to gel. Suitably, the process includes formulating or processing the aqueous self-assembly structure dispersion into a desired form, e.g. a bead, which forming process may comprise moulding but preferably comprises ejecting the aqueous micelle dispersion through a single orifice nozzle to form droplets which are caused or allowed to pass into a cooling medium, e.g. a water-immiscible cooling liquid, in which the droplets cool to form for e.g. beads.

The mixing of the materials may comprise mixing an aqueous premix (or aqueous phase) and a surfactant premix (or surfactant phase), wherein the aqueous premix comprises water and water-soluble substances whilst the surfactant premix comprises surfactant and surfactant-soluble substances. In some embodiments the aqueous premix comprises at least one water-dispersible substance. In some embodiments the surfactant premix comprises at least one surfactant-dispersible substance.

The aqueous premix comprises, or usually consists of, a solution in water of water-soluble constituents, namely the hydrogel-forming polymer, any water-soluble excipient(s), any hydrophilic active(s). The aqueous premix may include at least a portion of, e.g. all of, the microorganism content of the final composition. The aqueous premix may include at least a portion of, e.g. all of, the adjuvant content of the final composition. The aqueous premix may include a plasticiser, i.e. a water-soluble excipient, as described elsewhere in this specification. The aqueous premix may include a surfactant, e.g. to increase polymer viscosity and improve emulsification and thereby help prevent precipitation of active agent during processing. SDS is an example of such a surfactant. The aqueous phase may include one or more controlled release polymers. In any event, the constituents of the aqueous premix may be agitated for a period of, for example, from 1 hour to 12 hours to form the completed aqueous premix.

The surfactant phase premix comprises a solution in a described surfactant of hydrophobic and amphiphilic constituents. The specification hereby discloses surfactant phase premixes which include at least a portion of the microorganism content and at least a portion of the adjuvant content of the final composition. The surfactant phase premix may include all of the microorganism content and at least a portion of, e.g. all of, the adjuvant content of the final composition. The surfactant phase premix may include a portion of the microorganism content of the final composition, a portion also being included in the aqueous phase premix, and at least a portion of, e.g. all of, the adjuvant content of the final composition. Where the surfactant phase includes a portion of the microorganism content, the portion may be at least 50 wt %, e.g. at least 75 wt %. Where the surfactant phase includes a portion of the adjuvant content, the portion may be at least 50 wt %, e.g. at least 75 wt %. It will be recalled that the surfactant may comprise a hydrophobic chain and a hydrophilic chain. The hydrophobic and amphiphilic constituents, if any, may comprise one or more active ingredients selected from hydrophobic and amphiphilic active ingredients.

The surfactant premix, therefore, will in many cases include a microorganism. Typically, the microorganism will be included directly into the surfactant, for example as a lyophilisate or other dry powder, or the microorganism may be included in the surfactant as an aqueous suspension. The microorganism may be included in the surfactant both as a lyophilisate or other dry powder and as an aqueous suspension. The invention therefore provides a process for manufacturing a surfactant/active premix. A process of the invention comprises mixing (i) a surfactant, and (ii) a microorganism, and optionally (iii) an adjuvant. The surfactant premix may comprise additional substances to the surfactant and any actives. For example it may comprise additional excipients. Such additional excipients may be hydrophobic or amphiphilic, for example they may comprise a water-immiscible material, e.g. an oil. An additional excipient may therefore be a liquid lipid, for example a medium chain triglyceride (MCT) composition, the medium chain triglyceride(s) being one or more triglycerides of at least one fatty acid selected from $C_6$-$C_{12}$ fatty acids. Any one or more active agents may be pre-dissolved in a solvent, e.g. ethanol or an MCT composition, before being combined into the surfactant premix. In some embodiments, the components of the surfactant premix are mixed (or otherwise agitated) for a period of, for example, 10 minutes to 3 hours to form the premix.

The two premixes may be combined and agitated, for example for a period of from 5 mins to an hour, to form a dispersion of self-assembly structures (e.g. micelles) in an aqueous hydrogel-forming polymer, which dispersion may then be further processed to form the final formulation. The two premixes may be combined into the dispersion by agitation in a mixing vessel; they may additionally or alternatively be combined in a continuous flow mixer.

The basic method for making the composition of the invention, therefore, is to mix a fluid form (preferably a solution) of the hydrogel-forming polymer (or mixture of polymers) with the active ingredient(s) and with the surfactant to form a dispersion in the hydrogel formed by the polymer. Taking account of the final composition required (as described elsewhere herein), the surfactant and the fluidic hydrogel-forming polymer may be mixed in a proportion in the range 1:2-5, preferably approximately 1:3 or 1:4. In general, only gentle stirring of the components is required using a magnetic or mechanical system e.g. overhead stirrer as would be familiar to a person skilled in the art to achieve a dispersion of self-assembly structures, e.g. micelles. Continuous stirring is preferred. Any appropriate laboratory stirring apparatus or industrial scale mixer may be utilized for this purpose for example the Magnetic Stirrer (manufactured by Stuart) or Overhead Stirrer (by KNF or Fisher). It is preferred to set up the equipment in such a way as to minimise evaporation of contents such as, for example, water. In one embodiment of the process of the invention, it is preferred to utilise a closed system for stirring in order to achieve this aim.

The invention includes embodiments in which the surfactant phase liquid and water-insoluble constituents are formed into a clear solution which is mixed with the aqueous phase. Both phases may be clear solutions prior to mixing of them to form an emulsion.

In the embodiment where the polymer matrix substantially consists of gelatin with the addition of sorbitol, the aqueous phase of polymer matrix is prepared by adding the appropriate quantities of sorbitol (and surfactant if desired) to water, heating to approximately 60-75° C. until in solution and then adding gelatin although the precise order and timing of addition is not critical. A typical "gelatin solution" comprises 15-25% (preferably 17-18%) gelatin; 75%-85% (preferably 77-82%) of water plus from 1-5% (preferably 1.5 to 3%) sorbitol.

The choice of temperature at which the dispersion is formed depends however on various factors including the temperature lability of the active ingredient and the amount of plasticiser included in the gelatin, the type of gelatin, as well as other factors. Generally however, the gelatin solution (especially in the case of standard or normal gelatin) is maintained at 60° C.-70° C. to maintain it in a fluid state.

The processing temperature can however be reduced to a desirable target temperature e.g. 37° C. by use of lower melting-point gelatin (or gelatin derivatives or mixtures of gelatins with melting point reducers) or other polymer matrix material such as, for example, sodium alginate. Alternatively, temperature-labile active principles may be processed at higher temperatures by using appropriate apparatus or machinery which limits the time during which the temperature-labile active principle is in contact with the higher temperature medium. For example, if gelatin droplets are being formed by machine extrusion and immediately cooled e.g. in a cooling bath, additional appropriate inlet tubing can be used to introduce temperature-sensitive active principle into the fluid gelatin solution (and the mixture can be immediately homogenized) very shortly before ejection from a beading nozzle or other dropletting process such that the duration of exposure of the active principle to the higher temperature gelatin is limited so reducing the degree of any heat-dependent degradation of the active ingredient. This process may use any appropriate device such as, for example, a homogenizer, e.g. a screw homogenizer, in conjunction with an extrusion-type apparatus as described for example in WO 2008/132707 (Sigmoid Pharma) the entirety of which is incorporated herein by reference.

The invention therefore includes processes in which the mixture of the aqueous and surfactant phases is ejected through a single orifice nozzle to form droplets, the hydrogel-forming polymer then being caused or allowed to solidify whereby the droplets form beads, and wherein the hydrogel-forming polymer is a thermotropic polymer or a mixture of thermotropic polymers, the aqueous phase (also called aqueous premix) being at an elevated temperature and the surfactant phase (also called surfactant premix) being at a temperature not exceeding ambient temperature, the two premixes flowing through respective feed lines to a mixing apparatus where the two premixes are mixed, and wherein at least one of the two premixes travels a greater distance through its feed-line than the mixture does in travelling from the mixing apparatus to the nozzle. The two phases may be mixed at a position juxtaposed to the nozzle, e.g. by in-line mixing apparatus juxtaposed to the nozzle.

Generally, where the self-assembly structure-forming surfactant is a liquid there is no need to heat it and the active ingredient is added at room temperature with stirring until clear. It is possible that the surfactant phase may comprise additional components. These other components may include a volatile (or non-volatile) solvent in addition to the surfactant. The surfactant phase may also contain the appropriate amount of active ingredient (if any is added to the surfactant prior to mixing the surfactant with the aqueous phase) to achieve the target proportion of active ingredient as described elsewhere herein and in the examples. In the embodiments where the surfactant is a waxy solid such as, for example, Kolliphor HS 15 it is appropriate to heat the waxy solid, e.g. to above 30° C., to provide a liquid.

The dispersion is formed by addition of the surfactant to the liquid aqueous phase with stirring as described above. The resultant dispersion then has the composition of the solidified beads described above but with liquid water still present.

The active ingredient(s) may optionally be added after mixing the aqueous phase and surfactant.

The self-assembly structure dispersion is then poured or introduced into a mould or other vessel or poured onto sheets or between sheets or delivered dropwise (or extruded) into another fluid such that the polymer matrix-containing aqueous phase, on solidification, takes the form of the mould, vessel, sheet or droplet/bead intended. It is preferred to progress to mould-forming e.g. beading without delay.

Alternatively to moulding, specialised or customised machinery can be employed for example to create the hemispherical beads described above (see section above entitled "Shape, Size and Geometry") in which the invention takes the form of hemispherical beads. It is possible to manufacture a single bead made from joining two such hemispheres (i.e. a single bead having two distinct halves) by using specialist apparatus in which two tubes through which two different emulsions are flowing, normally of circular cross section, are joined shortly before an extrusion point or nozzle (which may be vibrating) into a single dual lumen tube with a flat wall separating the two emulsion flows and which prevents the two emulsions from coming into contact until the point of extrusion. The cross-section of the joined dual-lumen tube up to the point of extrusion therefore appears as two semicircles. In operation, the two hemispherical emulsion flows combine to form a single, substantially spherical, bead on extrusion such that normal droplets are ejected/extruded for solidification.

Solidification can occur in a variety of ways depending on the polymer of the matrix, for example by changing the temperature around the mould, vessel, sheet, droplet/bead etc or by applying a solidification fluid or hardening solution so that the moulded shape is gelled or solidified. In certain embodiments both temperature change and application of a solidifying fluid or hardening solution are employed together or simultaneously.

In the preferred embodiment in which the composition of the invention takes the form of beads, the beads may be formed for example by dropping the self-assembly structure dispersion dropwise into a fluid which effects solidification. Where the viscosity of the emulsion to be beaded reaches a certain point, drop formation becomes more difficult and specialised apparatus is then preferred.

By use of the term "dry", it is not sought to imply that a drying step is necessary to produce the dry micelle dispersion (although this is not excluded) rather that the solid or solidified aqueous external phase is substantially free of water or free of available water. Solidification of the aqueous phase (external phase) may have arisen through various means including chemically (e.g. by cross-linking) or physically (e.g. by cooling or heating). In this respect, the term "aqueous phase" is nevertheless employed in this document to denote the external (continuous) phase of the bead of the invention even though water, in certain embodiments, is largely absent from (or trapped within the cross-linked matrix of) the bead of the invention. The external phase of the composition of the invention is however water-soluble and dissolves in aqueous media. In one embodiment, self-assembly structures are released when the aqueous phase dissolves or is exposed to aqueous media, irrespective of the form adopted by the micelle-forming surfactant in the solid composition.

In the case where solidification can be achieved by raising or reducing temperature, the temperature of the solidification fluid can be adapted to achieve solidification at a desired rate. For example, when gelatin is used as the hydrogel-forming polymer, the solidification fluid is at a lower temperature than the temperature of the emulsion thus causing solidification of the polymer matrix. In this case, the solidification fluid is termed a cooling fluid.

In the case where solidification can be achieved chemically, e.g. by induction of cross-linking on exposure to a component of the solidification fluid, the concentration of such component in the solidification fluid and/or its temperature (or other characteristic or content) can be adjusted to achieve the desired rate and degree of solidification. For example, if alginate is chosen as the polymer matrix, one component of the solidification fluid may be a calcium-containing entity (such as, for example, calcium chloride) able to induce cross-linking of the alginate and consequent solidification. Alternatively, the same or similar calcium-containing entity may be included (e.g. dispersed) in the aqueous phase of the fluid emulsion prior to beading and triggered to induce cross-linking e.g. by applying a higher or lower pH to a solidification fluid into which droplets of emulsion fall dropwise or are introduced. Such electrostatic cross-linking can be varied as to the resulting characteristics of the bead by control of calcium ion availability (concentration) and other physical conditions (notably temperature). The solidification fluid may be a gas (for example air) or a liquid or both. For example, when gelatin is used as the hydrogel-forming polymer matrix, the solidification fluid can be initially gaseous (e.g. droplets passing through cooling air) and then subsequently liquid (e.g. droplets passing into a cooling liquid). The reverse sequence may also be applied while gaseous or liquid cooling fluids alone may also be used. Alternatively, the fluid may be spray-cooled in which the emulsion is sprayed into a cooling gas to effect solidification.

In the case of gelatin or other water-soluble polymer (or polymer mixture) destined to form the immobilization matrix, it is preferred that the solidification fluid be a non-aqueous liquid (such as, for example, medium chain triglycerides, mineral oil or similar preferably with low HLB to ensure minimal wetting) which can conveniently be placed in a bath (cooling bath) to receive the droplets of micelle dispersion as they solidify to form beads. Use of a non-aqueous liquid allows greater flexibility in choice of the temperature at which cooling is conducted.

Where a liquid cooling bath is employed, it is generally maintained at less than 20° C., preferably maintained in the range 5-15° C., more preferably 8-12° C. when standard gelatin is used as the hydrogel-forming polymer. If a triglyceride is chosen as the cooling fluid in the cooling bath, a preferred example is Miglyol 810 from Sasol.

If gelatin or another thermotropic polymer or polymer mixture is selected as the hydrogel-forming polymer matrix, respect for appropriate temperature ranges ensures solidification of the polymer at an appropriate rate to avoid destruction e.g. of tertiary protein structure in the case where the active principle is a protein.

If alginate is selected as the polymer matrix, a typical method of making beads involves dropwise addition of a 3% sodium alginate solution in which oil droplets are dispersed as described above into a 4° C. crosslinking bath containing 0.1 M calcium chloride to produce calcium alginate (this method can be referred to as "diffusion setting" because the calcium is believed to diffuse into the beads to effect cross-linking or setting). Using a syringe pump, or Inotech machine, droplets can be generated or extruded (egg at 5 mL/h if a pump is used) through a sterile needle or other nozzle (described elsewhere herein) which can be vibrating as discussed elsewhere herein. Airflow of between 15 and 20 L/min through 4.5 mm tubing can be applied downwards over the needle to reduce droplet size if desired. Newly formed beads can then be stirred in the calcium chloride bath for up to an hour. If carrageenan is used as the polymer matrix both salt and reduction in temperature e.g. by dropping into cooling oil may be used to obtain solidification.

An alternative approach when using alginate is internal gelation in which the calcium ions are dispersed in the aqueous phase prior to their activation in order to cause gelation of hydrocolloid particles. For example, this can be achieved by the addition of an inactive form of the ion that will cause crosslinking of the alginate, which is then activated by a change in e.g. pH after sufficient dispersion of the ion is complete (see Glicksman, 1983a; Hoefler, 2004 which are both incorporated herein by reference). This approach is particularly useful where rapid gelation is desired and/or where the diffusion approach may lead to loss of API by diffusion thereof into the crosslinking bath.

Where another ionotropic polymer is used than alginate, suitable analogous processes may be used to those described herein in relation to alginate.

Following shape-forming, moulding or beading, the resultant shapes or forms may be washed then dried if appropriate. In the case of beads solidified in a solidification fluid, an optional final step in the method of production described above therefore comprises removal of the solidified beads from the solidification fluid. This may be achieved e.g. by collection in a mesh basket through which the solidification fluid (e.g. medium chain triglycerides) is drained and the beads retained and is preferably conducted without delay e.g. as soon as the beads have formed or within 5, 10, 15, 20, 25 or 30 minutes of their formation. Excess solidification fluid may then be removed using a centrifuge (or other apparatus or machine adapted to remove excess fluid) followed by drying of the beads to remove water or free water and/or removal of some or all of any additional solvent e.g. ethanol or isopropyl alcohol used to dissolve or facilitate dissolution of the active principle in preceding steps optionally followed by washing (e.g. using ethyl acetate) and a subsequent "drying" step to remove excess solvent (e.g. ethyl acetate). Isopropyl alcohol is an example of a solvent which is preferably removed later in processing to reduce residues in the oil or aqueous phase. Drying can be achieved by any suitable process known in the art such as use of a drum drier (e.g. Freund Drum dryer which may be part of the Spherex equipment train if used) with warm air at between 15° C. and 25° C., preferably around 20° C. leading to evaporation or entrainment of the water by the air. Use of gelatin as the polymer matrix (e.g. as principal constituent of the aqueous immobilisation phase) in most cases requires a drying step and for beads this is preferably achieved by drying in air as above described. The resultant composition (the composition of the invention) is essentially dry as described in more detail above.

In terms of the way in which self-assembly structure dispersion droplets may be formed in the first step of the beading process described above, variations of the above described method are possible including introducing droplets into a variety of solidification fluids.

In general, the beads may be generated by the application of surface tension between the liquid dispersion (the mixture of the aqueous and surfactant phases) and an appropriate solidification fluid such as, for example, gas or liquid in order to create the spherical or substantially spherical shape of the ultimate beads.

Alternatively, the beads may be produced through ejection or extrusion of the liquid dispersion through an orifice or nozzle with a certain diameter and optionally subject to selected vibrational frequencies and/or gravitational flow. Examples of machines which may be used are the Freund Spherex, ITAS/Lambo, Globex or Inotech processing equipment. Operation of the Spherex machine manufactured by Freund as may be desired to manufacture beads according to the present invention is described in U.S. Pat. No. 5,882,680 (Freund), the entire contents of which are incorporated herein by reference. It is preferred to select a vibrational frequency in the region of 10-15 RPM although the ultimate choice (and separately the amplitude of vibration selected) depends on the viscosity of the dispersion to be beaded. If the polymer matrix is chosen to solidify at lower temperature, it may be appropriate to maintain the lines to the orifice/nozzle at a certain temperature to maintain the fluidity of the solution.

It will be appreciated, therefore, that the invention includes a process for manufacturing a composition of the invention which comprises: forming an aqueous premix which comprises water and water soluble/dispersible materials (including therefore a hydrogel-forming polymer) and a surfactant premix which comprises surfactant, microorganisms and optionally adjuvant and surfactant soluble/dispersible materials, and combining the two premixes to form a dispersion (disperse phase) within an aqueous phase comprising the hydrogel-forming polymer. The dispersion may then be formed into a shaped unit, for example a bead. More particularly the manufacture of the composition may optionally comprise:

(i) forming an aqueous phase premix comprising, or usually consisting of, a solution in water of water-soluble constituents (e.g. hydrogel-forming polymer, any water-soluble excipient(s), any hydrophilic nutrient(s) as described elsewhere herein);

(ii) forming a surfactant phase premix comprising a mixture in a surfactant of microorganisms, optionally adjuvant and optionally other constituents selected from hydrophobic and amphiphilic constituents (e.g. nutrient(s) as described elsewhere herein);

(iii) mixing the two phases to form a dispersion; and optionally (iv) formulating the dispersion into a bead, e.g. ejecting it through a single orifice nozzle to form droplets which are caused or allowed to fall into a water immiscible cooling liquid in which the droplets cool to form beads, and then separating the beads from the cooling liquid.

Some manufacturing processes comprise steps (A) to (D) below or, alternatively, a manufacturing process may comprise a single one or any combination of steps (A) to (D).

(A) Exemplary Preparation of Aqueous Phase:

Aqueous phase components are added to water, e.g. purified water, under agitation e.g. sonication or stirring. The temperature is gradually increased, for example to 55-75° C. and in particular 65° C., to achieve complete dissolution of the solids. The aqueous phase components include a hydrogel forming polymer, e.g. gelatin or agar and optionally one or more other excipients, for example D-sorbitol (a plasticiser) and optionally one or more active ingredients. Possible aqueous phase components are described elsewhere herein. The aqueous phase components may comprise microorganism cells (whether intact and/or fragmented). There are hereby disclosed processes and their products as described herein in which at least a portion of the microorganism content, and optionally the whole of the microorganism content, is provided in the surfactant phase during manufacture. Nonetheless, the invention does encompass compositions and processes in which the entire microorganism content is in the aqueous phase.

The gelatin may be Type A gelatin. In some less preferred implementations, the gelatin is Type B. The gelatin may have a Bloom strength of 125-300, optionally of 200-300, for example of 250-300, and in particular 275. The components of the aqueous phase may be agitated for a period of, for example, from 1 hour to 12 hours to complete preparation of the aqueous phase (aqueous premix).

(B) Exemplary Preparation of Surfactant Phase:

Surfactant phase components are added to the surfactant under agitation e.g. sonication or stirring. The temperature is gradually increased, for example in the case of the hydrogel-forming polymer being gelatin to, usually, 35-50° C. and in particular 40° C., to achieve complete dissolution of the solids. The components of the surfactant phase are therefore usually agitated e.g. stirred until a clear solution is obtained. The components of the surfactant phase include the surfactant, for example Kolliphor® HS15, and optionally one or more active ingredients. Possible surfactant phase components are described elsewhere herein. In particular, the surfactant phase may include microorganism cells (whether intact and/or fragmented) and usually adjuvant. The components of the surfactant phase may be agitated for a period of, for example, from 10 hour to 3 hours to complete preparation of the surfactant phase (surfactant premix).

At least one of the aqueous phase and the surfactant phase includes at least one active ingredient.

(C) Exemplary Mixing of the Two Phases

The aqueous phase and the surfactant phase are mixed. The two phases may be mixed in a desired weight; for example, the weight ratio of surfactant phase to aqueous phase may be from 1:1 to 1:10, e.g. from 1:1 to 1:6 and optionally from 1:1 to 1:4 and in some cases from 1:3 to 1:4. The resulting solution is agitated, e.g. sonicated or stirred, at an elevated temperature, e.g. in the case of the surfactant being a macrogol-15-hydroxystearate, for example Kolliphor HS 15, or having a melting point similar to that of Kolliphor HS 15 at a temperature of 55-75° C. and in particular 65° C., to achieve a homogeneous micelle dispersion, then the homogenous dispersion is formed into beads. In particular, the homogenous dispersion is ejected through a single orifice nozzle to form droplets which fall into a cooling medium. The nozzle is suitably vibrated to facilitate droplet formation. The nozzle may be vibrated at a frequency of 2-200 Hz and optionally 15-50 Hz.

The cooling medium may for example be air or an oil; the oil is suitably physiologically acceptable as, for example, in the case of medium chain triglycerides e.g. Miglyol 810N. The cooling medium may be at a cooling temperature often of less than 15° C., for example of less than 10° C. but above 0° C. In some embodiments the cooling temperature is 8-10° C. The nozzle size (diameter) is typically from 0.5 to 7.5 mm, e.g. from 0.5 to 5 mm and optionally from 0.5 to 4 mm. In some embodiments, the nozzle diameter is from 1 to 5 mm for example from 2 to 5 mm, and optionally from 3 to 4 mm, and in particular may be 3.4 mm.

The flow rate through a 3.4 mm nozzle is 5 to 35 g/min and optionally 10 to 20 g/min and for nozzles of different sizes may be adjusted suitably for the nozzle area.

(D) Exemplary Processing of Beads

Cooled beads are recovered, for example they may be recovered from cooling oil after a residence time of 15-60 minutes, for example after approximately 30 minutes. Beads recovered from a cooling liquid (e.g. oil) may be centrifuged to eliminate excess cooling liquid, and then dried. Suitably, drying is carried out at room temperature, for example from 15-25° C. and optionally from 20-25° C. The drying may be performed in a drum drier, for example for a period from 6 to 24 hours, e.g. about 12 hours in the case of beads dried at room temperature. The dried beads may be washed, suitably with a volatile non-aqueous liquid at least partially miscible with water, e.g. they may be washed with ethyl acetate. The washed beads may be dried at room temperature, for example from 15-25° C. and optionally from 20-25° C. The drying may be performed in a drum drier, for example for a period from 6 to 48 hours, e.g. of about 24 hours in the case of beads dried at room temperature. Following drying, the beads are passed through a 1 to 10 mm, optionally 2 to 5 mm to remove oversized beads and then through a sieve with a pore size of 0.5 to 9 mm optionally 1 to 4 mm to remove undersized beads.

It can be appreciated that it is possible to recycle the beads that are rejected by the sieving process.

The Spherex machine (and others) may be adapted to make use of a dual concentric lumen nozzle to ensure simultaneous extrusion of two fluids, the fluid in the inner lumen forming a core and the fluid of the outer lumen forming a capsule. The fluid forming the capsule is solidified according to one of the methods described. It may or may not be desirable for the fluid forming the core to be susceptible of solidification to yield a particular embodiment of the composition of the invention.

The above machinery adapted in this way can be used to manufacture the composition of the invention in the form of a capsule in which the core of the composition is filled with a fluid (a gas or a liquid) as described in the section above entitled "Shape, Size and Geometry" (noting that the core, like the capsular material, may be a composition, albeit optionally a distinct composition, according to the invention i.e. susceptible of solidification according to one of the methods described above). A three-lumen nozzle and appropriate tubing may be employed if it is desired to include an intermediate internal layer e.g. internal film layer of non-aqueous material on the inner face of the sphere with the intermediate layer conveniently being solid at room temperature. Thus, in terms of the softness/hardness of successive layers, the composition may for example be described as solid:solid in the case of two layers or solid:solid:solid in the case of 3 layers or liquid/semi-liquid:solid:solid in the case of 3 layers.

The preceding paragraphs describe the formation of uncoated beads. It is a preferred embodiment of the present invention to have coated beads which are described in more detail elsewhere herein. Such coatings may be single or multiple and may be applied in a number of ways (see separate section).

With regard to one of the methods described above (ejection of emulsion through an optionally vibrating nozzle) with two concentric orifices (centre and outer), the outer fluid may form a coat (outside the bead) of e.g. polymeric material (polymeric coating) which may contain an active principle or may impart controlled release characteristics to the bead and the inner layer (core) may be a composition according to the invention. The Spherex machine manufactured by Freund (see U.S. Pat. No. 5,882,680 to Freund) is preferably used (the entire contents of this patent is incorporated herein by reference).

Use of the Spherex machine achieves very high monodispersity. For example, in a typical 100 g, batch 97 g of beads were between 1.4 to 2 mm diameter or between 1 and 2 mm. Desired size ranges can be achieved by methods known in the art for rejecting/screening different sized particles. For example, it is possible to reject/screen out the larger/smaller beads by passing a batch first through e.g. a 2 mm mesh and subsequently through a 1.4 mm mesh.

The 1.4 to 2 mm diameter range is a good size if it is desired to coat the beads (if smaller, the spray of the coating machine may bypass the bead; if too large, the beads may be harder to fluidise which is necessary to achieve consistent coating).

The beads are preferably internally (i.e. cross-sectionally) homogeneous i.e. monolithic although processing conditions may be varied for example by altering the temperature of the fluid emulsion, the solidification fluid and the concentration of components in these fluids and the time allowed for certain processing steps to occur including drying. Although not currently preferred, such variations may be applied in the case of bead manufacture to achieve heterogeneity such as, for example, a harder skin and softer core with less than complete immobilization of oil droplets towards the core as opposed to the surface of the bead. Larger (e.g. non-beaded) forms or shapes of the composition according to the invention may particularly be engineered to embody such heterogeneity. However, it is currently preferred to have internally homogenous compositions according to the invention and within the bead embodiment, this can be favoured by conducting the beading/droptetting using a homogeneous medium e.g. well dispersed micelles. Such homogeneity in the micelle dispersion to be beaded can help avoid the drying conditions affecting symmetry.

The invention further provides a product having the characteristics of a composition obtained as described herein, a product defined in terms of its characteristics being defined by the characteristics of the composition to the exclusion of the method by which it was made.

Coating

A coating may be applied to the beads for targeted, controlled and/or sustained release of the active(s), in particular of the microorganism and optional adjuvant. Application of the appropriate coat may, for example if colonic release is required, allow for say less than 10% of the active principle to be dissolved (in dissolution medium) at 4 hours and then a burst (sudden release) towards a maximum dissolution (approaching 100%) in the subsequent 24 hours. Many alternative target profiles are possible and this example is purely for illustration.

Thus according to one embodiment of the present invention, there is provided a dosage form comprising a population of beads, at least some of which and optionally all of which bear a coat (i.e. are coated) in order to control release of active principle (microorganism and optional adjuvant) from the bead. In one embodiment, the coat is a film and, in another embodiment, it is a membrane. The coat, e.g. film or membrane, may serve to delay release until after the stomach and to protect the microorganism and any adjuvant from gastric fluid; the coat may therefore be an enteric coat. The coat may comprise one or more substances preferably of a polymeric nature (e.g. methacrylates etc; polysaccharides etc as described in more detail below) or combination of more than one such substance, optionally including other excipients or active principles, such as, for example, plasticizers, described e.g. in the sections above on active principles. Preferred plasticizers, if they are used, include hydrophilic plasticizers for example triethyl citrate (TEC) which is particularly preferred when using the Eudragit® family of polymers as coatings as described below. Another preferred plasticiser, described in more detail below in relation to coating with ethyl cellulose, is DBS. Alternative or additional optionally included excipients are glidants. A glidant is a substance that is added to a powder or other medium to improve its flowability. A typical glidant is talc which is preferred when using the Eudragit® family of polymers as coatings.

There may be one or more coatings which comprise active ingredient(s), for example a nutrient (e.g. combination of nutrients) which stimulate the immune system as described elsewhere herein. Such a coating may be an immediate release coating, a delayed release coating or a sustained release coating. An immediate release coating comprising such nutrients and/or other actives may be provided over and/or under a controlled release coating, for example over and/or under an enteric coating or an erodible coating.

In embodiments of the invention the composition comprises a hydrogel-forming polymer and further polymers able to achieve a desired delay (or other change) in the release of the drug and/or poration of the coating and/or exposure of the composition within the coating to allow egress of drug and/or dissolution of the immobilization matrix. In one embodiment, the composition comprises two types of polymers, which are combined into the same polymeric material, or provided as separate coats that are applied to the composition.

Controlled release can be achieved without an additional coating. In this case the polymer matrix comprises a further polymer aimed at a controlled release of an active ingredient. While mixtures of hydrogel-forming polymers are contemplated by the invention, the composition of the present invention in many embodiments comprises a polymer matrix material which is substantially a single material or type of material among those described herein and/or a matrix which can be solidified without inclusion of specific additional polymeric components in the aqueous phase. However, mixtures may be preferred to achieve certain performance characteristics. Thus it may be desired to incorporate certain constraining or retarding substances (retardants) into the water-soluble polymer matrix. In certain embodiments, such incorporation permits a coat (or coating) to be dispensed with. In other embodiments where a constraining or retarding agent is included into the water-soluble polymer matrix, a coat (or coating) may be present and desirable. For example, incorporation of a retarding agent which is insoluble in acid milieu (such as the stomach) is selected to prevent or retard release in the stomach and a coating may not be needed i.e. the composition may be free of a coat/coating. Alternatively, incorporation of a retarding agent which is soluble in acid media may be selected to retard release in the intestine distal to the stomach. Again a coating may not be needed i.e. the composition may be free of a coat/coating. However, the composition according to the invention which incorporates a retarding agent soluble in acid media may optionally be coated e.g. with an acid-resistant polymer to achieve particular advantage. Such a composition is protected from (complete) gastric release (or gastric release is retarded) owing to the effect of the acid-resistant polymer coat. Distal to the stomach, following loss of the coat, the acid-soluble agent retards release because the milieu of the small and large intestine is no longer acid.

Retarding or constraining agents insoluble in acid milieu include polymers whose solubility is pH-dependent i.e. soluble at higher pH. Such polymers are described in detail in the section below entitled "Coating" and such polymers may be used either as coats/coatings or as retarding agents incorporated into the water-soluble polymer matrix. An example of a suitable retarding agent mentioned in the section below entitled "Coating" is HPMCP (hydroxy-propyl-methyl-cellulose-phthalate also known as hypromellose phthalate) which is used to prevent release in the gastric environment since it is soluble above pH 5.5-see that section for other examples of polymers soluble in non-acid (basic) media. HPMCP may also be used as a pore-former. Retarding or constraining agents soluble in acid milieu include polymers whose solubility is pH-dependent i.e. soluble at lower pH. Such polymers include cationic polymers such as for example copolymers based on dimethylaminoethyl methacrylate, butyl methacrylate, and methyl methacrylate. An example of such a cationic co-polymer which may be used according to the invention is Eudragit E PO commercially available from Evonik Industries.

It has previously been stated that the dosage form of the invention may comprise more than one population of beads. Within the coating embodiment, the differences between populations may lie in the coat i.e. two (or more) populations of beads may differ in a number of respects one of which is the coating.

The coat may be applied as described below and may vary as to thickness and density. The amount of coat is defined by the additional weight added to (gained by) the dry composition (e.g. bead) of the invention. Weight gain is preferably in the range 0.1% to 50%, preferably from 1% to 15% of the dry weight of the bead, more preferably in the range 3% to 10% or in the range 5-12% or in the range 8-12%.

The polymeric coating material may comprise methacrylic acid co-polymers, ammonio methacrylate co-polymers, or mixtures thereof. Methacrylic acid co-polymers such as, for example, EUDRAGIT™ S and EUDRAGIT™ L (Evonik) are particularly suitable. These polymers are gastroresistant and enterosoluble polymers. Their polymer films are insoluble in pure water and diluted acids. They may dissolve at higher pHs, depending on their content of carboxylic acid. EUDRAGIT™ S and EUDRAGIT™ L can be used as single components in the polymer coating or in combination in any ratio. By using a combination of the polymers, the polymeric material can exhibit solubility at a variety of pH levels, e.g. between the pHs at which EUDRAGIT™ L and EUDRAGIT™ S are separately soluble. In particular, the coating may be an enteric coating comprising one or more co-polymers described in this paragraph. A particular coating material to be mentioned is Eudragit L 30 D-55.

The trademark "EUDRAGIT" is used hereinafter to refer to methacrylic acid copolymers, in particular those sold under the EUDRAGIT™ by Evonik.

The coating can comprise a polymeric material comprising a major proportion (e.g., greater than 50% of the total polymeric coating content) of at least one pharmaceutically acceptable water-soluble polymer, and optionally a minor proportion (e.g., less than 50% of the total polymeric content) of at least one pharmaceutically acceptable water insoluble polymer. Alternatively, the membrane coating can comprise a polymeric material comprising a major proportion (e.g., greater than 50% of the total polymeric content) of at least one pharmaceutically acceptable water insoluble polymer, and optionally a minor proportion (e.g., less than 50% of the total polymeric content) of at least one pharmaceutically acceptable water-soluble polymer.

Ammonio methacrylate co-polymers such as, for example, EUDRAGIT™ RS and EUDRAGIT™ RL (Evonik) are suitable for use in the present invention. These polymers are insoluble in pure water, dilute acids, buffer solutions, and/or digestive fluids over the entire physiological pH range. The polymers swell in water and digestive fluids independently of pH. In the swollen state, they are then permeable to water and dissolved active agents. The permeability of the polymers depends on the ratio of ethylacrylate (EA), methyl methacrylate (MMA), and trimethylammonioethyl methacrylate chloride (TAMCl) groups in the polymer. For example, those polymers having EA:MMA:TAMCl ratios of 1:2:0.2 (EUDRAGIT™ RL) are more permeable than those with ratios of 1:2:0.1 (EUDRAGIT™ RS). Polymers of EUDRAGIT™ RL are insoluble polymers of high permeability. Polymers of EUDRAGIT™ RS are insoluble films of low permeability. A diffusion-controlled pH-independent polymer in this family is RS 30 D which is a copolymer of ethyl acrylate, methyl methacrylate and a low content of methacrylic acid ester with quaternary ammonium groups present as salts to make the polymer permeable. RS 30 D is available as an aqueous dispersion.

The amino methacrylate co-polymers can be combined in any desired ratio, and the ratio can be modified to modify the rate of drug release. For example, a ratio of EUDRAGIT™ RS:EUDRAGIT™ RL of 90:10 can be used. Alternatively, the ratio of EUDRAGIT™ RS:EUDRAGIT™ RL can be about 100:0 to about 80:20, or about 100:0 to about 90:10, or any ratio in between. In such formulations, the less permeable polymer EUDRAGIT™ RS generally comprises the majority of the polymeric material with the more soluble RL, when it dissolves, permitting gaps to be formed through which solutes can come into contact with the bead allowing pre-dissolved pharmaceutical actives to escape in a controlled manner.

The amino methacrylate co-polymers can be combined with the methacrylic acid co-polymers within the polymeric material in order to achieve the desired delay in the release of the drug and/or poration of the coating and/or exposure of the composition within the coating to allow egress of drug and/or dissolution of the immobilization or water-soluble polymer matrix. Ratios of ammonio methacrylate co-polymer (e.g., EUDRAGIT™ RS) to methacrylic acid co-polymer in the range of about 99:1 to about 20:80 can be used. The two types of polymers can also be combined into the same polymeric material, or provided as separate coats that are applied to the beads.

Eudragit™ FS 30 D is an anionic aqueous-based acrylic polymeric dispersion consisting of methacrylic acid, methyl acrylate, and methyl methacrylate and is pH sensitive. This polymer contains fewer carboxyl groups and thus dissolves at a higher pH (>6.5). The advantage of such a system is that it can be easily manufactured on a large scale in a reasonable processing time using conventional powder layering and fluidized bed coating techniques. A further example is EUDRAGIT® L 30D-55 which is an aqueous dispersion of anionic polymers with methacrylic acid as a functional group. It is available as a 30% aqueous dispersion.

In addition to the EUDRAGIT™ polymers described above, a number of other such copolymers can be used to control drug release. These include methacrylate ester co-polymers such as, for example, the EUDRAGIT™ NE and EUDRAGIT™ NM ranges. Further information on the EUDRAGIT™ polymers can be found in "Chemistry and Application Properties of Polymethacrylate Coating Systems," in Aqueous Polymeric Coatings for Pharmaceutical Dosage Forms, ed. James McGinity, Marcel Dekker Inc., New York, pg 109-114 the entirety of which is incorporated herein by reference.

Several derivatives of hydroxypropyl methylcellulose (HPMC) also exhibit pH dependent solubility and may be used in the invention for coating. These include hydroxypropyl methylcellulose phthalate (HPMCP), which rapidly dissolves in the upper intestinal tract and hydroxypropyl methylcellulose acetate succinate (HPMCAS) in which the presence of ionisable carboxyl groups causes the polymer to solubilize at high pH (>5.5 for the LF grade and >6.8 for the HF grade). These polymers are commercially available from Shin-Etsu Chemical Co. Ltd. As with other polymers described herein as useful for coatings, HPMC and derivatives may be combined with other polymers e.g. EUDRAGIT RL-30 D.

There may be used a polymeric coating substance which is pH-independent in its dissolution profile and/or in its ability to release active principles incorporated in the compositions of the invention. Examples have already been given (e.g., Eudragit RS and RL). Another example of a pH-independent polymeric coating substance is ethylcellulose. It will be understood that an ethylcellulose composition for use in coating a dosage form for may comprise, in addition to ethylcellulose and—in the case of a liquid composition—a liquid vehicle, one or more other components. The other components may serve to modulate the properties of the composition, e.g. stability. The ethylcellulose may be the sole controlled release polymer in such a composition. The ethylcellulose may be in an amount of at least 50%, at least 60%, at least 70%, at least 80%, at least 90% or at least 95% by weight of the dry weight of composition for use in coating a dosage form. Accordingly, an ethylcellulose coating may include other components in addition to the ethylcellulose. The ethylcellulose may be in an amount of at least 50%, at least 60%, at least 70%, at least 80%, at least 90% or at least 95% by weight of the ethylcellulose coating.

A particular ethylcellulose coating composition which may be applied to the compositions of the invention is a dispersion of ethylcellulose in a sub-micron to micron particle size range, e.g. from about 0.1 to 10 microns in size, homogeneously suspended in water with the aid of an emulsification agent, e.g. ammonium oleate. The ethylcellulose dispersion may optionally and preferably contain a plasticizer, for example dibutyl sebacate (DBS) or medium chain triglycerides. Such ethylcellulose dispersions may, for example, be manufactured according to U.S. Pat. No. 4,502,888, which is incorporated herein by reference. One such ethylcellulose dispersion suitable for use in the present invention and available commercially is marketed under the trademark Surelease®, by Colorcon of West Point, Pa. USA. In this marketed product, the ethylcellulose particles are, e.g., blended with oleic acid and a plasticizer, then optionally extruded and melted. The molten plasticized ethylcellulose is then directly emulsified, for example in ammoniated water optionally in a high shear mixing device, e.g. under pressure. Ammonium oleate can be formed in situ, for instance to stabilize and form the dispersion of plasticized ethylcellulose particles. Additional purified water can then be added to achieve the final solids content. See also U.S. Pat. No. 4,123,403, which is incorporated herein by reference.

The trademark "Surelease®" is used hereinafter to refer to ethylcellulose coating materials, for example a dispersion of ethylcellulose in a sub-micron to micron particle size range, e.g. from about 0.1 to 10 microns in size, homogeneously suspended in water with the aid of an emulsification agent, e.g. ammonium oleate. In particular, the trademark "Surelease®" is used herein to refer to the product marketed by Colorcon under the Surelease® trademark.

Surelease® dispersion is an example of a combination of film-forming polymer, plasticizer and stabilizers which may be used as a coating to adjust rates of active principle release with reproducible profiles that are relatively insensitive to pH. The principal means of drug release is by diffusion through the Surelease® dispersion membrane and is directly controlled by film thickness. Use of Surelease® is particularly preferred and it is possible to increase or decrease the quantity of Surelease® applied as coating in order to modify the dissolution of the coated composition. Unless otherwise stipulated, use of the term "Surelease" may apply to Surelease E-7-19020, E-7-19030, E-7-19040 or E-7-19050. E-7-19020 comprises ethylcellulose blended with oleic acid and dibutyl sebacate, then extruded and melted. The molten plasticized ethylcellulose is then directly emulsified in ammoniated water in a high shear mixing device under pressure. Ammonium oleate is formed in situ to stabilize and form the dispersion of plasticized ethylcellulose particles. Additional purified water is then added to achieve the final solids content. E-7-19030 additionally comprises colloidal anhydrous silica dispersed into the material. E-7-19040 is like E-7-19020 except that it comprises medium chain triglycerides instead of dibutyl sebacate. E-7-19050 derives from blending ethylcellulose with oleic acid before melting and extrusion. The molten plasticized ethylcellulose is then directly emulsified in ammoniated water in a high shear mixing device under pressure. Ammonium oleate is formed in situ to stabilize and form the dispersion of plasticized ethylcellulose particles. However, E-7-19040 is preferred.

The invention also contemplates using combinations of Surelease with other coating components, for example sodium alginate, e.g. sodium alginate available under the trade name Nutrateric™.

In addition to the EUDRAGIT™ and Surelease® polymers discussed above, other polymers may be used, in particular enteric, or pH-dependent, polymers. Such polymers can include phthalate, butyrate, succinate, and/or mellitate groups. Such polymers include, but are not limited to, cellulose acetate phthalate, cellulose acetate succinate, cellulose hydrogen phthalate, cellulose acetate trimellitate, hydroxypropyl-methylcellulose phthalate, hydroxypropylmethylcellulose acetate succinate, starch acetate phthalate, amylose acetate phthalate, polyvinyl acetate phthalate, and polyvinyl butyrate phthalate. Additionally, where compatible, any combination of polymer may be blended to provide additional controlled- or targeted-release profiles.

The coating can further comprise at least one soluble excipient to increase the permeability of the polymeric material. Suitably, the at least one soluble excipient is selected from among a soluble polymer, a surfactant, an alkali metal salt, an organic acid, a sugar, and a sugar alcohol. Such soluble excipients include, but are not limited to, polyvinyl pyrrolidone, polyethylene glycol, sodium chloride, surfactants such as, for example, sodium lauryl sulfate and polysorbates, organic acids such as, for example, acetic acid, adipic acid, citric acid, fumaric acid, glutaric acid, malic acid, succinic acid, and tartaric acid, sugars such as, for example, dextrose, fructose, glucose, lactose, and sucrose, sugar alcohols such as, for example, lactitol, maltitol, mannitol, sorbitol, and xylitol, xanthan gum, dextrins, and maltodextrins. In some embodiments, polyvinyl pyrrolidone, mannitol, and/or polyethylene glycol can be used as soluble excipients. The at least one soluble excipient can be used in an amount ranging from about 1% to about 10% by weight, based on the total dry weight of the polymer.

The modifications in the rates of release, such as to create a delay or extension in release, can be achieved in any number of ways. Mechanisms can be dependent or independent of local pH in the intestine, and can also rely on local enzymatic activity to achieve the desired effect. Examples of modified-release formulations are known in the art and are described, for example, in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566 all of which are incorporated herein by reference in their entirety.

The addition to Surelease™ or other pH-independent polymer substance of a second polymer (e.g. a polysaccharide, especially a heteropolysaccharide) which is susceptible to degradation by colonic bacterial enzymes (and optionally or alternatively by pancreatic or other relevant enzymes), provides targeted release of actives to a site or sites where the second polymer is degraded and flexibility in modulating the amount of polymer added to the composition of the invention in order to achieve optimal dissolution profiles.

The invention therefore also provides a coating for compositions (whether of the invention or not) intended to release their active payload in the colon which is a combination of ethylcellulose (preferably formulated with an emulsification agent such as, for example, ammonium oleate and/or a plasticizer such as, for example, dibutyl sebacate or medium chain triglycerides) and a polysaccharide susceptible of degradation by a bacterial enzyme normally found in the colon. Such polysaccharides include chondroitin sulphate, pectin, dextran, guar gum and amylase, chitosan etc and derivatives of any of the foregoing. Chitosan is particularly preferred in connection with obtaining a colon-specific release profile. The invention also includes a composition comprising a combination of ethylcellulose (preferably formulated with an emulsification agent such as, for example, ammonium oleate and/or a plasticizer such as, for example, dibutyl sebacate or medium chain triglycerides) and a polysaccharide susceptible of degradation by a bacterial enzyme normally found in the colon; the composition may include a liquid vehicle, e.g. water.

The use of polysaccharides by themselves for coating purposes has been tried with limited success. Most of the non-starch polysaccharides suffer from the drawback of lacking good film forming properties. Also, they tend to swell in the GI tract and become porous, resulting in the early release of the drug. Even amorphous amylose, which is resistant to degradation by pancreatic alpha amylase but capable of degradation by colonic bacterial enzymes has the disadvantage of swelling in aqueous media although this can be controlled by incorporating insoluble polymers like, ethyl cellulose and acrylates into the amylose film. Amylose however is not water-soluble and although water-soluble polysaccharides are not excluded, the present inventors have found that use of a water-soluble polysaccharide (WSP) susceptible of bacterial enzymic degradation brings particularly advantageous results when used as a coating in accordance with this embodiment of the present invention. A particularly preferred polysaccharide in this embodiment of the present invention is pectin. Various kinds of pectin may be used including pectin of different grades available i.e. with differing degrees of methylation (DM), i.e. percentage of carbonyl groups esterified with methanol, for example pectins with a DM of more than 50%, known as High Methoxy (HM) Pectins or Low Methoxy (LM) pectins, or a pectin combination comprising an HM pectin and an LM pectin. It is also possible in this embodiment to use pectins having various degrees of acetylation (DAc). Taken together, the DM and DAc or the degree of substitution is known as Degree of Esterification (DE). Pectins of various DE's may be used according to the invention. As an alternative to pectin, sodium alginate may be used as a polysaccharide according to an embodiment of the invention. However, other embodiments may conveniently include amylose and/or starch which contains amylose. Various grades of starch, containing different percentages of amylose may be used including for example Hylon V (National Starch Food Innovation) which has an amylose percentage of 56% or Hylon VII which has an amylose percentage of 70%. The remaining percentage is amylopectin. The polysaccharides pectin, amylose and sodium alginate are particularly preferred for achieving colon delivery i.e. for compositions intended to release active principles in the colon.

It has been found that pectin can act as a former of pores in the coating otherwise provided by ethylcellulose (preferably Surelease). By "pores" is not meant shaft-like holes from the surface to the core of the composition, rather areas of weakness or absence of coating occurring stochastically on and within the coating of the invention.

Pore formers have been described before in connection with Surelease (see e.g. US 2005/0220878) but in relation to "gastro-insoluble" substances such as, for example, alginate.

According to a particular embodiment of the invention, where the water-soluble polysaccharide (WSP) is pectin, the proportion of Surelease™ to pectin is ideally in the range 90:10 to 99:1, preferably, 95:5 to 99:1, more preferably 98:2 to 99:1.

In this particularly preferred combination (Surelease™+ WSP e.g. pectin) the weight gain and ratio between Surelease™ and WSP can be varied to refine the behaviour of the coating and the composition of the invention when it bears such a coat. Thus to the inventors/applicant's surprise, the advantages of this preferred combination of coating polymers were further pronounced by selecting a weight gain in the range 0 to 30% (preferably 5 to 10%) and a Surelease to pectin ratio in the range 95:5 to 99.5:0.5 preferably 97:3 to 99:1 inclusive. Particularly favoured weight gains using Surelease are those in the range 5-12% or in the range 8-12%.

Although the focus above has been on extending and/or sustaining release of active principles from compositions according to the invention, also contemplated are uncoated or simple enteric coated compositions providing early, small intestinal active ingredient release with sufficient enteric coating merely to protect the composition from dissolution in the stomach.

It is preferred to dry the composition of the invention before they are coated with a suitable polymeric coat (as described in more detail above/below). It is also preferred, in certain embodiments to apply a first coat before applying a second. In general the first coat and the second coat may be of the same or different materials and be chosen from any of the classes of coating material described herein. In specific embodiments, the first coat optionally protects the core (e.g. bead) from interaction with the second coat and/or prevents leaching of composition contents into the second coat. For example, the first coat may comprise or be hypromellose, e.g. it may be made of a mixture of hypromellose, titanium dioxide and polyethylene glycol; the first coat may comprise at least 50 wt % hypromellose and optionally at least 75 wt % hypromellose, e.g. at least 80 wt % or at least 85 wt % or 90 wt % hypromellose. The coating material used to form the first coat may therefore comprise a dry weight percentage of hypromellose mentioned in the preceding sentence. The second (outer) coat may be an enteric coating as described above or comprise a mixture of polymers including a polymer degradable by bacterial or other enzymes, for example be made of the Surelease-pectin mixture described above. If it is desired for the first coat to use a mixture of hypromellose, titanium dioxide and polyethylene glycol, commercial products corresponding to such mixtures are available including Opadry White, a product commercialised by Colorcon. More generally, there may be mentioned various products commercialised under the trade name Opadry and Opadry II. Further nonlimiting examples include Opadry YS-1-7706-G white, Opadry Yellow 03B92357, Opadry Blue 03B90842). These compositions are available as dry film coating compositions that can be diluted in water shortly before use. Opadry and Opadry II formulations comprise a cellulosic film forming polymer (e.g., HPMC and/or HPC), and may contain polydextrose, maltodextrin, a plasticizer (e.g., triacetin, polyethylene glycol), polysorbate 80, a colorant (e.g., titanium dioxide, one or more dyes or lakes), and/or other suitable film-forming polymers (e.g., acrylate-methacrylate copolymers). Suitable OPADRY or OPADRY II formulations may comprise a plasticizer and one or more of maltodextrin, and polydextrose (including but not limited to a) triacetin and polydextrose or maltodextrin or lactose, or b) polyethylene glycol and polydextrose or maltodextrin). Particularly preferred commercial products are Opadry White (HPMC/HPC-based) and Opadry II White (PVA/PEG-based). Alternative (non-Opadry) products for initial protective coats include polyvinyl alcohol-polyethylene glycol graft copolymers such as is available commercially under the name Kollicoat IR and methyl methacrylate ammonium-based copolymers such as are available commercially under the name Eudragit E. Another preferred example is low molecular weight HPMC. The optional inner coat is applied in the same manner as is the outer (or sole) coat (or coating layer).

The coating process can be carried out by any suitable means such as, for example, by use of a coating machine which applies a solution of a polymer coat (as described above in particular) to the composition. Polymers for coating are either provided by the manufacturer in ready-made solutions for direct use or can be made up before use following manufacturers' instructions.

Appropriate coating machines are known to persons skilled in the art and include, for example, a perforated pan or fluidized-based system for example the GLATT, Vector (e.g. CF 360 EX), ACCELACOTA, Diosna, O'Hara and/or HICOATER processing equipment. To be mentioned is the MFL/01 Fluid Bed Coater (Freund) used in the "Bottom Spray" configuration.

Typical coating conditions are as follows:

| Process Parameter | Values |
| --- | --- |
| Fluidising airflow (m3/h) | 20-60 (preferably 30-60) |
| Inlet air temperature (° C.) | 20-65 |
| Exhaust air temperature (° C.) | 20-42 |
| Product temperature (° C.) | 20-42 |
| Atomizing air pressure (bar) | Up to 1.4 e.g. 0.8-1.2 |
| Spray rate (g/min) | 2-10 and 3-25 RPM |

The compositions of the invention may be coated with active (nutrient and/or drug) layers using methods conventional in the art of pharmaceutical science (such as for example using coating machines as just described) to produce a composition having one or more layer(s), each layer containing one or more active nutrient, pharmaceutical or other ingredient/excipient as described elsewhere herein. Drug layering means the deposition of at least one or successive layers of drug entities from solution, suspension or dry powder on nuclei e.g. beads as described herein. The active ingredient optionally may be free of excipients or in combination with one or more excipients.

Drug layering includes solution/suspension layering, powder layering and powder drug layering. In solution/suspension layering, drug particles are dissolved or suspended in a binding liquid. In powder layering, complete dissolution does not occur, due to low liquid saturation, irrespective of the solubility of the active agent in the binding liquid. In powder drug layering, a binder solution is first sprayed onto previously prepared seeds e.g. beads as described herein, followed by the addition of powder. Conventional pan coaters may be used as described above for polymer coating although modified forms of pan coaters are preferred including fluidised-bed and centrifugal rotary granulators. Examples of suitable granulators include the Rotor granulator. (Glatt), the Rotor-processor (Aeromatic), the Spir-a-Flow (Freund) and the CF-granulator (Freund).

Further examples of drug layering techniques which may be applied to compositions of the invention and/or incorporated in manufacturing methods of the invention are dry coating as described by Luo et al (International Journal of Pharmaceuticals, 358, (2008), page 16-22). Luo et al describe a number of dry coating methods suitable for use in the present invention: electrostatic-dry coating; plasticiser-dry-coating; heat-dry-coating; and plasticizer-electrostatic-heat-dry-coating. Heat-dry-coating uses heat, and the resulting partially melted surface of the powder particles, as the sole binding force. The coating process is achieved by spreading the coating material comprising active ingredient onto the beads in a spheroniser. The coating materials are spread onto the beads by for example a screw powered feeder. The coating material is heated by any means known in the art (e.g. with an infra red lamp). This technique can be used with neat coating material or with a coating material pre dosed with a plasticiser.

In certain embodiments the drug layering material comprises an active ingredient, e.g. nutrient, and a surfactant, in particular a surfactant as described herein as one useful for forming self-assembly structures and optionally a surfactant the same as the self-assembly structures-forming surfactant combined with the hydrogel-forming polymer. The surfactant used in drug layering is conveniently a waxy surfactant solid at room temperature (in particular solid at 25° C. and desirably solid at 30° C.). Such drug layering may be carried out by the solution/suspension or solid method as detailed above. The drug layering may be achieved following the techniques described by Luo et al. in International Journal of Pharmaceuticals, 358, (2008), page 16-22. The surfactant may be selected from those disclosed above, therefore, for example it may be a macrogol ester, e.g. of a fatty acid, and particularly macrogol-15-hydroxystearate, and more specifically Kolliphor HS 15. In a representative example, compositions (particularly beads) of the invention are layered with an active ingredient and macrogol-15-hydroxystearate; the invention therefore includes compositions having one or more layers which include at least one layer comprising a surfactant, e.g. macrogol-15-hydroxystearate, and a drug. In certain embodiments the macrogol-15-hydroxystearate or other surfactant is layered onto the beads using the heat-dry-coating technique described above. The surfactant which is incorporated in said at least one layer may be the same as, or sometimes different from, the surfactant which forms the self-assembly structures.

The use of beads of the invention as seeds for drug layering is superior to using traditional non-pareils as initial substrates in the preparation of pellets by a drug layering process. One reason is the optimal size of the beads of the current invention. Another reason is that sucrose, the main component of traditional non-pareils, has well-known drawbacks including harmful effects on diabetics and potential cariogenicity. According to the prior art, microcrystalline cellulose (MCC) has also been tested as a substrate for drug layering although the inventors/applicants are not aware of successful use of MCC for the preparation of initial cores/beads in a centrifugal granulating process as may be used in embodiments of the present invention. Thus in one embodiment, the invention provides a process for the manufacture of drug-coated pellets comprising using the beads described herein as seeds or as non-pareils (i.e. instead of non-pareils) on which the drug is coated. In a related embodiment, a composition of the invention comprises a bead of the disclosure coated with one or more drug layers. Another embodiment is a process of enhancing the solubility of poorly water-soluble active principles by using one or more of the above described methods of drug layering, including spray-drying-based processes. The polymeric coat, described in detail above, may or may not be applied to a drug-layered bead. However, if desired, it may be applied after such drug layering. In applying a drug layer, the drug to be layered onto the bead may optionally first be admixed with appropriate excipients such as, for example, binders as described elsewhere herein. A particularly preferred binder in this context is polyvinyl pyrrolidone (also spelt polyvinylpyrrolidone and also known as PVP or povidone). PVPs of various K-values may be used. The K-value of PVP is a function of its average molecular weight, the degree of polymerization, and the intrinsic viscosity. It is particularly preferred to use PVP K-32. Up to 5% of the dry weight of the composition of the invention in this embodiment may be made up of such binders. Approximately 1% or less is preferred. Other suitable binders which may be used in drug-layering include gelatin, carboxymethyl cellulose, hydroxypropyl methylcellulose and hydrolysed starches e.g. maltodextrins. Compositions embodying drug layering may also optionally be coated with a polymer coating, or include a polymer layer, to control release as described more generally above including the option to include the same or a different active principle in this polymer coat.

The invention therefore includes a layered bead comprising:

a core comprising, or consisting of, a hydrogel-forming polymer matrix material in which are dispersed (i) micelles and/or pro-micelles, and (ii) an active ingredient comprising an antigen selected from live, killed, attenuated and inactivated microorganisms; and a layer surrounding the core and comprising an active ingredient, which may be the same as or different from the active ingredient comprised in the core, the active ingredient layer optionally also having controlled release properties or other functionality.

The core may additionally comprise an adjuvant. Any adjuvant and the antigen may be included in the micelles and/or promicelles or be included in the polymer matrix, or be included in both.

The layered bead may have a plurality of layers, e.g. 2, 3, 4 or 5 layers, comprising an active ingredient, wherein the active ingredient of each layer is selected independently from the active ingredient of each other layer. In one embodiment, each layer comprises the same active ingredient as each other layer; in another embodiment, no two layers comprise the same active ingredient. The term "active ingredient" in this paragraph embraces both a single active entity and a combination of active entities. The layered bead may comprise one or more polymer layers, to control release as described more generally above. Such a polymer layer may contain an active ingredient and therefore constitute a drug layer as well as a release control layer. Alternatively, a polymer layer may be free of active ingredient. A polymer layer, whether or not it contains an active ingredient, may be located between the core and a drug layer outside the polymer layer, or between two drug layers, or may form an outer layer.

The invention therefore includes a layered bead comprising a core comprising, or consisting of, a matrix comprising a hydrogel-forming polymer; and comprised in the matrix, a microorganism selected from live, killed, attenuated and inactivated microorganisms, a surfactant and an adjuvant;

an active ingredient layer surrounding the core and comprising an active ingredient, which may be the same as or different from the active principle comprised in the core, the active ingredient layer optionally also having controlled release properties or other functionality; and a polymer layer free of active ingredient.

The polymer layer may be located between the core and the active principle layer. The polymer layer may be located externally of the active principle layer. The layered bead may comprise a plurality of active principle layers and, additionally or alternatively, it may comprise a plurality of polymer layers. In some embodiments, there is at least one active principle layer which comprises a release-controlling polymer. In some embodiments, the outermost layer comprises a release-controlling polymer, which may contain an active ingredient or, in another implementation, be free of active principle.

The optionally coated beads of the invention may be formulated directly following their manufacture in the ways described above. In an alternative embodiment, it may be desired to impart different properties to the beads and/or to a final dosage form. One way of achieving this according to the invention is through granulation e.g. to improve the flow of powder mixtures of beads with other components as e.g. described above in relation to binders. Granules of intact or broken beads may be obtained by adding liquids (e.g. binder or solvent solutions) and effecting a granulating step as described in the prior art. Larger quantities of granulating liquid produce a narrower particle size range and coarser and harder granules, i.e. the proportion of fine granulate particles decreases. The optimal quantity of liquid needed to get a given particle size may be chosen in order to minimise batch-to-batch variations. According to this embodiment, wet granulation is used to improve flow, compressibility, bio-availability, homogeneity, electrostatic properties, and stability of the composition of the invention presented as a solid dosage form. The particle size of the granulate is determined by the quantity and feeding rate of granulating liquid. Wet granulation may be used to improve flow, compressibility, bio-availability, and homogeneity of low dose blends, electrostatic properties of powders, and stability of dosage forms. A wet granulation process according to this embodiment may employ low or high shear mixing devices in which a low viscosity liquid (preferably water) is added to a powder blend containing binder previously dry mixed with the rest of the formulation including beads. Alternative granulation approaches which may be utilized include high-shear, extrusion and conventional wet granulation.

Dosage Forms

In a further aspect, the present invention provides for a dosage form comprising a population of beads of the invention. The bead of the dosage form comprises a hydrogel-forming polymer, a surfactant, and an active ingredient. The beads of the dosage form may optionally be coated (as described above). In certain embodiments the dosage form may comprise at least two populations of beads.

Where the bead of the dosage form comprises an active ingredient, which is an active pharmaceutical ingredient the dosage form is suitable for pharmaceutical use.

The dosage form is obtainable by preparing a bead comprising a hydrogel-forming polymer, a surfactant in the form of micelles dispersed in the polymer and an active ingredient. Optionally, the bead is coated; the optional coating may be formulated in such a way as to provide a known or desired release profile in the gastrointestinal tract (GIT). A population of beads is then formulated into a suitable single unit dosage form (as described below) by procedures known to those skilled in the art to produce the dosage form. The dosage form may be further processed (e.g. by coating) to allow a modified release rate of the active ingredient in the GIT.

In certain embodiments the dosage form comprises a population of beads of the invention in a unit dosage form suitable for administration, for example to a human or animal. The unit dosage form chosen from a capsule, a tablet, a sprinkle, a sachet, a suppository, a pessary or other suitable unit dosage form.

In embodiments the dosage form comprising a population of beads may be presented in a single unit dosage form e.g. contained in a single hard gel capsule which releases the beads e.g. in the stomach. Alternatively the beads may be presented in a sachet or other container which permits the beads to be sprinkled onto food or into a drink or to be administered via a feeding tube for example a naso-gastric tube or a duodenal feeding tube. Alternatively, the beads may be administered as a tablet for example if a population of beads is compressed into a single tablet as described below. Alternatively, the beads may be filled e.g. compressed into a specialist bottle cap or otherwise fill a space in a specialised bottle cap or other element of a sealed container (or container to be sealed) such that e.g. on twisting the bottle cap, the beads are released into a fluid or other contents of the bottle or vial such that the beads are dispersed (or dissolve) with or without agitation in such contents. An example is the Smart Delivery Cap manufactured by Humana Pharma International (HPI) S.p.A, Milan, Italy.

The dosage form may be formulated in such a way so that the beads of the invention can be further developed to create a larger mass of beads e.g. via compression (with appropriate oil or powder-based binder and/or filler known to persons skilled in the art of pharmaceutical formulation and with the option of including additional quantities of the same API as in the composition of the invention or a different API a preferred example being where the composition of the invention takes the form of beads which comprise immediate or controlled release cyclosporine and the binder or filler comprises MMF, mycophenolate mofetil, an immunosuppressant) of a plurality of beads which disintegrate at a different rate in different conditions than a unitary moulded form of the same shape. The larger (e.g. compressed) mass may itself take a variety of shapes including pill shapes, tablet shapes, capsule shapes etc. A particular problem which this version of the bead embodiment solves is the "dead space" (above the settled particulate contents) and/or "void space" (between the particulate content elements) typically found in hard gel capsules filled with powders or pellets. In such pellet- or powder-filled capsules with dead/void space, a patient is required to swallow a larger capsule than would be necessary if the capsules contained no such dead space. The beads of this embodiment of the invention may readily be compressed into a capsule to adopt the inner form of whichever capsule or shell may be desired leaving much reduced, e.g. essentially no, dead/void space. Alternatively the dead or void space can be used to advantage by suspending beads in a vehicle such as, for example, an oil which may be inert or may have functional properties such as, for example, permeability enhancement or enhanced dissolution or may comprise an active ingredient being the same or different from any active ingredients in the bead. For example, hard gelatin capsules may be filled with a liquid medium combined with uncoated and/or coated beads. The liquid medium may be one or more of the surfactant phase constituents described herein or it may be one or more surfactants. Particularly preferred but non-limiting examples are corn oil, sorbitane trioleate (sold under the trade mark SPAN 85), propylene glycol dicaprylocaprate (sold under the trade mark Labrafac), 2-(2-ethoxyethoxy)ethanol (sold under the trade mark Trancutol P) and polysorbate 80 (sold under the trade mark Tween 80). An example of a liquid medium which may be used in this embodiment and which contains an active principle is the commercially available cyclosporin pre-microemulstion Neoral™. It is particularly preferred to formulate beads according to the invention in Neoral and to fill a hard gel capsule.

The beads so-presented may be of a single type (or population) or may be of multiple types (or populations) differing between populations in relation to one or more features described herein e.g. different active ingredient or different excipients or different physical geometry, coated, multiply coated, uncoated etc.

In a representative embodiment the bead of the dosage form is formed by preforming a self-assembly structure dispersion by mixing together at least the following materials: a hydrogel-forming polymer; a surfactant; and a microorganism selected from live, killed, attenuated and inactivated microorganisms and optionally additionally mixing together therewith an adjuvant. The dispersion is immobilized within the solidified bead by ejection from a single orifice nozzle into a suitable cooling liquid. Following removal of the drying liquid and any optional coating, the bead is filled into a gelatin capsule suitable for pharmaceutical use.

In some embodiments the dosage form has been appropriately formulated in such a way as to release the one or more active ingredients at a specified point in the GIT e.g. the colon.

Where the dosage form comprises at least two populations of beads at least some of the beads (e.g. a first population) may comprise an active ingredient (or more than one) and other beads (e.g. a second population) may comprise an active ingredient (or more than one). At least one population comprises an active ingredient which comprises an antigen selected from live, killed, attenuated and inactivated microorganisms and optionally comprises an adjuvant. One population may be free of active principles or include "deactivating" principles e.g. enzyme or toxin sequesters or include active excipients, such as, for example, permeability enhancers, which may enhance, moderate or potentiate the effect of an active principle in another population. In related embodiments, the dosage form of the invention may comprise multiple populations of beads. The active principles may be the same or different as between populations. The two populations of beads may, in certain embodiments, be differentially coated, whether singularly or multiply, so as to provide different release profiles of the same or different active ingredient(s).

The dosage form of the invention is suitable for oral administration.

The invention includes oral dosage forms comprising multiple shaped units, e.g. beads, of the invention, therefore.

Where compositions include at least two active agents, the composition may as previously described comprise at least two agents (one being a microorganism selected from live, killed, attenuated and inactivated microorganisms) within a hydrogel-forming polymer bead or shaped unit (whether within the polymer phase or the surfactant phase, or both) for co-release, and/or it may comprise at least two agents in different parts of the composition for sequential, e.g. pulsed, release. From the aspect of sequential release, the composition may comprise an active agent within a hydrogel-forming polymer bead or shaped unit (whether within the polymer phase or the surfactant phase, or both) and an active agent in a coating layer; optionally it may comprise two or more active agents in different coating layers or the same active agent in two or more different coating layers.

EXAMPLES

In the following examples, all percentages and ratios are by weight.

The examples describe the preparation of beads of generally spherical shape and typically having a diameter of 1 to 2 mm. The beads are manufactured according to the following general method:

Method of Preparation

Surfactant Phase

The antigen (i.e. microorganism) and the adjuvant(s) are dissolved/dispersed in Kolliphor HS 15. When the antigen or the adjuvant is supplied in an aqueous solution, the solution is mixed with Kolliphor HS 15 until a homogeneous mixture is achieved. The temperature is kept at 35-40° C. to maintain the Kolliphor HS as a liquid.

Gelatin Phase

D-Sorbitol is dissolved in water at room temperature, then gelatin is added and the temperature is increased up to 60-70° C. The solution is stirred until complete dissolution of the components. (The adjuvant aqueous solution can be used to prepare the gelatin phase if required, optionally in combination with water, but this option is not a feature of the examples).

Mixing of the Two Phases

Surfactant Phase and Gelatin phase are mixed at different w/w ratios (as shown in table 1). The resulting mixture is stirred at 60-70° C. to achieve homogeneity. The homogeneous solution is ejected through a single orifice to form droplets which fall into a cooling oil medium (Miglyol 810N) at 8-10° C. The nozzle size (diameter) may be from 0.5 to 3.5 mm.

After approximately 30 minutes, beads are recovered from the cooling oil solution, centrifuged to eliminate excess oil and then dried at room temperature.

All formulations have been coated with Eudragit L 30 D 55.

Specifically, Formulations 1 and 2 were obtained as follows:

Formulation 1.

Surfactant Premix: Kolliphor HS 15 (18.02%), ETEC Suspension* (81.98%).

Aqueous Premix: Gelatin (17.15%), D-Sorbitol (1.68%), ETEC Suspension*(81.18%). *ETEC suspension contains $1 \times 10^{10}$ cells per gram.

The two phases are mixed at a weight ratio of 1:1.69 surfactant premix to aqueous premix.

Dry Composition:

| Component | % |
|---|---|
| Kolliphor HS 15 | 36.21 |
| Gelatin | 58.11 |
| D-sorbitol | 5.68 |
| ETEC Cells | See note below |

Note:
$4.8 \times 10^{10}$ ETEC cells have been used to manufacture Formulation 1; given a batch size of 1093.1 mg and an average weight of 1 bead equal to 2.1 mg, the total number of beads in the batch is 1093.1 mg/2.1 = 521 beads. The concentration of ETEC cells per bead is therefore: $4.8 \times 10^{10}/521 = 9.2 \times 10^{7}$ cells per bead.

Beads were coated to achieve 5.9% weight gain of Eudragit L 30 D-55.

Formulation 2.

Surfactant premix: Kolliphor HS 15 (14.81%), alphaGal-Cer (0.08%), ETEC suspension* (85.11%).

Aqueous Premix: Gelatin (17.17%), D-Sorbitol (1.71%), ETEC Suspension* (81.12%).

*ETEC suspension contains $1 \times 10^{10}$ cells per gram.

The two phases are mixed at a weight ratio of 1:1.43 surfactant premix to aqueous premix.

Dry Composition:

| Component | % |
|---|---|
| Kolliphor HS 15 | 35.31 |
| Gelatin | 58.66 |
| D-sorbitol | 5.85 |
| Alpha-Gal-Cer | 0.18 |
| ETEC Cells | See note below |

Note:
$4.8 \times 10^{10}$ ETEC cells have been used to manufacture Formulation 1; given a batch size of 1084.4 mg and an average weight of 1 bead equal to 2.1 mg, the total number of beads in the batch is 1084.4 mg/2.1 = 517 beads. The concentration of ETEC cells per bead is therefore: $4.8 \times 10^{10}/521 = 9.3 \times 10^{7}$ cells per bead.

Given the batch size of 1084.4 mg dry weight, the absolute quantity (dry weight) of each component in the batch was as follows:

| Component | Quantity |
|---|---|
| Kolliphor HS 15 | 382.90 mg |
| Gelatin | 636.11 mg |
| D-sorbitol | 63.48 mg |
| Alpha-Gal-Cer | 1.95 mg |
| ETEC Cells | $4.8 \times 10^{10}$ |

A summary of various ratios of Formulation 2 is presented in the following table:

| Ratio (dry weight mg to $1 \times 10^{10}$ cells) | Value |
|---|---|
| Kolliphor HS 15:ETEC Cells | 79.77 mg:$1 \times 10^{10}$ cells |
| Gelatin:ETEC Cells | 132.52 mg:$1 \times 10^{10}$ cells |
| D-sorbitol:ETEC Cells | 13.23 mg:$1 \times 10^{10}$ cells |
| Alpha-Gal-Cer:ETEC Cells | 0.41 mg:$1 \times 10^{10}$ cells |

Note:
the above calculated FIGURES are an approximation which disregards the mass of water in the ETEC suspension and the mass of any residual water in the beads.

The teaching of this paragraph applies to the entire disclosure of the application, including all compatible embodiments of the description and all compatible claims. The invention includes compositions having a Feature selected from Feature 1, Feature 2, Feature 3 and Feature 4 of the following table. In the table, the word "cells" refers to the microorganism cells of the composition concerned, e.g. cells of any bacterium, fungus or unicellular pathogen referred to herein.

| Feature | Ratio (dry wt mg to $10^{10}$ cells) | Range 1 | Range 2 |
|---|---|---|---|
| 1 | Surfactant:Cells | 25-125 mg:$10^{10}$ cells | 50-100 mg:$10^{10}$ cells |
| 2 | Hydrogel-forming polymer:Cells | 75-175 mg:$10^{10}$ cells | 100-150 mg:$10^{10}$ cells |
| 3 | Plasticiser:Cells | 2-25 mg:$10^{10}$ cells | 5-20 mg:$10^{10}$ cells |
| 4 | Adjuvant:Cells | 0.1-10 mg:$10^{10}$ cells | 0.25-5 mg:$10^{10}$ cells |

The invention across its entire disclosure (as described in the preceding paragraph) further includes compositions having any one of the following combinations of Features of the above table:

For Range 1: Feature 1 & Feature 2; Feature 1 & Feature 3; Feature 1 & Feature 4; Feature 2 & Feature 3; Feature 2 & Feature 4; Feature 3 & Feature 4; Feature 1 & Feature 2 & Feature 3; Feature 1 & Feature 3 & Feature 4; Feature 1 & Feature 2 & Feature 4; Feature 2 & Feature 3 & Feature 4; Feature 1 & Feature 2 & Feature 3 & Feature 4. For Range 2: Feature 1 & Feature 2; Feature 1 & Feature 3; Feature 1 & Feature 4; Feature 2 & Feature 3; Feature 2 & Feature 4; Feature 3 & Feature 4; Feature 1 & Feature 2 & Feature 3; Feature 1 & Feature 3 & Feature 4; Feature 1 & Feature 2 & Feature 4; Feature 2 & Feature 3 & Feature 4; Feature 1 & Feature 2 & Feature 3 & Feature 4.

The invention across its entire disclosure further includes compositions having any of the following ratios of adjuvant to cells (dry wt mg to $10^{\wedge}10$ cells): 0.1-100 mg:$10^{\wedge}10$ cells, 0.2-10 mg:$10^{\wedge}10$ cells, 0.25-10 mg:$10^{\wedge}10$ cells; 0.4-10 mg:$10^{\wedge}10$ cells; 0.2-5 mg:$10^{\wedge}10$ cells, 0.25-5 mg:$10^{\wedge}10$ cells; 0.4-5 mg:$10^{\wedge}10$ cells; 1-10 mg:$10^{\wedge}10$ cells, 2-10 mg:$10^{\wedge}10$ cells; 4-10 mg:$10^{\wedge}10$ cells; 10-100 mg:$10^{\wedge}10$ cells, 25-100 mg:$10^{\wedge}10$ cells; 50 mg-100 mg:$10^{\wedge}10$ cells; 10-50 mg:$10^{\wedge}10$ cells, 10-30 mg:$10^{\wedge}10$ cells; 10 mg-20 mg:$10^{\wedge}10$ cells. The teaching of this paragraph applies e.g. to each of Features 1, 2 and 3 in the above table in respect of Ranges 1 and 2 and to combinations of two or three of Features 1, 2 and 3 mentioned in the immediately preceding paragraph. The microorganism may consist of one or more unicellular microorganisms, for example selected from bacteria and unicellular fungi, and the ratio of adjuvant to the aggregate amount of unicellular microorganisms (mg dry weight of adjuvant to $10^{\wedge}10$ cells) may in this case be as recited earlier in this paragraph and elsewhere herein. The microorganism may comprise or be any one or more, e.g. one, two or three, microorganisms mentioned in this specification. The microorganism may comprise or be any one or more, e.g. one, two or three, bacteria mentioned in this specification. The microorganism may comprise or be ETEC. The microorganism may comprise or be h. pylori.

The invention across its entire disclosure therefore includes compositions in which the microorganism consists of one or more unicellular microorganisms. In such compositions, the ratio of surfactant to the aggregate amount of unicellular microorganisms (mg dry weight of surfactant to $10^{\wedge}10$ cells) may be, for example, from 10-200 mg:$10^{\wedge}10$ cells and optionally from 25-125 mg:$10^{\wedge}10$ cells, e.g. from 25-150 mg:$10^{\wedge}10$ cells, 25-100 mg:$10^{\wedge}10$ cells, 50-200 mg:$10^{\wedge}10$ cells, 50-100 mg:$10^{\wedge}10$ cells or 60-90 mg:$10^{\wedge}10$ cells.

The dry weight ratio of adjuvant to surfactant (Kolliphor HS) in the examples is about 175 to 1, and this is an optional ratio applicable across the entire scope of the disclosure. Also to be mentioned as applicable across the entire scope of the disclosure are optional ratios of 200 to 1 or less, 150 to 1 or less, 100 to 1 or less and 50 to 1 or less.

Beads were coated on MFL01 to achieve 5.5% weight gain of Eudragit L 30 D-55.

A summary of the formulations prepared is presented in the table below:

| Formulation | Antigen | Adjuvant(s) | Kolliphor HS15 to Gelatin w/w ratio (dry weight) | Weight gain of L 30 D 55 achieved |
|---|---|---|---|---|
| 1 | ETEC ($2.76 \times 10^{\wedge}8$ cells per dose (3 beads)) | None | 1:1.60 | 5.9% |
| 2 | ETEC ($2.78 \times 10^{\wedge}8$ cells per dose (3 beads)) | aGalCer (0.18%) | 1:1.66 | 5.5% |

The antigen shown in the above table (ETEC) comprised formalin-killed *E. coli* K12 bacteria (expressing CFA/I fimbriae on the surface).

The above compositions were used to determine whether and to what extent oral immunisation of mice with these compositions (with and without alpha-GalCer as adjuvant) would induce potent mucosal and systemic antibody responses.

Female BALB/c mice were immunised by oral gavage on days 0 and 1 with bicarbonate buffer as a control or with ETEC ($3 \times 10^8$ cells/dose) in bicarbonate buffer either alone or together with alpha-GalCer (10 pg/dose) or cholera toxin (CT; 10 µg/dose) as adjuvant or immunized orally with LEDDS™ containing ETEC ($3 \times 10^8$ cells/dose) alone or together with alpha-GalCer (10 µg/dose). Mice were boosted on days 13, 14, 27 and 28 with an identical series of immunizations. Groups of mice (n=5) were bled 1 day prior to booster immunizations and 12 days after the final dose for determination of IgG and IgA antibody titres. Faecal pellets were collected from all mice 1 day prior to booster immunizations and 12 days after the final immunization to determine mucosal antibody responses. Two weeks post the final immunization, mice were sacrificed and intestinal washes were collected. Extracts of both the small and large intestines of mice were also obtained and frozen in buffer with protease inhibitors for subsequent analysis of mucosal antibodies using saponin to extract proteins from the intestines.

Experimental Groups
1. Bicarbonate Buffer
2. ETEC
3 ETEC+alpha-GalCer
4. ETEC+CT
5. LEDDS™ (ETEC)
6. LEDDS™ (ETEC+alpha-GalCer)

Enhanced antibody responses were found in the sera, faecal pellets, saliva and intestinal washes of mice immunized with LEDDS™ containing ETEC and alpha-GalCer compared to mice immunized with non-adjuvanted LEDDS™ vaccine or with ETEC in solution.

Results
Please Refer to FIGS. 1 to 8

ETEC alone in solution: Oral immunisation of mice with the ETEC vaccine in solution did not induce an antigen-specific IgA antibody response; CFA/1-specific IgA was only detectable in the faecal pellets (FIG. 2) or serum (FIG. 4) of 1/5 mice immunized with this vaccine.

ETEC+alpha-GalCer in solution: The addition of alpha-GalCer as adjuvant in solution did not result in significantly enhanced antigen-specific antibody titres either mucosally or systemically compared to ETEC alone in solution.

LEDDS™ (ETEC alone): The delivery of the ETEC vaccine in a non-adjuvanted LEDDS™ formulation did not result in detectable mucosal antibodies in the faecal pellets (FIGS. 1 and 2) or the intestines (FIGS. 6, 7 and 8) of any immunised mice. Furthermore, systemic antibody responses were not significantly enhanced in mice immunized with this formulation compared to those administered the ETEC vaccine in solution orally (FIGS. 3 and 4).

Figure 6:
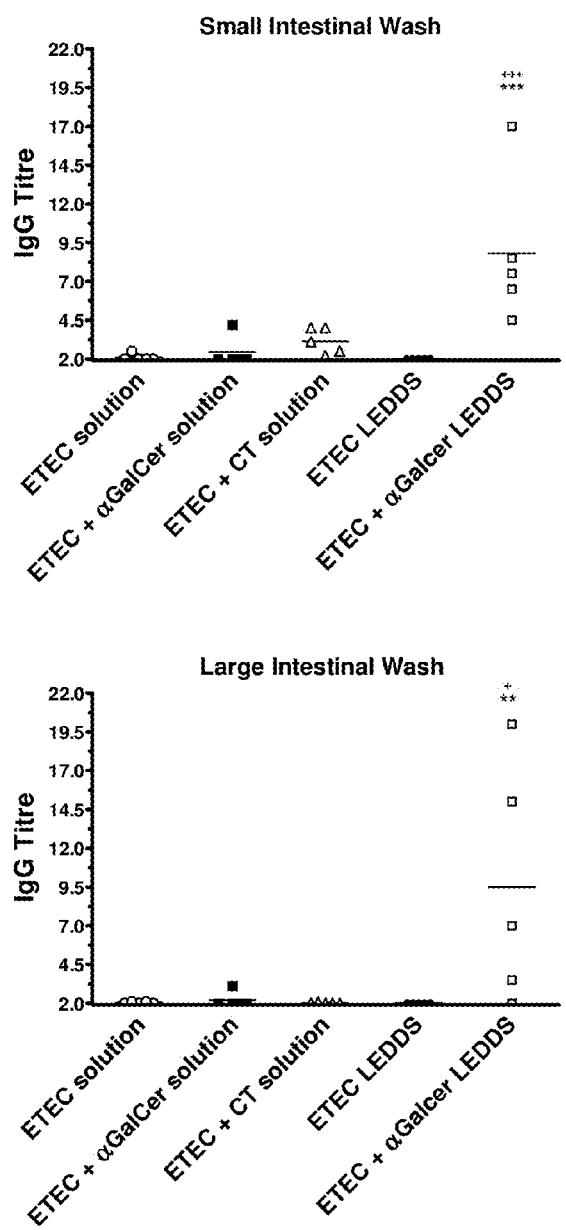
FIG. 6. Oral immunization of mice with LEDDS™ containing ETEC and alpha-GalCer as adjuvant induces IgG antibody responses locally in the intestines. Mice were immunized as described in the legend to FIG. 1. Antigen-specific IgG antibody titres were determined by ELISA on both small and large intestinal washes recovered two weeks post the final series of immunizations. +P<0.05, +++ P<0.001 ETEC+alpha-GalCer LEDDS™ vs ETEC solution,  P<0.01, * P<0.001 ETEC+alpha-GalCer LEDDS™ vs ETEC LEDDS™.
Figure 7:
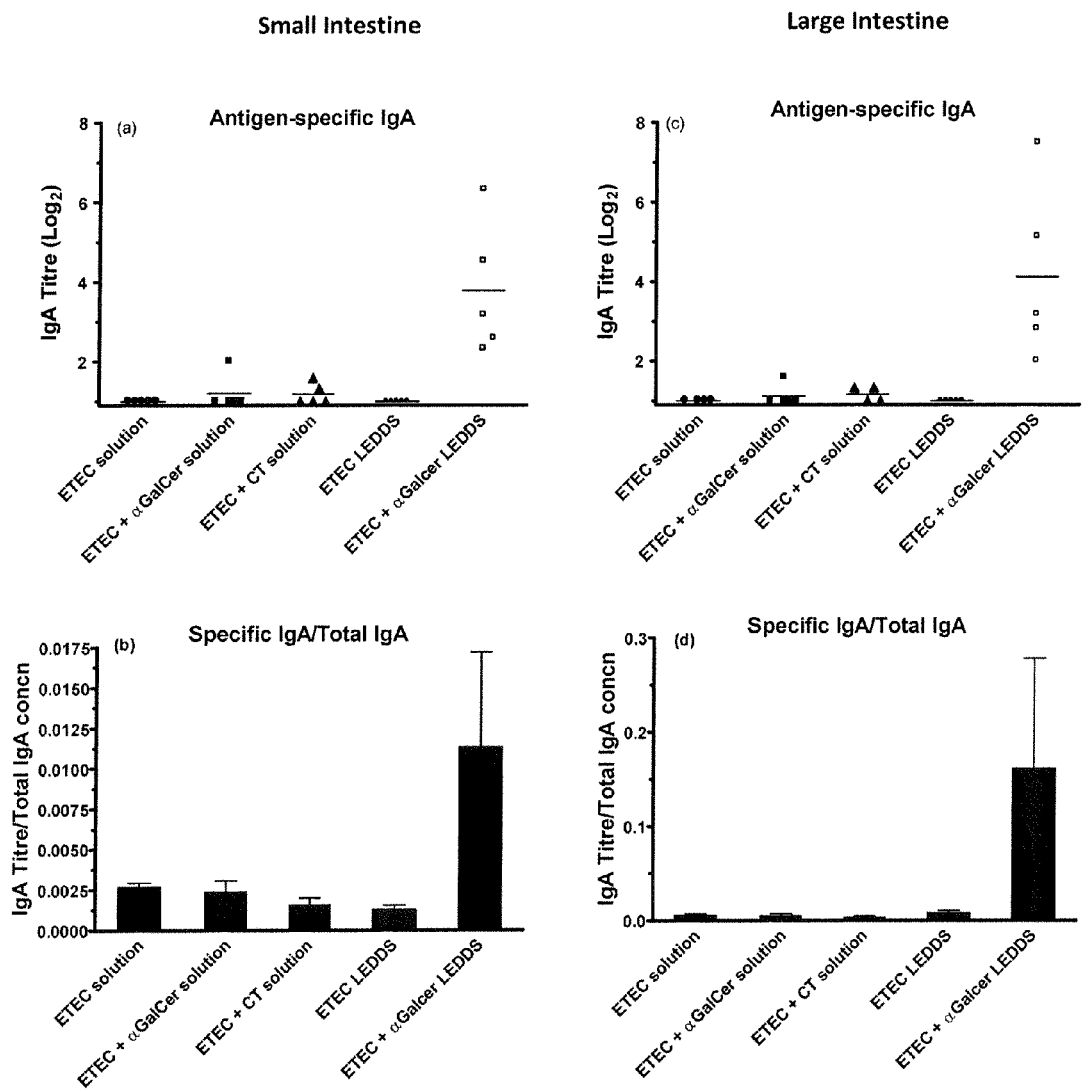
FIG. 7. Oral immunization of mice with LEDDS™ containing ETEC and alpha-GalCer as adjuvant induces significant IgA antibody responses locally in the intestines. Mice were immunized as described in the legend to FIG. 1. Antigen-specific IgA antibody titres and total IgA antibody concentrations were determined by ELISA on supernatants obtained from saponin-treatment of both small and large intestinal extracts recovered two weeks post the final series of immunizations. Results are expressed as CFA/I-specific IgA endpoint titres ((a) and (c)) or antigen-specific IgA titres/total IgA concentrations ((b) and (d)). +++P<0.001 ETEC+alpha-GalCer LEDDS™ vs ETEC solution, *** P<0.001 ETEC+alpha-GalCer LEDDS™ vs ETEC LEDDS™.
Figure 8:
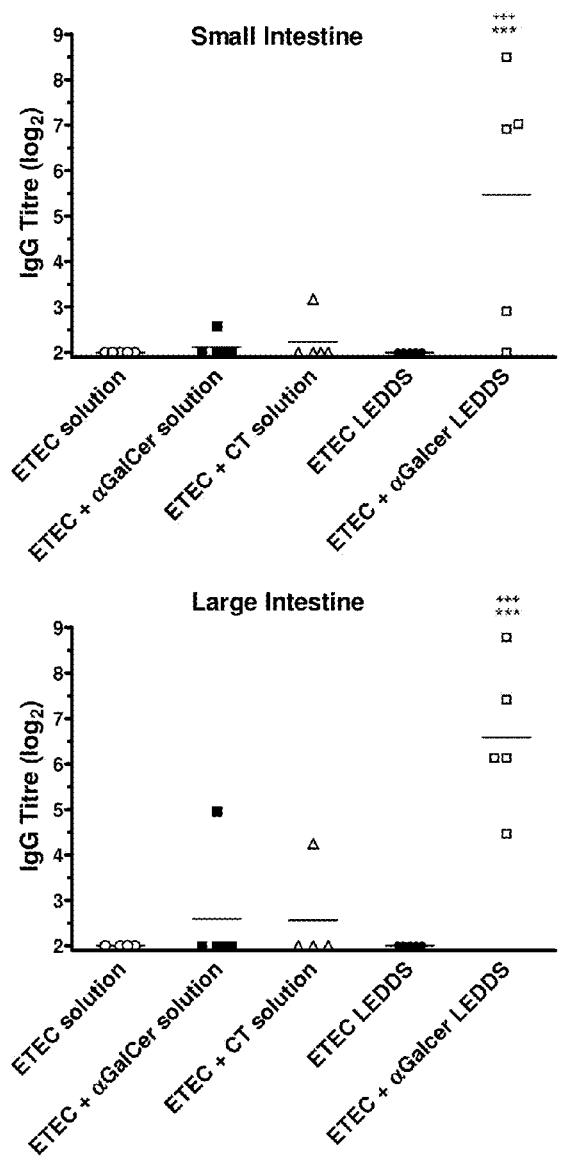
FIG. 8. Oral immunization of mice with LEDDS™ containing ETEC and alpha-GalCer as adjuvant induces significant IgG antibody responses locally in the intestines. Mice were immunized as described in the legend to FIG. 1. Antigen-specific IgG antibody titres were determined by ELISA on supernatants obtained from saponin-treatment of both small and large intestinal extracts recovered two weeks post the final series of immunizations. +++P<0.001 ETEC+alpha-GalCer LEDDS™ vs ETEC solution, *** P<0.001 ETEC+alpha-GalCer LEDDS™ vs ETEC LEDDS™.
Figure 9:
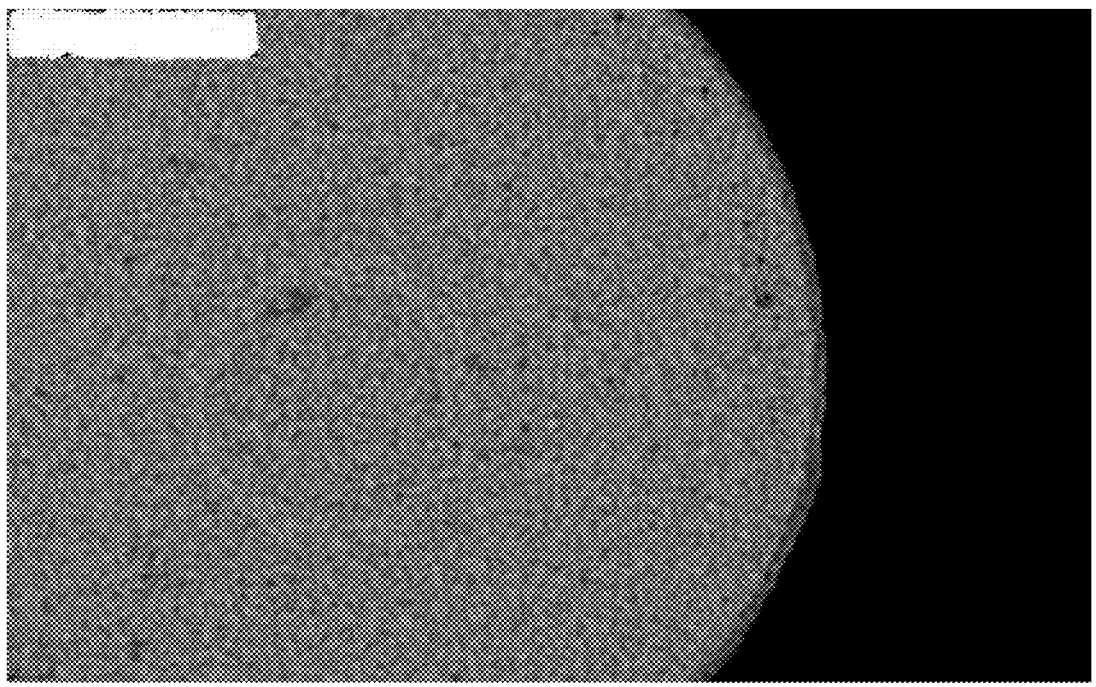
FIG. 9 shows an x-ray tomography image of the bead that is described in WO 2010/133609.
Figure 10:
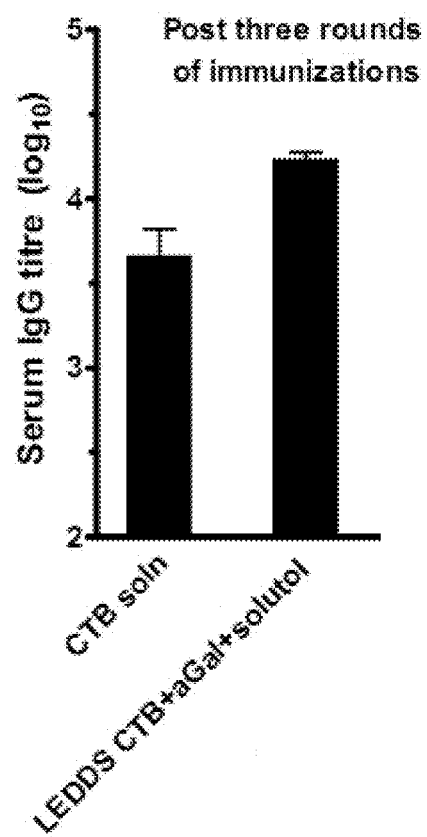
FIG. 10 shows the results of a reference study (1). Oral administration to mice of Cholera toxin subunit B (CTB) with and without alpha-GalCer and Kolliphor HS 15 in LEDDS™ induces antigen-specific IgG responses systemically. Mice were immunised analogously to the legend to FIG. 1. Serum samples were collected 12 days post the final immunization and antigen-specific IgG titres (a) were assessed by ELISA.
Figure 11:
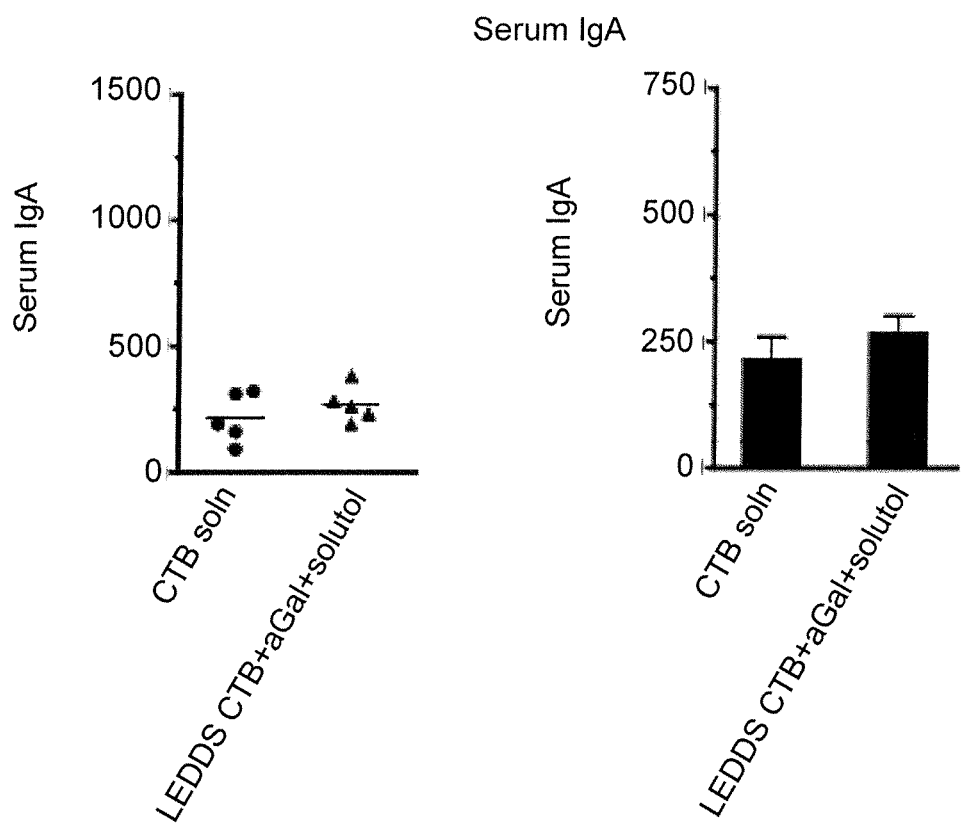
FIG. 11 shows the results of a reference study (1). Oral administration to mice of Cholera toxin subunit B (CTB) with and without alpha-GalCer and Kolliphor HS 15 in LEDDS™ induces antigen-specific IgG responses systemically. Mice were immunised analogously to the legend to FIG. 1. Serum samples were collected 12 days post the final immunization and antigen-specific IgA titres (a) and total IgA antibody concentrations (b) were assessed by ELISA.
Figure 12:
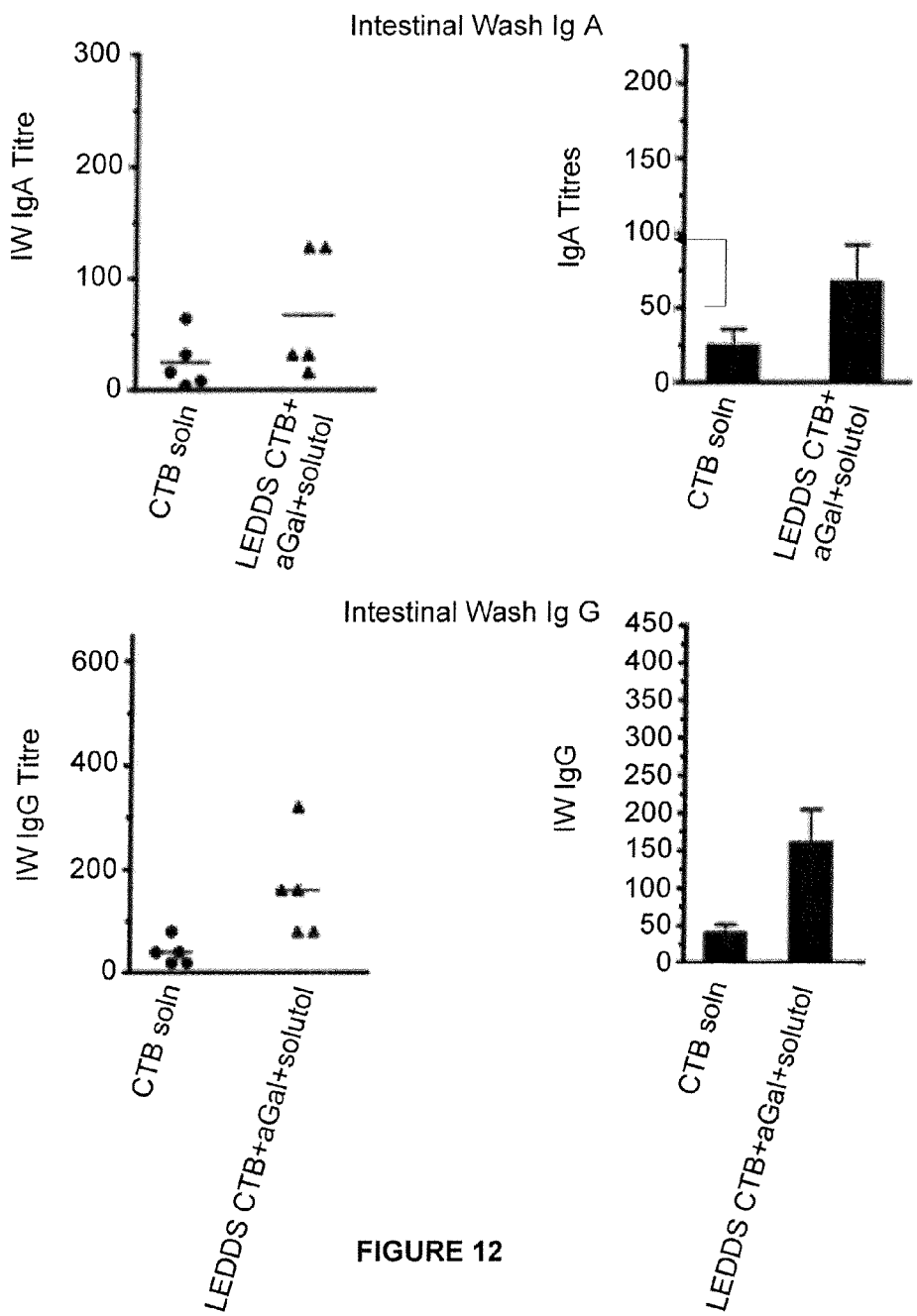
FIG. 12 shows the results of a reference study (2) Oral administration to mice of Cholera toxin subunit B (CTB) with and without alpha-GalCer and Kolliphor HS 15 in LEDDS™ induces antigen-specific IgG and IgA responses locally in the intestines. Mice were immunized analogously to the legend to FIG. 1.

LEDDS™ (ETEC+alpha-GalCer): The delivery of ETEC in LEDDS™ together with alpha-GalCer as adjuvant induced a specific IgA response in the faecal pellets (FIG. 2), the sera (FIG. 4) and the intestines (FIG. 7) of all immunized mice after the final oral immunization. Faecal pellets from mice immunized with this LEDDS™ formulation contained significantly higher mucosal IgA and IgG (FIG. 1) compared to either ETEC+alpha-GalCer in solution or ETEC alone in LEDDS™. While specific IgA antibodies were detected after the second series of vaccinations, the enhancing effect of the LEDDS™ formulation was most clearly seen after the $3^{rd}$ series of immunizations. Furthermore, following extraction of intestinal proteins by saponin, significantly greater antigen-specific IgG and IgA antibody titres were found in the intestines of mice immunized orally with LEDDS™ containing ETEC and alpha-GalCer compared to mice administered non-adjuvanted vaccine either in solution or in LEDDS™ (FIGS. 7 and 8). Significantly enhanced CFA/I-specific IgG antibodies were also found in the small intestinal washes of mice immunized with LEDDS™ containing ETEC and alpha-GalCer (FIG. 6).

Figure 3:
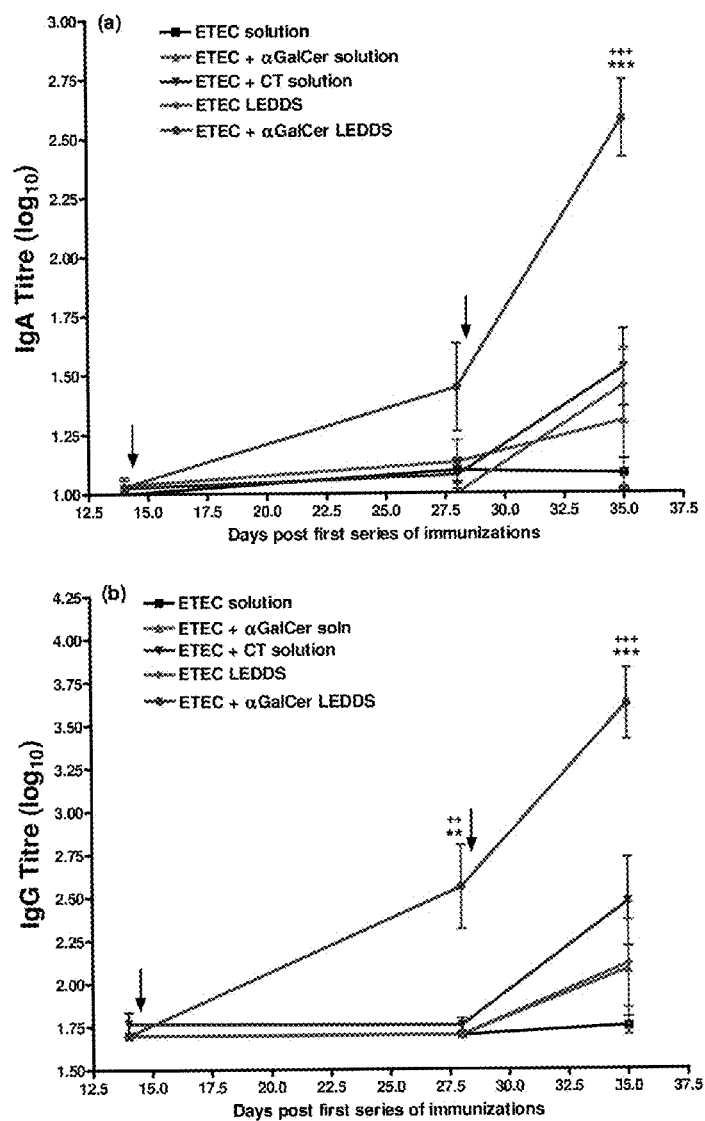
FIG. 3. Oral immunisation with ETEC and alpha-GalCer in LEDDS™ induces strong antigen-specific systemic antibody responses. Mice were immunised as described in the legend to FIG. 1. Antigen-specific IgA and IgG antibody responses were assessed by ELISA on serum samples recovered 1 day prior to booster immunizations and 12 days post the final immunization. Arrows represent booster immunizations. , P<0.01, *, P<0.001 ETEC+alpha-GalCer LEDDS™ vs ETEC+alpha-GalCer solution, ++, P<0.01, +++, P<0.001 ETEC+alpha-GalCer LEDDS™ vs ETEC LEDDS™.
Figure 4:
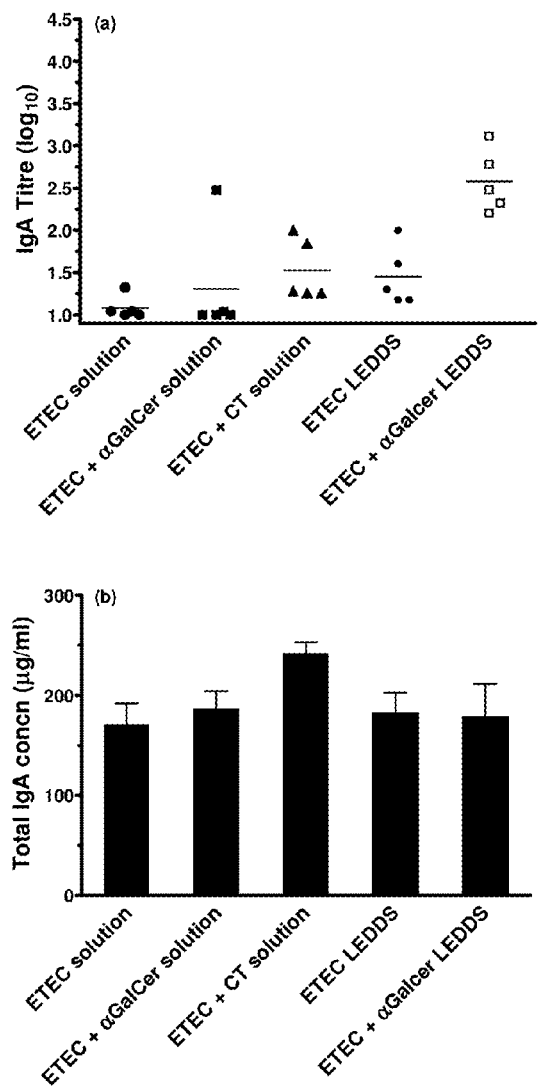
FIG. 4. Oral administration of ETEC with alpha-GalCer in LEDDS™ induces potent antigen-specific IgA responses systemically. Mice were immunised as described in the legend to FIG. 1. Serum samples were collected 12 days post the final immunization and antigen-specific IgA titres (a) and total IgA antibody concentrations (b) were assessed by ELISA.
Figure 5:
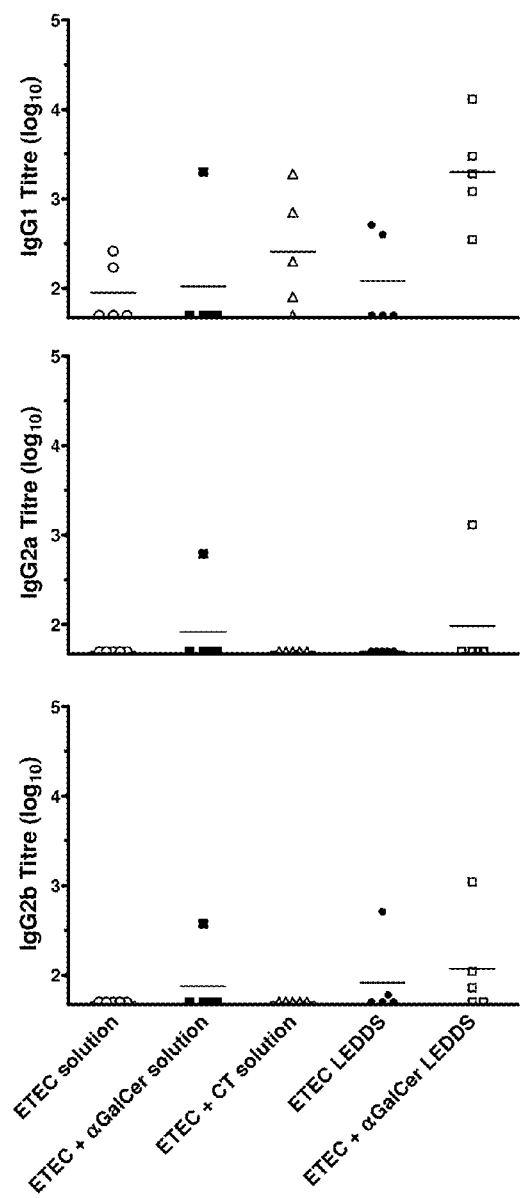
FIG. 5. Oral immunisation of mice with ETEC and alpha-GalCer in LEDDS™ induces a predominant IgG1 antibody response systemically. Mice were immunized as described in the legend to FIG. 1. Antigen-specific IgG1, IgG2a and IgG2b antibody titres were assessed by ELISA on sera recovered 12 days post the final immunization. Results are presented as IgG1, IgG2a or IgG2b end-point titres.

In terms of systemic IgA and IgG, the strongest responses were again detected in mice immunized orally with LEDDS™ containing ETEC and alpha-GalCer (FIGS. 3, 4 and 5). Antigen-specific IgG antibodies were significantly greater from the sera of mice immunized with ETEC and alpha-GalCer in LEDDS™, following either two or three series of oral immunizations, compared to either ETEC+alpha-GalCer in solution or ETEC alone in LEDDS™ (FIG. 3). Analysis of the antibody subclasses induced by this formulation revealed that IgG1 was the main subtype induced (FIG. 5).

Conclusions

Oral immunization of mice with ETEC formulated in LEDDS™ containing alpha-GalCer induced significantly stronger mucosal IgA and IgG antibody responses in the faecal pellets and intestines compared to immunization with ETEC in solution or ETEC in LEDDS™ without alpha-GalCer.

Immunization of mice with LEDDS™ containing ETEC and alpha-GalCer also induced antigen-specific antibody responses in the serum, which were significantly greater than those generated in mice immunized orally with non-adjuvanted ETEC vaccine either in solution or in LEDDS™

In summary, these data confirm that a LEDDS™ formulation containing ETEC and alpha-GalCer as adjuvant induces potent mucosal and systemic antibody responses. Furthermore, this study shows that by extraction of intestinal proteins using saponin, antigen-specific antibodies could be detected from the intestines of mice immunized orally with LEDDS™ containing ETEC and alpha-GalCer and that these responses were significantly greater than those induced by non-adjuvanted vaccine.

Example 18

Aspect Ratio

Minibeads were made generally following the above-described procedures by extrusion from a nozzle to fall into a cooling medium. In this instance, though, the beads did not fall within the invention in having a microorganism as active Some of the beads were then coated as described herein with a Surelease™ and pectin mixture. Sample populations of the coated beads and sample populations of uncoated beads were both typically found to have an average aspect ratio of 1.2 when measured using an Eyecon™ particle characteriser.

FURTHER DISCLOSURES OF THE INVENTION

The invention further includes the subject matters of the following clauses. These subject matters are combinable with the entire teachings of the specification, except of course those which are mutually exclusive.

1. A composition comprising:
   a matrix comprising a hydrogel-forming polymer; and
   comprised in the matrix, a microorganism selected from live, killed, attenuated and inactivated microorganisms, a surfactant and an adjuvant.
2. A composition comprising
   a surfactant
   a microorganism selected from live, killed, attenuated and inactivated microorganisms
   an adjuvant, and
   a hydrogel-forming polymer in which the surfactant, the microorganism and the adjuvant are included;
   and wherein the composition when combined with water is capable of releasing self-assembly structures comprising surfactant and adjuvant.
3. A composition of clause 1 or clause 2 wherein at least a portion of the adjuvant is associated with at least a portion of the surfactant.
4. A composition of any preceding clause wherein at least a portion of the microorganism content is associated with at least a portion of the surfactant.
5. A composition of any preceding clause wherein the weight ratio of said surfactant to the hydrogel-forming polymer is from 1:0.5 to 1:2.5 and optionally from 1:0.5 to 1:2 e.g. from 1:1 to 1:2.5 or from 1:1 to 1:2.
6. A composition of clause 5 wherein the weight ratio of said surfactant to the hydrogel-forming polymer is from 1:1.4 to 1:1.8 e.g. 1:1.6 to 1:1.7.
7. A composition of any preceding clause wherein the hydrogel-forming polymer is selected from thermotropic hydrogel-forming polymers and combinations thereof.
8. A composition of clause 7 wherein the hydrogel-forming polymer is selected from the group consisting of gelatin, agar, agarose, pectin, carrageenan, and chitosan, and combinations thereof.
9. A composition of clause 7 or clause 8 wherein the hydrogel-forming polymer comprises, or is, gelatin.
10. A composition of any preceding clause comprising chitosan.
11. A composition of any preceding clause wherein the microorganism is a bacterium and optionally is a bacterium expressing a colonisation factor, e.g. colonisation factor antigen I (CAF/I).
12. A composition of clause 11 wherein the bacterium is enterotoxigenic *E. coli.*
13. A composition of clause 11 wherein the bacterium is *Helicobacter pylori.*
14. A composition of any of clauses 1 to 10 wherein the microorganism is a virus or a fungus.
15. A composition of any preceding clause which further comprises one or more antigens additional to the microorganism, e.g. comprises plural types of microorganism, for example plural types of unicellular microorganisms, and optionally comprises plural strains of a bacterium.

16. A composition of any preceding clause wherein the adjuvant is, or comprises, an immunostimulator.
17. A composition of clause 16 wherein the immunostimulator is a T-cell activator or an activator, of an antigen-presenting cell or other immune cell.
18. A composition of clause 16 wherein the adjuvant is, or comprises, a ceramide, particularly α-GalCer.
19. A composition of any of the preceding clauses wherein the microorganism consists of one or more unicellular microorganisms and the ratio of adjuvant to the aggregate amount of unicellular microorganisms (mg dry weight of adjuvant to 10^10 cells) is from 0.1-100 mg:10^10 cells and optionally from 0.1-10 mg:10^10 cells, e.g. 0.25-5 mg:10^10 cells, particularly 0.4-5 mg:10^10 cells.
20. A composition of any preceding clause wherein the surfactant is a non-ionic surfactant.
21. A composition of clause 20 wherein the surfactant is selected from the group consisting of: macrogol esters; macrogol ethers; diblock copolymers; triblock copolymers; and amphiphilic polymers; and combinations thereof.
22. A composition of clause 20 or clause 21 wherein the surfactant comprises an alkyl chain which is unsubstituted or is substituted by a single hydroxy group.
23. A composition of any of clauses 20 to 22 wherein the surfactant comprises a PEG chain
24. A composition of clause 23 wherein the surfactant is, or comprises, a PEGylated fatty acid, e.g. a PEGylated hydroxy fatty acid, and optionally wherein the PEGylated fatty acid is in combination with free PEG.
25. A composition of clause 24 wherein the surfactant is macrogol-15-hydroxystearate.
26. A composition of any preceding clause which further comprises a cationic lipid, optionally wherein the cationic lipid is selected from DOTAP and DOSPER.
27. A composition of any preceding clause wherein the microorganism consists of one or more unicellular microorganisms and the ratio of surfactant to the aggregate amount of unicellular microorganisms (mg dry weight of surfactant to 10^10 cells) is from 10-200 mg:10^10 cells and optionally from 25-125 mg:10^10 cells, e.g. from 25-150 mg:10^10 cells, 25-100 mg:10^10 cells, 50-200 mg:10^10 cells, 50-100 mg:10^10 cells or 60-90 mg:10^10 cells.
28. A composition of any preceding clause which is in the form of a bead having a diameter of from 0.5 mm to 5 mm.
29. A composition of clause 28 wherein the bead has a diameter of from 1 mm to 2 mm.
30. A composition of clause 28 or clause 29 wherein the hydrogel-forming polymer is substantially dry and wherein the bead has a coating.
31. A composition of clause 30 wherein the coating comprises an active ingredient.
32. A composition of clause 30 or clause 31 wherein the coating is an immediate release coating.
33. A composition of any of clauses 30 to 32 wherein the bead comprises a controlled release coating, e.g. an enteric coating.
34. A composition of any preceding clause which further comprises an immune-enhancing nutrient, for example one or more nutrients selected from vitamins A, B (e.g. one or a combination of vitamin B6, vitamin B12, niacin (vitamin B3), pantothenic acid, riboflavin (vitamin B2), thiamin (vitamin B1) and folic acid), vitamin C, vitamin E; carotenoids, e.g. beta-carotene, iron, manganese, selenium and zinc, for example wherein the composition comprises a nutrient: in the matrix (the hydrogel-forming polymer), in association with the surfactant, and/or in a coating.
35. A composition of any preceding clause wherein the microorganism comprises, or is, a combination of intact and fragmented microorganism cells and optionally is formalin-killed.
36. A process which comprises mixing:
   i) a surfactant premix comprising a surfactant, an adjuvant and a microorganism selected from live, killed, attenuated and inactivated microorganisms; and
   ii) a liquid aqueous premix comprising water and a hydrogel-forming polymer.
37. A process of clause 36 which further comprises ejecting the mixture of i) and ii) through a single orifice nozzle to form droplets, the hydrogel-forming polymer then being caused or allowed to solidify whereby the droplets form beads.
38. A process of clause 37 wherein the hydrogel-forming polymer is a thermotropic polymer or a mixture of thermotropic polymers, and the aqueous premix is at an elevated temperature and the surfactant premix is at a temperature not exceeding ambient temperature, the two premixes flowing through respective feed lines to a mixing apparatus where the two premixes are mixed, and wherein at least one of the two premixes travels a greater distance through its feedline than the mixture does in travelling from the mixing apparatus to the nozzle.
39. A process of clause 38 wherein the two premixes are mixed by in-line mixing apparatus juxtaposed to the nozzle.
40. A process which comprises mixing (i) a surfactant, (ii) a microorganism selected from live, killed, attenuated and inactivated microorganisms, and (iii) an adjuvant.
41. A process of clause 40 wherein a hydrophobic excipient, for example a medium chain triglyceride, is mixed with the surfactant, the microorganism and the adjuvant.
42. A process of clause 40 or clause 41 which further comprises mixing the resultant surfactant mix with an aqueous premix comprising water and a hydrogel-forming polymer, the surfactant being in an amount sufficient to form self-assembly structures, e.g. micelles.
43. A process which comprises mixing materials comprising water, a hydrogel-forming polymer, a surfactant, and an active ingredient selected from live, killed, attenuated and inactivated microorganisms to form a dispersion of self-assembly structures, e.g. micelles, within an aqueous phase comprising the hydrogel-forming polymer.
44. A process of clause 43, which process is for forming an aqueous dispersion of self-assembly structures, e.g. micelles, and which comprises:
   (i) performing the method of clause 42 to form an aqueous phase premix;
   (ii) performing the method of clause 40 or clause 41 to form a surfactant phase premix; and then
   (iii) mixing the aqueous phase premix and the surfactant phase premix in proportions such that surfactant forms self-assembly structures, to form a dispersion of self-assembly structures.
45. A process of any of clauses 40 to 44 which further comprises forming the dispersion into shaped units, for example beads.
46. A process of clause 45 wherein the forming comprises ejecting the dispersion through a single orifice nozzle to form droplets which are caused or allowed to fall into a water immiscible cooling liquid in which the droplets cool to form beads, and then separating the beads from the cooling liquid.

47. A process of clause 45 or clause 46 which further comprises applying one or more coatings to the shaped units.

48. A process of clause 47 wherein the one or more coatings comprise at least one coating selected from an immediate release coating and a controlled release coating, e.g. wherein the controlled release coating is an enteric coating.

49. A process of any of clauses 36 to 48 which further includes the feature(s) recited in in any one of clauses 5 to 27, 34 or 35, or in any combination of said clauses permitted by dependency.

50. An oral dosage form comprising a population of beads of any of clauses 28 to 35 or a population of shaped units obtainable by any of clauses 45 to 48.

51. A dosage form of clause 50 comprising a first population of said beads or shaped units and a second population of said beads or shaped units different from those of the first population.

52. A dosage form of clause 50 or clause 51 which is for use in an administration regimen comprising at least one booster administration.

53. A product having the characteristics of a composition obtained by drying a composition comprising a hydrogel having dispersed therein self-assembly structures, the composition further comprising a first active ingredient comprising an antigen selected from live, killed, attenuated and inactivated microorganisms and a second active ingredient comprising an adjuvant, and the composition optionally further being as defined in any of clauses 3 to 35, or in any combination of said clauses permitted by dependency.

54. The use in the manufacture of an oral dosage form, for example a gelatin capsule, of a product of clause 53.

55. A process for administering to a subject a microorganism selected from live, killed, attenuated and inactivated microorganisms, comprising orally administering to the subject a product comprising an antigen selected from live, killed, attenuated and inactivated microorganisms wherein the product is a composition as defined in any of clauses 1 to 35 or is a dosage form as defined in any of clauses 50 to 52 or is a product as defined in clause 53.

56. A process for vaccinating a subject against a disease caused by a microorganism, comprising orally administering to the subject a product comprising an antigen selected from live, killed, attenuated and inactivated microorganisms, wherein the product is a composition as defined in any of clauses 1 to 35 or is a dosage form as defined in any of clauses 50 to 52 or is a product as defined in clause 53, wherein the microorganism which is comprised in the product in inactivated or attenuated form is effective after administration of the product to produce an immunological response against said disease-causing microorganism.

57. A process of clause 55 or clause 56 which comprises repeating administration of a said product after a period of at least one week.

58. A process of clause 55 or clause 56 which comprises repeating at least twice administration of a said product, each administration being separated from each other administration by a period of at least one week.

The invention claimed is:

1. A composition comprising
a surfactant selected from a polyethoxylated hydroxy fatty acid; a microorganism selected from live, killed, attenuated and inactivated microorganisms, wherein the microorganism is a bacterium selected from the group consisting of enterotoxigenic *E. coli, Helicobacter pylori, Clostridium difficile, Shigella sonnei, Shigella boydii, Shigella dysenteriae* and *Shigella flexneri*;
a glycolipid adjuvant, and
a matrix comprising a hydrogel-forming polymer in which the surfactant, the microorganism and the adjuvant are included, wherein the hydrogel-forming polymer is selected from the group consisting of gelatin, agar, agarose, pectin, carrageenan, and chitosan, and combinations thereof;
and wherein the composition when combined with water is capable of releasing self-assembly structures comprising surfactant and adjuvant.

2. The composition of claim 1 wherein at least a portion of the adjuvant is associated with at least a portion of the surfactant.

3. The composition of claim 1 wherein at least a portion of the microorganism content is associated with at least a portion of the surfactant.

4. The composition of claim 1 wherein the weight ratio of said surfactant to the hydrogel-forming polymer is from 1:0.5 to 1:2.5.

5. The composition of claim 4 wherein the weight ratio of said surfactant to the hydrogel-forming polymer is from 1:1.4 to 1:1.8.

6. The composition of claim 1 wherein the hydrogel-forming polymer comprises, or is, gelatin.

7. The composition of claim 1 comprising chitosan.

8. The composition of claim 1 wherein the bacterium is enterotoxigenic *E. coli*.

9. The composition of claim 1 wherein the bacterium is *Helicobacter pylori*.

10. The composition of claim 1 which further comprises one or more antigens additional to the microorganism.

11. A composition of claim 1 wherein the adjuvant is, or comprises, an immunostimulator.

12. The composition of claim 11 wherein the immunostimulator is a T-cell activator or an activator, of an antigen-presenting cell or other immune cell.

13. The composition of claim 11 wherein the adjuvant is, or comprises, a ceramide.

14. The composition of claim 1 wherein the microorganism consists of one or more unicellular microorganisms and the ratio of adjuvant to the aggregate amount of unicellular microorganisms (mg dry weight of adjuvant to $10^{10}$ cells) is from 0.1-100 mg:$10^{10}$ cells.

15. The composition of claim 1 wherein the surfactant comprises an alkyl chain which is unsubstituted or is substituted by a single hydroxy group.

16. The composition of claim 1 wherein the surfactant is macrogol-15-hydroxystearate.

17. The composition of claim 1 which further comprises a cationic lipid.

18. The composition of claim 1 wherein the microorganism consists of one or more unicellular microorganisms and the ratio of surfactant to the aggregate amount of unicellular microorganisms (mg dry weight of surfactant to $10^{10}$ cells) is from 10-200 mg:$10^{10}$ cells.

19. The composition of claim 1 which is in the form of a bead having a diameter of from 0.5 mm to 5 mm.

20. The composition of claim 19 wherein the bead has a diameter of from 1 mm to 2 mm.

21. The composition of claim 19 wherein the hydrogel-forming polymer is substantially dry and wherein the bead has a coating.

22. The composition of claim 21 wherein the coating comprises an active ingredient.

23. The composition of claim 21 wherein the coating is an immediate release coating.

24. The composition of claim 21 wherein the bead comprises a controlled release coating.

25. The composition of claim 1 which further comprises an immune-enhancing nutrient.

26. The composition of claim 1 wherein the microorganism comprises, or is, a combination of intact and fragmented microorganism cells.

27. An oral dosage form comprising a population of beads of claim 19.

28. The dosage form of claim 27 comprising a first population of said beads and a second population of said beads different from those of the first population.

29. The composition of claim 1 wherein the weight ratio of said surfactant to the hydrogel-forming polymer is from 1:0.5 to 1:2.

30. The composition of claim 1 wherein the weight ratio of said surfactant to the hydrogel-forming polymer is from 1:1.6 to 1:1.7.

31. The composition according to claim 1 wherein the adjuvant is α-galactosylceramide.

32. The composition of claim 2 wherein the microorganism consists of one or more unicellular microorganisms and the ratio of adjuvant to the aggregate amount of unicellular microorganisms (mg dry weight of adjuvant to 10^10 cells) is from 0.4-5 mg:10^10 cells.

33. The composition of claim 1 wherein the surfactant is, or comprises, a PEGylated hydroxy fatty acid in combination with free PEG.

34. The composition of claim 21 wherein the bead comprises an enteric coating.

35. The composition of claim 1 wherein the composition is for oral administration.

36. The composition of claim 1 which further comprises a cationic lipid selected from DOTAP (N-[1-(2,3-dioleoyloxy)]-N,N,N-trimethylammonium propane methylsulfate) and DOSPER (1,3-dioleoyloxy-2-(6-carboxyspermyl)-propyl amide).

37. The composition of claim 1 wherein the microorganism is formalin-killed.

38. The composition of claim 1 wherein the wherein the glycolipid is dissolved in the surfactant.

39. A composition comprising
a surfactant comprising a macrogol-15-hydroxystearate, a microorganism selected from live, killed, attenuated and inactivated microorganisms, wherein the microorganism is a bacterium selected from the group consisting of enterotoxigenic *E. coli, Helicobacter pylori, Clostridium difficile, Shiaella sonnei, Shigella boydii, Shigella dysenteriae* and *Shiaella flexneri;*
an adjuvant comprising α-GalCer, and
a hydrogel-forming polymer in which the surfactant, the microorganism and the adjuvant, α-GalCer, are included, wherein the hydrogel-forming polymer is selected from the group consisting of gelatin, agar, agarose, pectin, carrageenan, and chitosan, and combinations thereof;
and wherein the composition when combined with water is capable of releasing self-assembly structures.

40. The composition of claim 39, wherein the microorganism is ETEC.

41. The composition of claim 25, wherein the nutrient is one or more nutrients selected from vitamin A, vitamin B, vitamin C, vitamin E, carotenoids, iron, manganese, selenium and zinc.

42. The composition of claim 41, wherein the vitamin B is selected from vitamin B6, vitamin B12, niacin (vitamin B3), pantothenic acid, riboflavin (vitamin B2), thiamin (vitamin B1) or folic acid.

43. The composition of claim 1 wherein the microorganism is *Clostridium difficile.*

44. The composition of claim 39 wherein the microorganism is *Helicobacter pylori.*

45. The composition of claim 39 wherein the microorganism is *Clostridium difficile.*

46. The composition of claim 39 wherein the hydrogel-forming polymer is gelatin.

47. The composition of claim 1, wherein the microorganism is selected from the group consisting of *Shigella sonnei, Shigella boydii, Shigella dysenteriae, and Shigella flexneri.*

48. The composition of claim 39, wherein the microorganism is selected from the group consisting of *Shigella sonnei, Shigella boydii, Shigella dysenteriae and Shigella flexneri.*

* * * * *